(12) United States Patent
Boesen

(10) Patent No.: US 9,951,116 B2
(45) Date of Patent: *Apr. 24, 2018

(54) ALPHA- AND GAMMA-MSH ANALOGUES

(71) Applicant: TXP Pharma GmbH, Stans (CH)

(72) Inventor: Thomas Boesen, Copenhagen O (DK)

(73) Assignee: TXP Pharma GmbH, Hergiswil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/289,562

(22) Filed: Oct. 10, 2016

(65) Prior Publication Data

US 2017/0174738 A1     Jun. 22, 2017

Related U.S. Application Data

(60) Continuation of application No. 14/951,305, filed on Nov. 24, 2015, now Pat. No. 9,486,495, which is a division of application No. 14/058,790, filed on Oct. 21, 2013, now Pat. No. 9,217,023.

(60) Provisional application No. 61/716,032, filed on Oct. 19, 2012.

(51) Int. Cl.
*A61K 38/00* (2006.01)
*C07K 16/00* (2006.01)
*C07K 14/685* (2006.01)

(52) U.S. Cl.
CPC ............ *C07K 14/685* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,166,452 A | 9/1979 | Generales | |
| 4,265,874 A | 5/1981 | Bonsen et al. | |
| 4,356,108 A | 10/1982 | Schwab et al. | |
| 7,169,603 B2 | 1/2007 | Hedley et al. | |
| 9,217,023 B2 | 12/2015 | Boesen | |
| 9,486,495 B2 | 11/2016 | Boesen | |
| 2011/0071088 A1 | 3/2011 | Boesen | |
| 2015/0297671 A1 | 10/2015 | Boesen | |
| 2015/0297672 A1 | 10/2015 | Boesen | |
| 2015/0376254 A1 | 12/2015 | Boesen | |

FOREIGN PATENT DOCUMENTS

| | | |
|---|---|---|
| JP | 2009-505994 A | 2/2009 |
| WO | WO 1996/039161 A1 | 12/1996 |
| WO | WO 1998/027113 A2 | 6/1998 |
| WO | WO 1999/046283 A1 | 9/1999 |
| WO | WO 1999/057148 A1 | 11/1999 |
| WO | WO 2007/008704 A2 | 1/2007 |
| WO | WO 2007/022774 A1 | 3/2007 |
| WO | WO 2014/060606 A1 | 4/2014 |
| WO | WO 2015/162485 A1 | 10/2015 |

OTHER PUBLICATIONS

Botte, D. A. C., et al. "Alpha-melanocyte stimulating hormone ameliorates disease activity in an induced murine lupus-like model." Clinical & Experimental Immunology (2014); 177.2: 381-390.
Bowie, James U., et al. "Deciphering the message in protein sequences: tolerance to amino acid substitutions." Science (1990); 247.4948: 1306-1310.
Bracci, Luisa, et al. "Synthetic peptides in the form of dendrimers become resistant to protease activity." Journal of Biological Chemistry (2003); 278.47: 46590-46595.
Cai et al., "Novel 3D pharmacophore of α-MSH/γ-MSH hybrids leads to selective human MC1R and MC3R analogues." Journal of Medicinal Chemistry (2005), 48(6): 1839-1848.
Catania, A., "The Melanocortin System in Control of Inflammation." The Scientific World Journal (2010), 14(10): 1840-1853.
Catania, A., "The melanocortin system in leukocyte biology." Journal of Leukocyte Biology (2007), 81(2): 383-392.
Doi et al., "AP214, an analogue of alpha-melanocyte-stimulating hormone, ameliorates sepsis-induced acute kidney injury and mortality," Kidney International (2008), 73: 1266-1274; advance online publication, Mar. 19, 2008.
EP 13189492.5, Extended European Search Report dated Jan. 17, 2014, 5 pages.
EP 15157262.5, Extended European Search Report dated Aug. 19, 2015, 6 pages.
EP 13189492 Office Action dated Feb. 21, 2014.
Gong, R., "Leveraging melanocortin pathways to treat glomerular diseases." Advances in Chronic Kidney Disease (2014), 21(2): 134-151.
Gong, R., "The renaissance of corticotropin therapy in proteinuric nephropathies." Nature Reviews Nephrology (2011), 8(2):122-128.
Grieco, "D-Amino acid scan of gamma-melanocyte-stimulating hormone: importance of Trp(8) on human MC3 receptor selectivity." Journal of Medicinal Chemistry (2000), 43(26): 4998-5002 (2000).
Haskell-Luevano et al., "Biological and conformational examination of stereochemical modifications using the template melanotropin peptide, Ac-Nle-c[Asp-His-Phe-Arg-Trp-Ala-Lys]-NH2, on human melanocortin receptors." J. Med. Chem. (1997), 40: 1738-1748.
Higuchi et al., "Pro-drugs as novel drug delivery systems." [TOC only] ACS Symposium Series, vol. 14; American Chemical Society, Washington, DC (1975).
Holder et al., "Melanocortin ligands: 30 years of structure-activity relationship (SAR) studies." Med Res Rev. (2004), 24(3): 325-356.
Hunt et al., "Alpha-Melanocyte stimulating hormone and its analogue Nle4DPhe7a-MSH affect morphology, tyrosinase activity and melanogenesis in cultured human melanocytes." Journal of Cell Science (1994), 107: 205-211. Retrieved from URL:<http://jcs.biologists.org/content/107/1/205.full.pdf>.
International Preliminary Report on Patentability for International Application No. PCT/IB2015/000553, dated Oct. 25, 2016, 7 pages.

(Continued)

*Primary Examiner* — Jeanette Lieb

(57) ABSTRACT

The present invention provides peptide analogs of α-MSH and γ-MSH, comprising the amino acid sequence of human α-MSH or γ-MSH, or variants thereof, and having a branched amino acid probe in the N-terminal part of the peptide.

16 Claims, 7 Drawing Sheets

(56) References Cited

OTHER PUBLICATIONS

International Search Report and Written Opinion for International Application No. PCT/IB2015/000553, dated Oct. 8, 2015, 11 pages.
Luger and Brzoska. "α-MSH related peptides: a new class of anti-inflammatory and immunomodulating drugs." Ann. Rheum Dis. 66(Suppl III):iii52-iii55.
March et al., "March's advanced organic chemistry, 5th Ed." [TOC only] John Wiley & Sons. (2001).
Montero-Melendez et al., "The melanocortin agonist AP214 exerts antiinflammatory and proresolvinq properties." The American Journal of Pathology (2011); 179(1): 259-269.
Ngo, J. Thomas, et al. "Computational complexity, protein structure prediction, and the Levinthal paradox." The protein folding problem and tertiary structure prediction. Merz et al., eds, Birkhäuser Boston (19940; pp. 433-506.
PCT Application No. PCT/EP2013/071935, International Preliminary Report on Patentability dated Jan. 21, 2015, 11 pages.
PCT Application No. PCT/EP2013/071935, International Search Report dated Dec. 20, 2013.
PCT Application No. PCT/EP2013/071935, Written Opinion dated Dec. 20, 2013, 6 pages.
Rinne, Petteri, et al. "Pharmacological activation of the melanocortin system limits plaque inflammation and ameliorates vascular dysfunction in atherosclerotic mice." Arteriosclerosis, Thrombosis, and Vascular Biology (2014); 34.7: 1346-1354.
Roche, "Bioreversible carriers in drug design." [TOC only] New York: Pergamon Press (1987).
Steinbruchel et al., "Safety, pharmacokinetics and efficacy of AP214, a novel melanocortin receptor agonist, in patients undergoing cardiac surgery on cadiopulmonary bypass." Abstract TH-P0363, American Society of Nephrology Meeting, Nov. 2011; J Am Soc Nephrol. 22: 2011, p. 196A.

U.S. Appl. No. 14/693,822, Office Action dated Jul. 6, 2016, 19 pages.
U.S. Appl. No. 14/058,790, Notice of Allowance dated Aug. 14, 2015, 8 pages.
U.S. Appl. No. 14/058,790, Office Action dated Apr. 9, 2015, 7 pages.
U.S. Appl. No. 14/951,305, Notice of Allowance dated Jul. 15, 2016, 8 pages.
Wang, De-an, et al. "A single amino acid determines lysophospholipid specificity of the S1P1 (EDG1) and LPA1 (EDG2) phospholipid growth factor receptors." Journal of Biological Chemistry (2001); 276.52: 49213-49220.
Wells, James A. "Additivity of mutational effects in proteins." Biochemistry (1990); 29.37: 8509-8517.
Except for the Cite Nos. referred to above, copies of the publications listed on the attached Form PTO/SB/08 are not being provided pursuant to 37 C.F.R. § 1.98(d) because the publications were previously cited by or submitted to the Office in prior U.S. Appl. No. 14/951,305 (U.S. Pat. No. 9,486,495) to which the above-identified application claims priority under 35 U.S.C. §120.
U.S. Appl. No. 14/693,796 (abandoned).
U.S. Appl. No. 14/693,810 (pending).
U.S. Appl. No. 14/693,822 (pending).
Raposinho et al., "A 99mTc(CO)3-labeled pyrazolyl-α-melanocyte-stimulating hormone analog conjugate for melanoma targeting," Nuclear Medicine and Biology 35 (2008) 91-99.
Bard, David R. "Potential imaging agents for melanoma based on an active analogue of α-melanocyte-stimulating hormone." Drug Delivery (1995); 2.1 : 73-80.
Mima and Shigeno, "Lipocortin-1 Fails to Ameliorate Ischemic Brain Edema in the Cat." Acta Neurochir (2000); 76: 303-306.
UniProtKB-P04083 (ANXA 1_HUMAN), pp. 1-19; www.uniprot.org/uniprot/P04083#ptm_processing; accessed Apr. 29, 2017; pp. 1-19.
U.S. Appl. No. 14/693,810, Office Action dated May 4, 2017, 22 pages.

SEQUENCE LISTING

<160> NUMBER OF SEQ ID NOS: 22

<210> SEQ ID NO 1
<211> LENGTH: 13
<212> TYPE: PRT
<213> ORGANISM: Homo sapiens

```
<400> SEQUENCE: 1

Ser Tyr Ser Met Glu His Phe Arg Trp Gly Lys Pro Val
1               5                   10

<210> SEQ ID NO 2
<211> LENGTH: 13
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: AMIDATION

<400> SEQUENCE: 2

Ser Tyr Ser Met Glu His Phe Arg Trp Gly Lys Pro Val
1               5                   10

<210> SEQ ID NO 3
<211> LENGTH: 13
<212> TYPE: PRT
<213> ORGANISM: Homo sapiens
<220> FEATURE:
<221> NAME/KEY: MUTAGEN
<222> LOCATION: (4)..(4)
<223> OTHER INFORMATION: Nle (norleucine)

<400> SEQUENCE: 3

Ser Tyr Ser Xaa Glu His Phe Arg Trp Gly Lys Pro Val
1               5                   10

<210> SEQ ID NO 4
<211> LENGTH: 13
<212> TYPE: PRT
<213> ORGANISM: Homo sapiens
<220> FEATURE:
<221> NAME/KEY: Nle
<222> LOCATION: (4)..(4)
<223> OTHER INFORMATION: Norleucine
<220> FEATURE:
<221> NAME/KEY: MUTAGEN
<222> LOCATION: (4)..(4)
<220> FEATURE:
<221> NAME/KEY: MOD_RES
<222> LOCATION: (13)..(13)
<223> OTHER INFORMATION: AMIDATION

<400> SEQUENCE: 4

Ser Tyr Ser Xaa Glu His Phe Arg Trp Gly Lys Pro Val
1               5                   10

<210> SEQ ID NO 5
<211> LENGTH: 13
<212> TYPE: PRT
<213> ORGANISM: Homo sapiens

<400> SEQUENCE: 5

Ser Ser Ile Ile Ser His Phe Arg Trp Gly Lys Pro Val
1               5                   10

<210> SEQ ID NO 6
<211> LENGTH: 13
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: AMIDATION

<400> SEQUENCE: 6
```

```
Ser Ser Ile Ile Ser His Phe Arg Trp Gly Lys Pro Val
1               5                   10
```

<210> SEQ ID NO 7
<211> LENGTH: 12
<212> TYPE: PRT
<213> ORGANISM: Homo sapiens

<400> SEQUENCE: 7

```
Tyr Val Met Gly His Phe Arg Trp Asp Arg Phe Gly
1               5                   10
```

<210> SEQ ID NO 8
<211> LENGTH: 12
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: AMIDATION

<400> SEQUENCE: 8

```
Tyr Val Met Gly His Phe Arg Trp Asp Arg Phe Gly
1               5                   10
```

<210> SEQ ID NO 9
<211> LENGTH: 12
<212> TYPE: PRT
<213> ORGANISM: Homo sapiens
<220> FEATURE:
<221> NAME/KEY: MUTAGEN
<222> LOCATION: (3)..(3)
<223> OTHER INFORMATION: Nle (norleucine)

<400> SEQUENCE: 9

```
Tyr Val Xaa Gly His Phe Arg Trp Asp Arg Phe Gly
1               5                   10
```

<210> SEQ ID NO 10
<211> LENGTH: 12
<212> TYPE: PRT
<213> ORGANISM: Homo sapiens
<220> FEATURE:
<221> NAME/KEY: MUTAGEN
<222> LOCATION: (3)..(3)
<223> OTHER INFORMATION: Nle (norleucine)
<220> FEATURE:
<221> NAME/KEY: MOD_RES
<222> LOCATION: (12)..(12)
<223> OTHER INFORMATION: AMIDATION

<400> SEQUENCE: 10

```
Tyr Val Xaa Gly His Phe Arg Trp Asp Arg Phe Gly
1               5                   10
```

<210> SEQ ID NO 11
<211> LENGTH: 11
<212> TYPE: PRT
<213> ORGANISM: Homo sapiens

<400> SEQUENCE: 11

```
Tyr Val Met Gly His Phe Arg Trp Asp Arg Phe
1               5                   10
```

<210> SEQ ID NO 12
<211> LENGTH: 11
<212> TYPE: PRT

```
<213> ORGANISM: Homo sapiens
<220> FEATURE:
<221> NAME/KEY: MOD_RES
<222> LOCATION: (11)..(11)
<223> OTHER INFORMATION: AMIDATION

<400> SEQUENCE: 12

Tyr Val Met Gly His Phe Arg Trp Asp Arg Phe
1               5                   10

<210> SEQ ID NO 13
<211> LENGTH: 11
<212> TYPE: PRT
<213> ORGANISM: Homo sapiens
<220> FEATURE:
<221> NAME/KEY: MUTAGEN
<222> LOCATION: (3)..(3)
<223> OTHER INFORMATION: Nle (norleucine)

<400> SEQUENCE: 13

Tyr Val Xaa Gly His Phe Arg Trp Asp Arg Phe
1               5                   10

<210> SEQ ID NO 14
<211> LENGTH: 11
<212> TYPE: PRT
<213> ORGANISM: Homo sapiens
<220> FEATURE:
<221> NAME/KEY: MUTAGEN
<222> LOCATION: (3)..(3)
<223> OTHER INFORMATION: Nle (norleucine)
<220> FEATURE:
<221> NAME/KEY: MOD_RES
<222> LOCATION: (11)..(11)
<223> OTHER INFORMATION: AMIDATION

<400> SEQUENCE: 14

Tyr Val Xaa Gly His Phe Arg Trp Asp Arg Phe
1               5                   10

<210> SEQ ID NO 15
<211> LENGTH: 6
<212> TYPE: PRT
<213> ORGANISM: Homo sapiens

<400> SEQUENCE: 15

Arg Tyr Tyr Arg Trp Lys
1               5

<210> SEQ ID NO 16
<211> LENGTH: 4
<212> TYPE: PRT
<213> ORGANISM: Homo sapiens

<400> SEQUENCE: 16

His Phe Arg Trp
1

<210> SEQ ID NO 17
<211> LENGTH: 5
<212> TYPE: PRT
<213> ORGANISM: Homo sapiens

<400> SEQUENCE: 17

Ser Tyr Ser Met Glu
1               5
```

```
<210> SEQ ID NO 18
<211> LENGTH: 5
<212> TYPE: PRT
<213> ORGANISM: Homo sapiens
<220> FEATURE:
<221> NAME/KEY: MUTAGEN
<222> LOCATION: (4)..(4)
<223> OTHER INFORMATION: Nle (norleucine)

<400> SEQUENCE: 18

Ser Tyr Ser Xaa Glu
1               5

<210> SEQ ID NO 19
<211> LENGTH: 5
<212> TYPE: PRT
<213> ORGANISM: Homo sapiens

<400> SEQUENCE: 19

Ser Ser Ile Ile Ser
1               5

<210> SEQ ID NO 20
<211> LENGTH: 4
<212> TYPE: PRT
<213> ORGANISM: Homo sapiens

<400> SEQUENCE: 20

Tyr Val Met Gly
1

<210> SEQ ID NO 21
<211> LENGTH: 4
<212> TYPE: PRT
<213> ORGANISM: Homo sapiens
<220> FEATURE:
<221> NAME/KEY: MUTAGEN
<222> LOCATION: (3)..(3)
<223> OTHER INFORMATION: Nle (norleucine)

<400> SEQUENCE: 21

Tyr Val Xaa Gly
1

<210> SEQ ID NO 22
<211> LENGTH: 4
<212> TYPE: PRT
<213> ORGANISM: Homo sapiens

<400> SEQUENCE: 22

Lys Lys Lys Lys
1
```

ALPHA- AND GAMMA-MSH ANALOGUES

CROSS REFERENCE TO RELATED APPLICATIONS

This application is a continuation of U.S. patent application Ser. No. 14/951,305, filed Nov. 24, 2015, now issued as U.S. Pat. No. 9,486,495, which is a divisional of U.S. patent application Ser. No. 14/058,790, filed on Oct. 21, 2013, now issued as U.S. Pat. No. 9,217,023, which claims priority to U.S. Provisional Patent Application No. 61/716,032, filed on Oct. 19, 2012. These applications are incorporated herein by reference in their entireties.

FIELD OF INVENTION

The present invention relates to peptide analogues of the natural existing or native melanocortins α-melanocyte-stimulating hormone (α-MSH) and γ-melanocyte-stimulating hormone (γ-MSH), or variants thereof, and their use in the treatment of inflammatory and/or ischemic conditions.

BACKGROUND OF INVENTION

The native peptides α-melanocyte-stimulating hormone (α-MSH) and γ-melanocyte-stimulating hormone (γ-MSH) each are known as the native agonist for the type 1 (MC1r), the type 3 (MC3r), the type 4 (MC4r) and the type 5 (MC5r) melanocortin receptors (MCr's). The MCr's belong to the class of G-protein coupled receptors. All receptor subtypes are coupled to a G-stimulatory protein, which means that receptor stimulation involves increased production of cAMP. Adrenocorticotropic hormone (ACTH) is the native ligand to the type 2 receptor (MC2r).

The type 1 (MC1r) and/or type 3 (MC3r) melanocortin receptors are expressed in immune competent cells including monocytes, macrophages, neutrophils, t-cells and dendritic cells. Stimulation of the MCr1 and/or MC3r is associated with modulation of an inflammatory response including attenuation of cytokine production and activation of pro-resolving effects.

The selectivity for the MCr's to bind different MSH peptides varies; α-MSH binds with high affinity to the MC1r and with somewhat lesser affinity to the MC3r, MC4r, and MCr5. The binding affinity of γ-MSH against the MC1r and MC5r is weak, the binding to the MC4r somewhat better, and yet higher affinity to the MC3r (J. Med. Chem. 2005, 48, 1839-1848). The MC2r has been reported only to bind ACTH, but none of the MSH peptides. Consequently α-MSH can be considered as a pan MCr agonist, whereas γ-MSH shows selectivity against the MC3r.

Both hypoxia (ischemia) and reperfusion injuries are important factors in human pathophysiology. Examples of tissue hypoxia that predispose to injury during reperfusion include circulatory shock, myocardial ischemia, stroke, temporary renal ischemia, major surgery and organ-transplantation. Because diseases due to ischemia are exceedingly common causes of morbidity and mortality and because organ transplantation is increasingly frequent, treatment strategies with the potential of limiting reperfusion injuries is of great need in order to improve public health.

The underlying pathophysiology of ischemia/reperfusion injuries is complex and involves not only a classical inflammatory reperfusion response with neutrophil-infiltration, but also cytokine gene expression including tumor necrosis factor-α (TNF-α), interleukin (IL)-1β, IL-6, IL-8, interferon-γ, and intercellular adhesion molecule-1 (ICAM-1) within the reperfusion tissue/organ. Furthermore, it has been suggested that locally produced TNF-α contributes to post-ischemic organ dysfunction as in the post-infarctional heart by direct depression of contractility and induction of apoptosis.

Because of the complex nature of ischemia and/or reperfusion injuries simple anti-inflammatory treatment concepts have been shown ineffective. Most experimental studies therefore point to the fact that concomitant interaction with more than one of the activated pathways is needed in order to protect against reperfusion injuries.

Melanocortins have been shown to have both anti-inflammatory, anti-oxidative and anti-apoptotic abilities, and to stimulate pro-resolving effects such as the macrophages ability to phagocytise apoptotic neutrophils. Treatment with the native hormones or known analogues thereof has shown some beneficial effects in animal models of ischemia/reperfusion and inflammatory induced organ failure. Known analogues of MSH include one or two amino acids in the D-conformation (D-stereoisomer), and N-terminal addition of a structural inducing probe (SIP) consisting of e.g. 6 linear Lysine residues ($Lys_6$).

SUMMARY OF INVENTION

The present invention provides peptide analogues of α-MSH and γ-MSH comprising the amino acid sequence of human α-MSH or γ-MSH, or specified variants thereof, in the C-terminal part of the peptide, and a branched amino acid probe (BAP) in the N-terminal part of the peptide. These are collectively referred to herein as α-MSH or γ-MSH analogues.

In one embodiment the peptides according to the present invention have one or more improved properties, for example with respect to binding and/or activation of one or more of the melanocortin receptors, such as MC1r and/or MC3r.

In some embodiments, the MSH analogues provided herein have one or more improved properties compared to the native peptide. For example, in some embodiments, the MSH analogues provided herein have improved binding to one or more of the melanocortin receptors, such as MC1r and/or MC3r. In some embodiments, the MSH analogues provided herein have improved activation of one ore more of the melanocortin receptors, such as MC1r and/or MC3r.

Thus, the present invention relates to specific peptides comprising a branched amino acid probe or BAP modification in the N-terminal part of the peptide and comprising all or at least part of the amino acid sequence of α-MSH, γ-MSH, or a variant thereof.

It is an aspect of the present invention to provide peptides consisting of from 8 to 22 amino acid residues comprising the amino acid sequence:

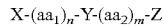

wherein X comprises a branched amino acid probe having a first lysine residue ($Lys_1$) selected from Lys and D-Lys, said first lysine residue being linked by a peptide bond to $(aa_1)_n$, said first lysine residue being optionally linked by peptide bonds to a second lysine residue ($Lys_2$), or to a second and third lysine residue ($Lys_3$), to form a linear chain of a total of 2 or 3 lysine residues selected from Lys and D-Lys, wherein the side chain(s) of one or more of each of said first, second and/or third lysine residues are modified by attaching to the ε-amino group of said one or more of each of said lysine residues a molecule independently selected from the group consisting of $Lys_a$-Lys; $(aa_3)_p$-$Lys_q$; $Lys_q$-$(aa_3)_p$;

[(aa₃)-Lys]$_p$ and [Lys-(aa₃)]$_p$, wherein q is a number selected from 0, 1, 2 and 3; p is a number selected from 1, 2 and 3, and (aa₃) is an amino acid residue independently selected from Arg, His, Gly and Ala, with the proviso that X consists of from 2 to 9 amino acid residues,
wherein Y comprises an amino acid sequence consisting of 4 contiguous amino acid residues selected from the group consisting of His-Phe-Arg-Trp (SEQ ID NO:16); His-(D-Phe)-Arg-Trp; His-Phe-(D-Arg)-Trp; His-Phe-Arg-(D-Trp); His-(D-Phe)-Arg-(D-Trp); His-Nal-Arg-Trp and His-(D-Nal)-Arg-Trp; and
wherein Z comprises an amino acid sequence consisting of 2 or 3 contiguous amino acid residues selected from the group consisting of Lys-Pro-Val; Lys-Pro-(D-Val); Arg-Phe-Gly; Arg-(D-Phe)-Gly; Arg-Phe and Arg-(D-Phe); and
wherein n is a number selected from 0, 1, 2, 3, 4 and 5, and (aa₁) independently can be any natural or unnatural amino acid residue, and wherein m is 0 or 1, and (aa₂) can be any natural or unnatural amino acid residue.

In one embodiment, (aa₁)$_n$ is a sequence consisting of 4 or 5 contiguous amino acids (n=4 or 5), and is selected from the group consisting of Ser-Tyr-Ser-Met-Glu (SEQ ID NO:17), Ser-Tyr-Ser-Nle-Glu (SEQ ID NO:18), Ser-Ser-Ile-Ile-Ser (SEQ ID NO:19), Tyr-Val-Met-Gly (SEQ ID NO:20) and Tyr-Val-Nle-Gly (SEQ ID NO:21).

In one embodiment (aa₂)$_m$ is 1 amino acid (m=1), and is selected from the group consisting of Gly and Asp.

Specific examples of α-MSH analogues and γ-MSH analogues according to the present invention are disclosed herein below.

The α-MSH and γ-MSH analogues of the present invention, having a branched amino acid probe as defined herein, are in a certain embodiment capable of binding to and activating one or both of the melanocortin receptors MC1r and MC3r, in a particular embodiment being a full agonist of one or both of the melanocortin receptors MC1r and MC3r and/or having increased binding affinity to one or both of the melanocortin receptors MC1r and MC3r.

The present invention also encompass pharmaceutical compositions comprising the α-MSH and γ-MSH analogues of the present invention, as well as the α-MSH and γ-MSH analogues of the present invention for use as a medicament.

In one embodiment the α-MSH and γ-MSH analogues according to the present invention are suitable for use in the treatment of an ischemic and/or inflammatory condition in the tissue of one or more organs of a mammal. In some embodiments, said treatment is prophylactic, ameliorative or curative.

In some embodiments said ischemic condition(s) concerned is due to or caused by one or more underlying conditions such as stroke, injury, septic shock, systemic hypotension, cardiac arrest due to heart attack, cardiac arrhythmia, atheromatous disease with thrombosis, embolism from the heart or from blood vessel from any organ, vasospasm, aortic aneurysm or aneurisms in other organs, coronary stenosis, myocardial Infarction, angina pectoris, pericarditis, myocarditis, myxodemia, or endocarditis.

Further, in some embodiments said ischemic and/or inflammatory condition is associated with surgery, such as major surgery. In some embodiments, said surgery includes cardiothoracic surgery, abdominal surgery, surgery on the aorta and/or other major blood vessels, repair of one or more cardiac valves, cardiac artery bypass grafting (CABG), surgery on the aortic root or the aortic branch including the common carotid arteries, and combined cardiac surgery such as valve(s) replacement and CABG and/or aortic root surgery.

Furthermore, in some embodiments said ischemic and/or inflammatory condition is associated with organ transplantation, such as solid organ transplantation. In some embodiments said organ transplantation includes heart transplantation, lung transplantation, combined heart and lung transplantation, liver transplantation and kidney transplantation.

In one embodiment, said ischemic and/or inflammatory condition is post-surgical systemic inflammatory response syndrome (SIRS) or post-surgical organ dysfunction, including post-surgical renal failure such as acute kidney injury (AKI), neprotoxicity and/or chronic renal failure (CRF).

In one embodiment, said ischemic and/or inflammatory condition is reperfusion injury.

Also, in one embodiment said ischemic and/or inflammatory condition is an inflammatory disease, including but not limited to arthropathy (joint disease), rheumatoid arthritis (RA), gout, inflammatory diseases of the gastrointestinal system, and multiple sclerosis.

DETAILED DESCRIPTION OF THE INVENTION

Figure 1:
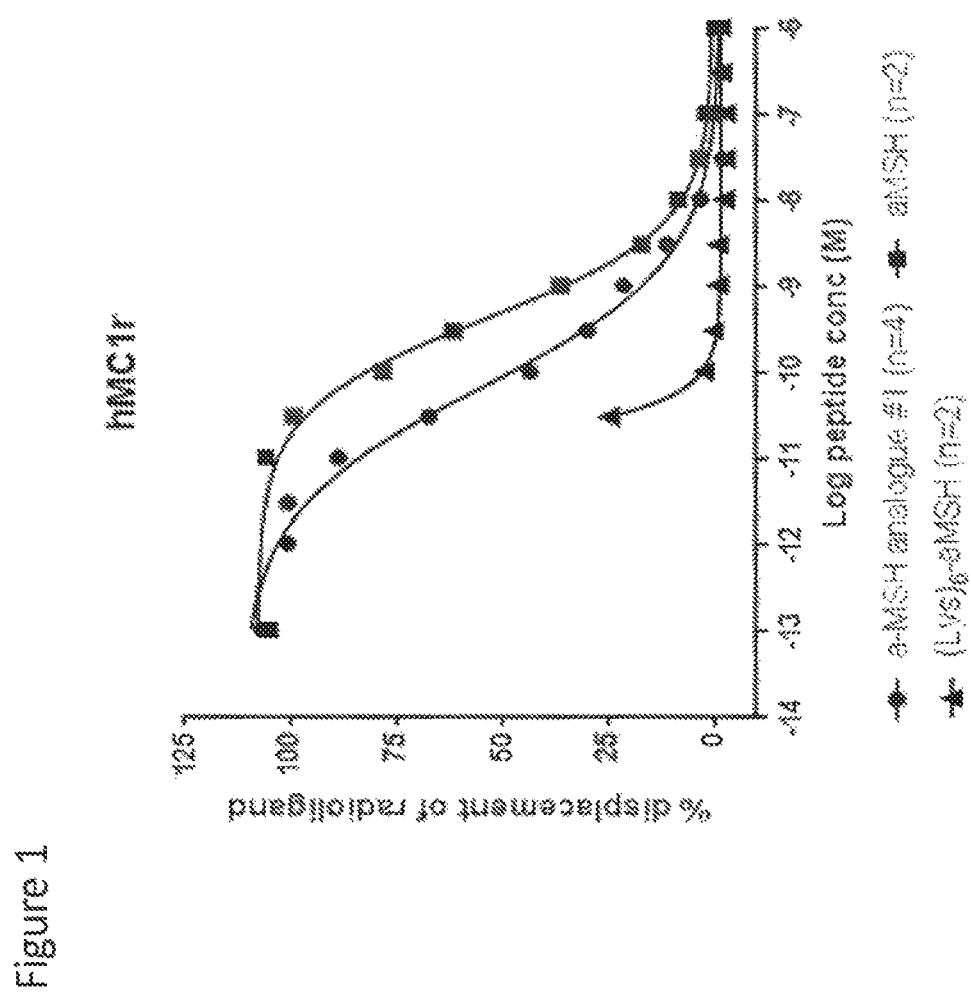
FIG. 1: Binding affinity against the human MC1r of α-MSH analogue #1: Ac-(Ac-Lys-Lys-)Lys-Ser-Tyr-Ser-Met-Glu-His-Phe-Arg-Trp-Gly-Lys-Pro-Val-NH2 (Ac-(Ac-Lys-Lys-)Lys- SEQ ID NO:2), α-MSH and Ac(Lys)₆-αMSH (See Example 1).

Proopiomelanocortin (POMC) is a precursor polypeptide having 241 amino acid residues. POMC is synthesized from the 285-amino acid long polypeptide precursor, pre-pro-opiomelanocortin (pre-POMC), by the removal of a 44-amino acid long signal peptide sequence during translation. POMC undergoes extensive, tissue-specific, post-translational processing via cleavage by subtilisin-like enzymes known as prohormone convertases. There are at least eight potential cleavage sites within the polypeptide precursor and, depending on tissue type and the available convertases, processing may yield as many as ten biologically active peptides involved in diverse cellular functions.

POMC can be cleaved enzymatically into the following peptides: N-terminal peptide of proopiomelanocortin (NPP, or pro-γ-MSH), γ-melanocyte-stimulating hormone or γ-melanotropin (γ-MSH), adrenocorticotropic hormone (ACTH) or corticotropin, α-melanocyte-stimulating hormone or α-melanotropin (α-MSH), corticotropin-like intermediate peptide (CLIP), β-lipotropin (ρ-LPH), γ-lipotropin (γ-LPH), β-melanocyte-stimulating hormone or β-melanotropin (β-MSH), β-endorphin and [Met]enkephalin.

Three forms of γ-MSH exist namely γ1-MSH, γ2-MSH and γ3-MSH, which differ in the structure of their C-termini. γ1-MSH and γ2-MSH vary by only one amino acid in the C-terminus.

The melanocortins include ACTH and the different forms of melanocyte-stimulating hormone (MSH) (alpha, beta and gamma). They exert their effects by binding to and activating the melanocortin receptors MC1r to MC5r, each with differing specificities for the melanocortins.

Naturally occurring or native melanocyte-stimulating hormones (the α, γ1 and γ2 forms) have the following amino acid sequences:

```
a-MSH
Ac-Ser-Tyr-Ser-Mer-Glu-His-Phe-Arg-Trp-Gly-Lys-Pro-
Val(Ac-SEQ ID NO: 1)
SYSMEHFRWGKPV
P01189[138-150], Pro-opiomelanocortin, Homo sapiens
aa modification: Valine amide (pos 150) = SEQ ID NO: 2 y1-MSH
Try-Val-Met-Gly-His-Phe-Arg-Trp-Asp-Arg-Phe-Gly
                                              (SEQ ID NO: 7)
YVMGHFRWDRFG
P01189[77-88], Pro-opiomelanocortin, Homo sapiens
aa modifications: Phenylalanine amind (pos 88) = SEQ ID NO: 8 y2-MSH
Try-Val-Met-Gly-His-Phe-Arg-Trp-Asp-Arg-Phe-Gly
                                              (SEQ ID NO: 11)
YVMGHFRWDRF
P01189[77-87], Pro--opiomelanocortin, Homo sapiens
aa modifications: Phenylalanine aminde (pos 87) = SEQ ID NO: 12
```

Analogues of Melanocyte-Stimulating Hormone (MSH)

It is an aspect of the present invention to provide peptide analogues of α-MSH and γ-MSH. The peptides comprise the amino acid sequence of human α-MSH or γ-MSH, or specified variants thereof, in the C-terminal part of the peptide, and a branched amino acid probe (BAP) in the N-terminal part of the peptide, and are collectively referred to as α-MSH or γ-MSH analogues. In some embodiments the MSH sequence and the BAP are covalently linked together by a peptide bond.

In some embodiments, the peptides provided herein have certain improved properties, for instance with respect to binding affinity and/or activation of one or both of the melanocortin receptor MC1r and/or MC3r. Still further, in another embodiment, the peptides provided herein are more stable, such as less susceptible to proteases.

Thus, in one aspect the present invention relates to a peptide consisting of from 8 to 22 amino acid residues comprising the amino acid sequence:

X-(aa$_1$)$_n$-Y-(aa$_1$)$_m$-Z wherein X comprises or consists of a branched amino acid probe having a first lysine residue selected from Lys and D-Lys, said first lysine residue being linked by a peptide bond to (aa$_1$)$_n$, said first lysine residue being optionally linked by peptide bonds to a second lysine residue, or to a second and third lysine residue, to optionally form a linear chain of a total of 2 or 3 lysine residues selected from Lys and D-Lys, wherein the side chain(s) of one or more of each of said first, second and/or third lysine residues are modified by attaching to the ε-amino group of said one or more of each of said lysine residues a molecule independently selected from the group consisting of Lys$_q$-Lys; (aa$_3$)$_p$-Lys$_q$; Lys$_q$-(aa$_3$)$_p$; [(aa$_3$)-Lys]$_p$ and [Lys-(aa$_3$)]$_p$, wherein q is a number selected from 0, 1, 2 and 3; p is a number selected from 1, 2 and 3, and (aa$_3$) is an amino acid residue independently selected from Arg, His, Gly and Ala, with the proviso that X consists of from 2 to 9 amino acid residues, wherein Y comprises an amino acid sequence consisting of 4 contiguous amino acid residues selected from the group consisting of His-Phe-Arg-Trp (SEQ ID NO:16); His-(D-Phe)-Arg-Trp; His-Phe-(D-Arg)-Trp; His-Phe-Arg-(D-Trp); His-(D-Phe)-Arg-(D-Trp); His-Nal-Arg-Trp and His-(D-Nal)-Arg-Trp; and wherein Z comprises an amino acid sequence consisting of 2 or 3 contiguous amino acid residues selected from the group consisting of Lys-Pro-Val; Lys-Pro-(D-Val); Arg-Phe-Gly; Arg-(D-Phe)-Gly; Arg-Phe and Arg-(D-Phe); and wherein n is a number selected from 0, 1, 2, 3, 4 and 5, and (aa$_1$) independently can be any natural or unnatural amino acid residue, and wherein m is 0 or 1, and (aa$_2$) can be any one natural or unnatural amino acid residue.

'-' of the equation 'X-(aa$_1$)$_n$-Y-(aa$_2$)$_m$-Z' is a peptide bond.

The term "said first lysine residue being linked by a peptide bond to (aa$_1$)$_n$" means that the first lysine residue of the BAP is linked by a peptide bond to the most N-terminal amino acid of (aa$_1$)$_n$.

A natural amino acid is a naturally occurring amino acid existing in nature and being naturally incorporated into polypeptides (proteinogenic). They consist of the 20 genetically encoded amino acids Ala, Arg, Asn, Asp, Cys, Gln, Glu, Gly, His, Ile, Leu, Lys, Met, Phe, Pro, Ser, Tyr, Thr, Trp, Val, and 2 which are incorporated into proteins by unique synthetic mechanisms: Sec (selenocysteine, or U) and Pyl (pyrrolysine, O). These are all L-stereoisomers.

Aside from the 22 natural or standard amino acids, there are many other non-naturally occurring amino acids (non-proteinogenic or non-standard). They are either not found in proteins, or are not produced directly and in isolation by standard cellular machinery. Non-standard amino acids are usually formed through modifications to standard amino acids, such as post-translational modifications. Examples of preferred unnatural amino acid residues according to the invention are Nle (Norleucine), Nal (beta-2-naphthyl-alanine), D-Nal (beta-2-naphthyl-D-alanine), D-Arg, D-Trp, D-Phe and D-Val.

Any amino acids according to the present invention may be in the L- or D-configuration. If nothing is specified, reference to the L-isomeric form is preferably meant.

The standard and/or non-standard amino acids may be linked by peptide bonds (to form a linear peptide chain), or by non-peptide bonds (e.g. via the variable side-chains of the amino acids).

The term peptide also embraces post-translational modifications introduced by chemical or enzyme-catalyzed reactions, as are known in the art. Such post-translational modifications can be introduced prior to partitioning, if desired. Also, functional equivalents may comprise chemical modifications such as ubiquitination, labeling (e.g., with radionuclides, various enzymes, etc.), pegylation (derivatization with polyethylene glycol), or by insertion (or substitution by chemical synthesis) of amino acids (amino acids) such as ornithine, which do not normally occur in human proteins.

Sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of e.g a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same molecules, including dimers or unrelated chemical moieties. Such functional equivalents are prepared by linkage of functionalities to groups which are found in fragment including at any one or both of the N- and C-termini, by means known in the art.

In some embodiments, the peptides according to the present invention are modified by N-terminal acetylation of the most N-terminal amino acid of the MSH peptide, or any residues comprised in the branched X. In some embodiments the peptides according to the present invention are modified by C-terminal amidation. In one embodiment such modification increases the stability of the peptides.

In one embodiment, the carboxy terminus of said peptide or MSH-analogue as defined herein above is —C(=O)—B1, wherein B1 is selected from OH, NH$_2$. NHB2, N(B2)(B3), OB2, and B2, and wherein B2 and B3 are independently selected from optionally substituted C$_{1-6}$ alkyl, optionally substituted C$_{7-16}$ alkenyl, optionally substituted C$_{1-6}$ aryl, optionally substituted C$_{7-16}$ aralkyl, and optionally substituted C$_{7-16}$ alkylaryl.

In a specific embodiment, the carboxy terminus of said peptide is —C(=O)—B1, wherein B1 is OH or NH$_2$.

In one embodiment, the amino terminus of said peptide is (B4)HN—, (B4)(B5)N—, or (B6)HN—, wherein 84 and B5 are independently selected from H, optionally substituted C$_{1-6}$ alkyl, optionally substituted C$_{2-6}$ alkenyl, optionally substituted C$_{6-10}$ aryl, optionally substituted C$_{7-16}$ aralkyl, and optionally substituted C$_{7-16}$ alkylaryl; and B6 is B4-C(=O)—.

In another embodiment the amino terminus of said peptide is (B6)HN—, wherein B6 is B4-C(=O)— and B4 is CH$_3$. In yet another embodiment the amino terminus of said peptide is (B4)HN—, wherein B4 is H.

According to the present invention, the term "optionally substituted" is intended to mean that the group in question may be substituted one or several times, such as 1 to 5 times, preferably 1 to 3 times, most preferably 1 to 2 times, with one or more groups selected from C$_{1-8}$-alkyl, C$_{1-8}$-alkoxy, oxo (which may be represented in the tautomeric enol form), carboxyl, amino, hydroxy (which when present in an enol system may be represented in the tautomeric keto form), nitro, cyano, dihalogen-C$_{1-8}$-alkyl, trihalogen-C$_{1-8}$-alkyl and halogen. In general, the above substituents may be susceptible to further optional substitution.

According to the present invention, the term C$_{1-6}$-alkyl is intended to mean a linear or branched saturated hydrocarbon chain wherein the longest chains has from one to six carbon atoms, such as methyl, ethyl, n-propyl, isopropyl, n-butyl, isobutyl, sec-butyl, tert-butyl, pentyl, isopentyl, neopentyl, hexyl, heptyl and octyl. A branched hydrocarbon chain is intended to mean a C$_{1-6}$-alkyl substituted at any carbon with a hydrocarbon chain.

According to the present invention, the term C$_{2-6}$-alkenyl is intended to mean a linear or branched hydrocarbon group having from two to six carbon atoms and containing one or more double bonds. Illustrative examples of C$_{2-6}$-alkenyl groups include allyl, homo-allyl, vinyl, crotyl, butenyl, pentenyl and hexenyl. Illustrative examples of C$_{2-6}$-alkenyl groups with more than one double bond include butadienyl, pentadienyl, hexadienyl, and hexatrienyl groups as well as branched forms of these. The position of the unsaturation (the double bond) may be at any position along the carbon chain.

According to the present invention, the term C$_{3-8}$-cycloalkyl is intended to cover three-, four-, five-, six- seven-, and eight-membered rings comprising carbon atoms only whereas the term hetero-cyclyl is intended to mean three-, four-, five-, six- seven-, and eight-membered rings wherein carbon atoms together with from 1 to 3 heteroatoms constitute said ring. The heteroatoms are independently selected from oxygen, sulphur, and nitrogen. C$_{3-8}$-cycloalkyl and heterocyclyl rings may optionally contain one or more unsaturated bonds.

Illustrative examples of C$_{3-8}$-cycloalkyl are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, cycloheptene, 1,2-cycloheptadiene, 1,3-cycloheptadiene, 1,4-cycloheptadiene and 1,3,5 cycloheptatriene.

Illustrative examples of heterocyclyls are the heterocycles 2H-thipyran, 3H-thipyran, 4H-thipyran, tetrahydrothiopyran, 2H-pyran, 4H-pyran, tetrahydropyran, piperidine, 1.2-dithiin, 1,2-dithiane, 1,3-dithiin, 1,3-dithiane, 1,4-dithiin, 1,4-dithiane, 1,2-dioxin, 1,2-dioxane, 1,3-dioxin, 1,3-dioxane, 1,4-dioxin, 1,4-dioxane, piperazine, 1,2-oxathiin, 1,2-oxathiane, 4H-1,3-oxathiin, 1,3-oxathiane, 1,4-oxathiin, 1,4-oxathiane, 2H-1,2-thiazine, tetrahydro-1,2-thiazine, 2H-1,3-thiazine, 4H-1,3-thiazine, 5,6-dihydro-4H-thiazine, 4H-1,4-thiazine, tetrahydro-1,4-thiazine, 2H-1,2-oxazine, 4H-1,2-oxazine, 6H-1,2-oxazine, 2H-1,3-oxazine, 4H-1,3-oxazine, 4H-1, 4-oxazine, maleimide, succinimide, imidazole, pyrazole, pyrrole, oxazole, furazan, barbituric acid, thiobarbituric acid, dioxopiperazine, isoxazole, hydantoin, dihydrouracil, morpholine, trioxane, 4H-1,2,3-trithiin, 1,2,3-trithiane, 1,3,5-trithiane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,2-dioxole, 1,2-dioxolane, 1,3-dioxole, 1,3-dioxolane, 3H-1,2-dithiole, 1,2-dithiolane, 1,3-dithiole, 1,3-dithiolane, isoxazoline, isoxazolidine, oxazoline, oxazolidine, thiazoline, thiozolidine, 3H-1,2-oxathiole, 1,2-oxathiolane, 5H-1,2-oxathiole, 1,3-oxathiole, 1,3-oxathiolane, 1,2,3-trithiole, 1,2,3-trithiolane, 1,2,4-trithiolane, 1,2,3-trioxole, 1,2,3-trioxolane, 1,2,4-trioxolane, 1,2,3-triazoline and 1,2,3-triazolidine. Binding to the heterocycle may be at the position of the heteroatom or via carbon atom of the heterocycle.

According to the present invention the term aryl is intended to mean a carbocyclic aromatic ring or ring system. Moreover, the term aryl includes fused ring systems wherein at least two aryl rings, or at least one aryl and at least one $C_{3-6}$-cycloalkyl, or at least one aryl and at least one heterocyclyl, share at least chemical bond. Illustrative examples of aryl rings include optionally substituted phenyl, naphthalenyl, phenanthrenyl, anthracenyl, acenaphthylenyl, tetralinyl, fluorenyl, indenyl, indolyl, coumaranyl, coumarinyl, chromanyl, isochromanyl, and azulenyl. A preferred aryl group is phenyl.

$C_{7-16}$ aralkyl is intended to mean a $C_{6-10}$ aryl substituted with $C_{1-6}$ alkyl and $C_{7-16}$ alkylaryl is intended to mean a $C_{1-6}$ alkyl substituted with $C_{6-10}$ aryl.

Embodiments of Y

As defined herein above, Y of the equation X-$(aa_1)_n$-Y-$(aa_2)_m$-Z is a sequence consisting of 4 amino acid residues selected from the group consisting of His-Phe-Arg-Trp (SEQ ID NO:16), His-(D-Phe)-Arg-Trp, His-Phe-(D-Arg)-Trp, His-Phe-Arg-(D-Trp), His-(D-Phe)-Arg-(D-Trp), His-Nal-Arg-Trp and His-(D-Nal)-Arg-Trp.

It follows that Y may be an amino acid sequence corresponding to the native part of the α- or γ-MSH, or variants thereof. The native part of α-MSH in this respect would be His-Phe-Arg-Trp (SEQ ID NO:16), and the native part of γ-MSH in this respect would also be His-Phe-Arg-Trp (SEQ ID NO:16).

In one particular embodiment, Y is His-Phe-Arg-Trp (SEQ ID NO:16). In another particular embodiment, Y is His-(D-Phe)-Arg-Trp. In yet another particular embodiment, Y is His-Phe-(D-Arg)-Trp. In another embodiment, Y is His-Phe-Arg-(D-Trp). In another embodiment, Y is His-(D-Phe)-Arg-(D-Trp). In another embodiment, Y is His-Nal-Arg-Trp. In another embodiment, Y is His-(D-Nal)-Arg-Trp.

Embodiments of Z

As defined herein above, Z of the equation X-$(aa_1)_n$-Y-$(aa_2)_m$-Z is a sequence consisting of 2 or 3 contiguous amino acid residues selected from the group consisting of Lys-Pro-Val; Lys-Pro-(D-Val); Arg-Phe-Gly; Arg-(D-Phe)-Gly, Arg-Phe and Arg-(D-Phe).

It follows that Z may be an amino acid sequence corresponding to the native part of the α- or γ-MSH, or variants thereof. The native part of α-MSH in this respect would be Lys-Pro-Val, and the native part of γ-MSH in this respect would Arg-Phe-Gly (γ1-MSH) or Arg-Phe (γ2-MSH).

In one particular embodiment, Z is Lys-Pro-Val or Lys-Pro-(D-Val). In another particular embodiment, Z is Arg-Phe-Gly or Arg-(D-Phe)-Gly. In yet another particular embodiment, Z is Arg-Phe or Arg-(D-Phe).

In a particular embodiment, the most carboxy terminal amino acid may be amidated (—$NH_2$; —$CONH_2$). Thus, in one embodiment, Val or (D-Val) is a Valine amide. In another embodiment, Phe or (D-Phe) is a Phenylalanine amide. In yet another embodiment, Gly is Glycine amide.

Embodiments of $(aa_1)_n$

As defined herein above, $(aa_1)_n$ of the equation X-$(aa_1)_n$-Y-$(aa_2)_m$-Z is a sequence consisting of from 0 to 5 amino acids (n=0, 1, 2, 3, 4, or 5). It follows that $(aa_1)_n$ may consist of 0 amino acids, or consist of from 1 to 2, such as 2 to 3, for example 3 to 4, such as 4 to 5 contiguous amino acid residues.

In a particular embodiment, $(aa_1)_n$ is a sequence consisting of 4 or 5 contiguous amino acids (n=4 or 5).

In a particular embodiment, $(aa_1)_n$ may be an amino acid sequence corresponding to the native part of the α- or γ-MSH, or variants thereof. The native part of α-MSH in this respect would be Ac-Ser-Tyr-Ser-Met-Glu (Ac-SEQ ID NO:17), and the native part of γ-MSH in this respect would be Tyr-Val-Met-Gly (SEQ ID NO:20).

In a particular embodiment, $(aa_1)_n$ is selected from the group consisting of Ser-Tyr-Ser-Met-Glu (SEQ ID NO:17), Ser-Tyr-Ser-Nle-Glu (SEQ ID NO:18), Ser-Ser-Ile-Ile-Ser (SEQ ID NO:19), Tyr-Val-Met-Gly (SEQ ID NO:20) and Tyr-Val-Nle-Gly (SEQ ID NO:21).

In a particular embodiment when relating to analogues of α-MSH, $(aa_1)_n$ is selected from the group consisting of Ser-Tyr-Ser-Met-Glu (SEQ ID NO:17), Ser-Tyr-Ser-Nle-Glu (SEQ ID NO:18) and Ser-Ser-Ile-Ile-Ser (SEQ ID NO:19); or the group consisting of Ser-Tyr-Ser-Met-Glu (SEQ ID NO:17), and Ser-Tyr-Ser-Nle-Glu (SEQ ID NO:18). In one particular embodiment, $(aa_1)_n$ is Ser-Tyr-Ser-Met-Glu (SEQ ID NO:17).

In a particular embodiment when relating to analogues of γ-MSH, $(aa_1)_n$ is selected from the group consisting of Tyr-Val-Met-Gly (SEQ ID NO:20) and Tyr-Val-Nle-Gly (SEQ ID NO:21). In one particular embodiment, $(aa_1)_n$ is Tyr-Val-Met-Gly (SEQ ID NO:20).

Embodiments of $(aa_2)_m$

As defined herein above, $(aa_2)_m$ of the equation X-$(aa_1)_n$-Y-$(aa_2)_m$-Z is an amino acid residue consisting of 0 or 1 amino acid (m=0 or 1). In one embodiment, $(aa_2)_m$, consist of 1 amino acid (m=1).

In one embodiment $(aa_2)_m$ is an amino acid corresponding to the native part of α- or γ-MSH, or variants thereof. The native part of α-MSH in this respect would be Gly, and the native part of γ-MSH in this respect would be Asp.

It follows that in one embodiment, $(aa_2)_m$ is selected from the group consisting of Gly and Asp. In one particular embodiment $(aa_2)_m$ is Gly. In another particular embodiment $(aa_2)_m$ is Asp.

In one embodiment, $(aa_1)_n$ is selected from the group consisting of Ser-Tyr-Ser-Met-Glu (SEQ ID NO:17), Ac-Ser-Tyr-Ser-Met-Glu (Ac-SEQ ID NO:17), Ser-Tyr-Ser-Nle-Glu (SEQ ID NO:18), Ac-Ser-Tyr-Ser-Nle-Glu (Ac-SEQ ID NO:18), Ser-Ser-Ile-Ile-Ser (SEQ ID NO:19) and Ac-Ser-Ser-Ile-Ile-Ser (Ac-SEQ ID NO:19), and $(aa_2)_m$ is Gly.

In another embodiment, $(aa_1)_n$ is selected from the group consisting of Tyr-Val-Met-Gly (SEQ ID NO:20), Ac-Tyr-Val-Met-Gly (Ac-SEQ ID NO:20), Tyr-Val-Nle-Gly (SEQ ID NO:21) and Ac-Tyr-Val-Nle-Gly (Ac-SEQ ID NO:21), and $(aa_2)_m$ is Asp.

Embodiments of X

As defined herein above, X of the equation X-$(aa_1)_n$-Y-$(aa_2)_m$-Z defines a branched amino acid probe (BAP) being attached or linked to the N-terminus of α- or γ-MSH or variants thereof, said α- or γ-MSH or variants thereof being defined herein as: -$(aa_1)_n$-Y-$(aa_2)_m$-Z.

In one embodiment X is coupled or linked to the most N-terminal amino acid of the sequence -$(aa_1)_n$- by a peptide bond to a first lysine residue selected from Lys and D-Lys. Thus, the first amino acid of X, being connected to -$(aa_1)_n$-, is in one embodiment a lysine residue. Said first lysine residue is in one embodiment acetylated (Ac-Lys). The first lysine residue may in one embodiment be denoted $Lys_1$.

In some embodiments, the most N-terminal amino acid of the sequence -$(aa_1)_n$- is Ser or Tyr. Ser is the most N-terminal amino acid of native α-MSH, and Tyr is the most N-terminal amino acid of native γ-MSH. It follows that in some embodiments, the first lysine residue of X is connected by a peptide bond to either Ser or Tyr. The N-terminal Ser of native α-MSH is acetylated, which acetylation is not present when a BAP or X as defined herein is added to produce the claimed analogues.

X always comprises a first lysine residue. The first lysine residue may in one embodiment be denoted $Lys_1$. In one embodiment said first lysine residue is further linked by a peptide bond to a second lysine residue to form a linear chain of a total of 2 lysine residues selected from Lys and D-Lys. In one embodiment, one or both of each of said first and second lysine residue are acetylated (Ac-Lys). The second lysine residue may in one embodiment be denoted $Lys_2$.

In one embodiment, said first lysine residue is further linked by peptide bonds to a second and a third lysine residue to form a linear chain of a total of 3 lysine residues selected from Lys and D-Lys. In one embodiment, one, two or three of each of said first, second and third lysine residues are acetylated (Ac-Lys). The third lysine residue may in one embodiment be denoted $Lys_3$.

In one embodiment, yhe first, first and second, and/or the first, second and third lysine residues of X are referred to as the lysine backbone of X ($Lys_1$, $Lys_{1-2}$, $Lys_{1-3}$).

In one embodiment, the first lysine residue, or the second lysine residue, or the third lysine residue, or the first and the second lysine residues, or the first and the third lysine residues, or the second and the third lysine residues, or the first, the second and the third lysine residues of the lysine backbone of X are acetylated (Ac-Lys).

It follows that in one embodiment, X comprises a first lysine residue selected from Lys and D-Lys being linked by a peptide bond to $(aa_1)_n$ (i.e. the lysine backbone of X consists of 1 lysine residue). In one embodiment, said first lysine may be aceylated ($COCH_3$).

In another embodiment, X comprises a first and a second lysine residue selected from Lys and D-Lys being linked by peptide bonds to form a linear chain of a total of 2 lysine residues (i.e. the lysine backbone of X consists of 2 lysine residues).

In yet another embodiment, X comprises a first, a second and a third lysine residue selected from Lys and D-Lys being linked by peptide bonds to form a linear chain of a total of 3 lysine residues (i.e. the lysine backbone of X consists of 3 lysine residues). In this setting, it is understood that the first lysine may have the second and third lysine both attached at its amine group or both attached to its carboxylic acid group; or it may have the second lysine attached at its amine group and the third lysine attached at its carboxylic acid group.

It is required that the side chain(s) of one or more of each of said first, second and/or third lysine residues are modified by attaching to the ε-amino group of said one or more of each of said lysine residues a further molecule. Attaching a molecule to the ε-amino group of one or more of each of said lysine residues of the lysine backbone of X renders X branched, cf. the branched amino acid probe (BAP).

In one embodiment, one lysine residue of the lysine backbone of X is modified by attaching a molecule to the ε-amino group. Said one lysine residue of the lysine backbone of X in one embodiment comprises $Lys_1$, $Lys_2$ or $Lys_3$.

In another embodiment, two lysine residues of the lysine backbone of X are modified by attaching a molecule to the ε-amino groups of said two lysine residues. Said two lysine residues of the lysine backbone of X in one embodiment comprise $Lys_1$ and $Lys_2$; $Lys_1$ and $Lys_3$; or $Lys_2$ and $Lys_3$.

In yet another embodiment, three lysine residues of the lysine backbone of X are modified by attaching a molecule to the ε-amino groups of said three lysine residues.

Said three lysine residues of the lysine backbone of X in one embodiment comprise $Lys_1$, $Lys_2$ and $Lys_3$.

It follows that the first lysine residue, or the second lysine residue, or the third lysine residue, or the first and the second lysine residues, or the first and the third lysine residues, or the second and the third lysine residues, or the first, the second and the third lysine residues of the lysine backbone of X each may be modified accordingly.

X in one embodiment consist of a total of from 2 to 9 amino acid residues. Thus, the total number of amino acids constituting the branched amino acid probe (BAP) is in one embodiment 2 to 9; this number including the 1, 2 or 3 lysine residues making up the lysine backbone of X.

In one embodiment, X comprises a branched amino acid probe consisting of from 2 to 3 amino acid residues, such as from 3 to 4 amino acid residues, such as consisting of from 4 to 5 amino acid residues, such as consisting of from 5 to 6 amino acid residues, such as consisting of from 6 to 7 amino acid residues, such as consisting of from 7 to 8 amino acid residues, such as consisting of from 8 to 9 amino acid residues.

In one embodiment, the molecule to be attached to the ε-amino group(s) of the one or more of the lysine residues of X are independently selected from the group consisting of $Lys_q$-Lys; $(aa_3)_p$-$Lys_q$; $Lys_q$-$(aa_3)_p$; [$(aa_3)$-Lys]$_p$ and [Lys-$(aa_3)$]$_p$, wherein q is a number selected from 0, 1, 2 and 3; p is a number selected from 1, 2 and 3, and $(aa_3)$ is an amino acid residue independently selected from Arg, His, Gly and Ala.

It follows that in one embodiment the first lysine residue, or the second lysine residue, or the third lysine residue, or the first and the second lysine residues, or the first and the third lysine residues, or the second and the third lysine residues, or the first, the second and the third lysine residues of X each are modified by attaching to the ε-amino group(s) a molecule independently selected from the group consisting of $Lys_q$-Lys; $(aa_3)_p$-$Lys_q$; $Lys_q$-$(aa_3)_p$; [$(aa_3)$-Lys]$_p$ and [Lys-$(aa_3)$]$_p$, wherein q is a number selected from 0, 1, 2 and 3; p is a number selected from 1, 2 and 3, and $(aa_3)$ is an amino acid residue independently selected from Arg, His, Gly and Ala.

In a particular embodiment, $(aa_3)$ is an amino acid residue independently selected from Gly and Ala. In a further embodiment, $(aa_3)$ is Gly.

In one embodiment, the molecules to be attached to the ε-amino group(s) are further acetylated. It follows that the molecules are in one embodiment independently selected from the group consisting of Ac-$Lys_q$-Lys; Ac-$(aa_3)_p$-$Lys_q$; Ac-$Lys_q$-$(aa_3)_p$; Ac-$[(aa_3)$-Lys$]_p$ and Ac-$[Lys$-$(aa_3)]_p$, and/or $Lys_q$-Lys; $(aa_3)_p$-$Lys_q$; $Lys_q$-$(aa_3)_p$; $[(aa_3)$-Lys$]_p$ and $[Lys$-$(aa_3)]_p$.

In a particular embodiment, the molecule to be attached to the s-amino groups of the one or more lysine residues is $Lys_q$-Lys, wherein q is a number selected from 0, 1, 2 and 3.

It follows that in one embodiment, X comprises a branched amino acid probe consisting of from 2 to 9 lysine residues selected from Lys and D-Lys.

In one embodiment, X comprises a maximum of 1, 2, 3 or 4 amino acids selected from Arg. His, Gly and Ala ($aa_3$), the remaining amino acids of X being selected from Lys and D-Lys. In one embodiment, X comprises a maximum of 1 amino acid selected from Arg, His, Gly and Ala ($aa_3$). In another embodiment, X comprises a maximum of 2 amino acids selected from Arg, His, Gly and Ala ($aa_3$). In yet another embodiment, X comprises a maximum of 1 Arg residue, and/or comprises a maximum of 1 His residue, and/or comprises a maximum of 1 Gly residue, and/or comprises a maximum of 1 Ala residue.

In a particular embodiment, the molecule to be attached to the ε-amino group(s) of the one or more lysine residues of the lysine backbone of X is selected from the group consisting of Lys, Ac-Lys, Lys-Lys, Ac-Lys-Lys, Lys-Lys-Lys, Ac-Lys-Lys-Lys, Lys-Lys-Lys-Lys (SEQ ID NO:22), Ac-Lys-Lys-Lys-Lys (Ac-SEQ ID NO:22), Lys-Gly-Lys, Ac-Lys-Gly-Lys, Lys-Lys-Gly, Ac-Lys-Lys-Gly, Lys-Gly, Ac-Lys-Gly, Lys-Ala-Lys. Ac-Lys-Ala-Lys, Lys-Lys-Ala, Ac-Lys-Lys-Ala, Lys-Ala, Ac-Lys-Ala, Lys-His-Lys, Ac-Lys-His-Lys, Lys-Lys-His, Ac-Lys-Lys-His, Lys-His, Ac-Lys-His, Lys-Arg-Lys, Ac-Lys-Arg-Lys, Lys-Lys-Arg, Ac-Lys-Lys-Arg, Lys-Arg and Ac-Lys-Arg. All the above-mentioned Lys, Gly, Ala, His and Arg residues may each be in the L- or D-conformation.

In a particular embodiment, X comprises a branched amino acid probe consisting of a first lysine residue selected from Lys and D-Lys, said first lysine residue being optionally acetylated, wherein said first lysine residue is modified by attaching to the ε-amino group of said first lysine residue a molecule selected from the group consisting of Lys, Ac-Lys, Lys-Lys, Ac-Lys-Lys, Lys-Lys-Lys, Ac-Lys-Lys-Lys, Lys-Lys-Lys-Lys (SEQ ID NO:22), Ac-Lys-Lys-Lys-Lys (Ac-SEQ ID NO:22), Lys-Gly-Lys, Ac-Lys-Gly-Lys, Lys-Lys-Gly, Ac-Lys-Lys-Gly, Lys-Gly, Ac-Lys-Gly, Lys-Ala-Lys, Ac-Lys-Ala-Lys, Lys-Lys-Ala, Ac-Lys-Lys-Ala, Lys-Ala, Ac-Lys-Ala, Lys-His-Lys, Ac-Lys-His-Lys, Lys-Lys-His, Ac-Lys-Lys-His, Lys-His, Ac-Lys-His, Lys-Arg-Lys, Ac-Lys-Arg-Lys, Lys-Lys-Arg, Ac-Lys-Lys-Arg, Lys-Arg and Ac-Lys-Arg. All the above-mentioned Lys, Gly, Ala, His and Arg residues may each be in the L- or D-conformation.

Figure 7:
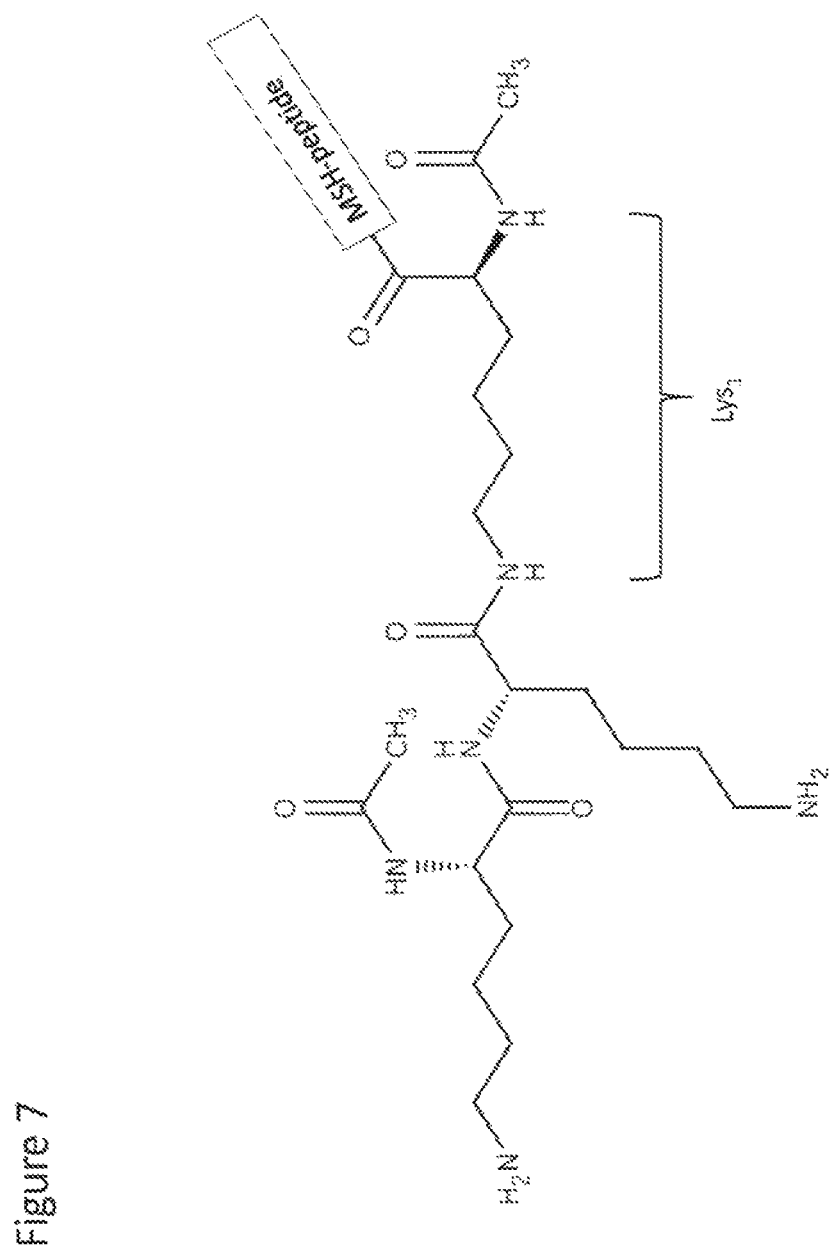
FIG. 7: Schematic representation of the branched amino acid probe (BAP) Ac-(Ac-Lys-Lys)Lys- (i.e. one embodiment of X of the equation X-(aa₁)$_n$-Y-(aa₂)$_m$-Z), showing the first lysine of X (Lys₁) being attached to the MSH-peptide via a regular peptide bond, said first lysine being acetylated (COCH₃), and said first lysine being modified by attaching to the s-amino group of said first lysine residue two further lysine residues wherein one is also acetylated (the outermost).

In one embodiment X comprises or consists of the formula: Ac-(Ac-Lys-Lys)$Lys_1$-(identical to Ac-(Ac-Lys-Lys) Lys-), wherein $Lys_1$ is the first lysine residue being attached by a peptide bond to the most N-terminal amino acid residue of the MSH-peptide, being acetylated, and (Ac-Lys-Lys) is the molecule being attached to the ε-amino group of said first lysine residue $Lys_1$. FIG. 7 illustrates this formula/structure.

In one embodiment X comprises or consists of a formula selected from the group consisting of Ac-(Ac-Lys)$Lys_1$-, Ac-(Ac-Lys-Lys)$Lys_1$-, Ac-(Ac-Lys-Lys)$Lys_1$-, Ac-(Ac-Lys-Lys-Lys)$Lys_1$-, Ac-(Ac-Lys-Lys-Lys-Lys)$Lys_1$-, Ac-(Ac-Lys-Gly-Lys)$Lys_1$-, Ac-(Ac-Lys-Lys-Gly)$Lys_1$-, Ac-(Ac-Lys-Gly)$Lys_1$-, Ac-(Ac-Lys-Ala-Lys)$Lys_1$-, Ac-(Ac-Lys-Lys-Ala)$Lys_1$-, Ac-(Ac-Lys-Ala)$Lys_1$-, Ac-(Ac-Lys-His-Lys)$Lys_1$-, Ac-(Ac-Lys-Lys-His)$Lys_1$-, Ac-(Ac-Lys-His)$Lys_1$-, Ac-(Ac-Lys-Arg-Lys)$Lys_1$-, Ac-(Ac-Lys-Lys-Arg)$Lys_1$-, and Ac-(Ac-Lys-Arg)$Lys_1$-. More specifically, in one embodiment X comprises or consists of a formula selected from the group consisting of Ac-(Ac-Lys)$Lys_1$-, Ac-(Ac-Lys-Lys)$Lys_1$-, Ac-(Ac-Lys-Lys-Lys)$Lys_1$-, Ac-(Ac-Lys-Lys-Lys-Lys)$Lys_1$-. Ac-(Ac-Lys-Gly-Lys) $Lys_1$-, Ac-(Ac-Lys-Lys-Gly)$Lys_1$- and Ac-(Ac-Lys-Gly)$Lys_1$-.

In a particular embodiment, X comprises a branched amino acid probe consisting of a first and a second lysine residue selected from Lys and D-Lys, said first and second lysine residue being optionally acetylated, wherein said first and/or second lysine residue each are modified by attaching to the ε-amino group of said first and/or second lysine residue a molecule selected from the group consisting of Lys, Ac-Lys, Lys-Lys, Ac-Lys-Lys, Lys-Lys-Lys, Ac-Lys-Lys-Lys, Lys-Lys-Lys-Lys (SEQ ID NO:22), Ac-Lys-Lys-Lys-Lys (Ac-SEQ ID NO:22), Lys-Gly-Lys, Ac-Lys-Gly-Lys, Lys-Lys-Gly, Ac-Lys-Lys-Gly, Lys-Gly, Ac-Lys-Gly, Lys-Ala-Lys, Ac-Lys-Ala-Lys, Lys-Lys-Ala, Ac-Lys-Lys-Ala, Lys-Ala, Ac-Lys-Ala, Lys-His-Lys, Ac-Lys-His-Lys, Lys-Lys-His, Ac-Lys-Lys-His, Lys-His, Ac-Lys-His, Lys-Arg-Lys, Ac-Lys-Arg-Lys. Lys-Lys-Arg, Ac-Lys-Lys-Arg, Lys-Arg and Ac-Lys-Arg. All the above-mentioned Lys, Gly, Ala, His and Arg residues may each be in the L- or D-conformation.

In one embodiment X comprises or consists of the formula: Ac-(Ac-Lys)$Lys_2$-$Lys_1$-, wherein $Lys_1$ is the first lysine residue being attached by a peptide bond to the most N-terminal amino acid residue of the MSH-peptide, being acetylated, $Lys_2$ is the second lysine residue being attached to $Lys_1$ via a peptide bond, and (Ac-Lys-Lys) is the molecule being attached to the ε-amino group of said first lysine residue $Lys_1$. In the embodiment of the molecule Ac-$Lys_2$-(Ac-Lys)$Lys_1$-, the molecule (Ac-Lys) is attached to the ε-amino group of said second lysine residue $Lys_2$.

In one embodiment X comprises or consists of a formula selected from the group consisting of Ac-(Ac-Lys)$Lys_2$-$Lys_1$-, Ac-(Ac-Lys-Lys)$Lys_2$-$Lys_1$-, Ac-(Ac-Lys-Gly)$Lys_2$-$Lys_1$-, Ac-(Ac-Lys-Lys-Lys)$Lys_2$-$Lys_1$-, Ac-(Ac-Lys-Lys-Lys)$Lys_2$-$Lys_1$-, Ac-(Ac-Lys)-$Lys_1$-, Ac-$Lys_2$-(Ac-Lys-Lys)-$Lys_1$-, Ac-Lys-(Ac-Lys-Gly)-$Lys_1$-, Ac-$Lys_2$-(Ac-Lys-Lys-Lys)-$Lys_1$-, Ac-$Lys_2$-(Ac-Lys-Lys-Lys-Lys)-$Lys_1$-, Ac-(Ac-Lys)$Lys_2$-(Ac-Lys-)-$Lys_1$-, Ac-(Ac-Lys)$Lys_2$-(Ac-Lys-Lys-)-$Lys_1$-, and Ac-(Ac-Lys)$Lys_2$-(Ac-Lys-Lys-)-$Lys_1$-.

More specifically, in one embodiment X comprises or consists of a formula selected from the group consisting of Ac-(Ac-Lys)$Lys_2$-$Lys_1$-, Ac-(Ac-Lys-Lys)$Lys_2$-$Lys_1$-, Ac-(Ac-Lys-Gly)$Lys_2$-$Lys_1$-, Ac-$Lys_2$-(Ac-Lys)-$Lys_1$-, Ac-$Lys_2$-(Ac-Lys-Lys)-$Lys_1$-, Ac-$Lys_2$-(Ac-Lys-Gly)-$Lys_1$-, Ac-(Ac-Lys)$Lys_2$-(Ac-Lys-)-$Lys_1$-, Ac-(Ac-Lys)$Lys_2$-(Ac-Lys-Lys-)-$Lys_1$-, and Ac-(Ac-Lys-Lys)$Lys_2$-(Ac-Lys-Lys-)-$Lys_1$-.

In a particular embodiment, X comprises a branched amino acid probe consisting of a first, a second and a third lysine residue selected from Lys and D-Lys, said first, second and/or third lysine residue being optionally acetylated, wherein said first, second and/or third lysine residue each are modified by attaching to the ε-amino group of said first, second and/or third lysine residue a molecule selected from the group consisting of Lys, Ac-Lys, Lys-Lys, Ac-Lys-Lys, Lys-Lys-Lys, Ac-Lys-Lys-Lys, Lys-Lys-Lys-Lys (SEQ ID NO:22), Ac-Lys-Lys-Lys-Lys (Ac-SEQ ID NO:22), Lys-Gly-Lys, Ac-Lys-Gly-Lys, Lys-Lys-Gly, Ac-Lys-Lys-Gly, Lys-Gly, Ac-Lys-Gly, Lys-Ala-Lys, Ac-Lys-Ala-Lys, Lys-Lys-Ala, Ac-Lys-Lys-Ala, Lys-Ala, Ac-Lys-Ala, Lys-His-Lys, Ac-Lys-His-Lys, Lys-Lys-His, Ac-Lys-Lys-His, Lys-His, Ac-Lys-His, Lys-Arg-Lys, Ac-Lys-Arg-Lys, Lys-Lys-Arg, Ac-Lys-Lys-Arg, Lys-Arg and Ac-Lys-Arg. All the above-mentioned Lys, Gly, Ala, His and Arg residues may each be in the L- or D-conformation.

In one embodiment X comprises or consists of a formula selected from the group consisting of Ac-Lys$_3$-Lys$_2$-(Ac-Lys)Lys$_1$-, Ac-Lys$_3$-(Ac-Lys)Lys$_2$-Lys$_1$-, Ac-(Ac-Lys)Lys$_3$-Lys$_2$-Lys$_1$-, Ac-Lys$_3$-(Ac-Lys)Lys$_2$-(Ac-Lys)Lys$_1$-, Ac-(Ac-Lys)Lys$_3$-(Ac-Lys)Lys$_2$-Lys$_1$-, and Ac-(Ac-Lys)Lys$_3$-Lys$_2$-(Ac-Lys)Lys$_1$-.

In a particular embodiment X comprises or consists of a formula selected from the group consisting of Ac-(Ac-Lys)Lys$_1$-, Ac-(Ac-Lys-Lys)Lys$_1$-, Ac-(Ac-Lys-Lys-Lys)Lys$_1$-, Ac-(Ac-Lys-Lys-Lys-Lys)Lys$_1$-, Ac-(Ac-Lys-Gly-Lys)Lys$_1$-, Ac-(Ac-Lys-Lys-Gly)Lys$_1$-, Ac-(Ac-Lys-Gly) Lys$_1$-, Ac-(Ac-Lys)Lys-Lys$_1$-, Ac-(Ac-Lys-Lys)Lys$_2$-Lys$_1$-, Ac-(Ac-Lys-Gly)Lys$_2$-Lys$_1$-, Ac-Lys$_2$-(Ac-Lys)-Lys$_1$-, Ac-Lys$_2$-(Ac-Lys-Lys)-Lys$_1$-, Ac-Lys$_2$-(Ac-Lys-Gly)-Lys$_1$-, Ac-(Ac-Lys)Lys$_2$-(Ac-Lys-)-Lys$_1$-, Ac-(Ac-Lys)Lys$_2$-(Ac-Lys-Lys-)-Lys$_1$-, Ac-(Ac-Lys-Lys)Lys$_2$-(Ac-Lys-Lys-)-Lys$_1$-, Ac-Lys$_3$-Lys$_2$-(Ac-Lys)Lys$_1$-, Ac-Lys$_3$-(Ac-Lys)Lys-Lys$_1$-, Ac-(Ac-Lys)Lys$_3$-Lys$_2$-Lys$_1$-, Ac-Lys$_3$-(Ac-Lys)Lys$_2$-(Ac-Lys)Lys$_1$-, Ac-(Ac-Lys)Lys$_3$-(Ac-Lys)Lys$_2$-Lys$_1$-, and Ac-(Ac-Lys)Lys$_3$-Lys$_2$-(Ac-Lys)Lys$_1$-.

In a particular embodiment, X comprises a branched amino acid probe consisting of a first and a second lysine residue selected from Lys and D-Lys, wherein one or both of the first and second lysine residues are modified by attaching to the ε-amino group of said first and/or second lysine residue one lysine residue selected from Lys and D-Lys.

In a particular embodiment, X comprises a branched amino acid probe consisting of a first and a second lysine residue selected from Lys and D-Lys, wherein one of either the first or the second lysine residues are modified by attaching to the s-amino group of said first or second lysine residue one lysine residue selected from Lys and D-Lys.

Length

In one embodiment, the present invention is directed to a peptide consisting of from 8 to 22 amino acid residues comprising an amino acid sequence as defined herein above. In a particular embodiment, said peptide consists of from 8 to 9 amino acids, for example 9 to 10 amino acid residues, such as from 10 to 11 amino acid residues, for example from 11 to 12 amino acid residues, such as from 12 to 13 amino acid residues, for example from 13 to 14 amino acid residues, such as from 14 to 15 amino acid residues, for example from 15 to 16 amino acid residues, such as from 16 to 17 amino acid residues, for example from 17 to 18 amino acid residues, such as from 18 to 19 amino acid residues, for example from 19 to 20 amino acid residues, such as from 20 to 21 amino acid residues, for example from 21 to 22 amino acid residues comprising an amino acid sequence as defined herein above.

In one particular embodiment, the peptide according to the present invention consists of from 14 to 22 amino acid residues. In another particular embodiment, the peptide according to the present invention consists of from 8 to 18 amino acid residues. In yet another particular embodiment, the peptide according to the present invention consists of from 14 to 18 amino acid residues, such as from 14 to 16 amino acid residues.

A peptide consisting of for example from 8 to 22 amino acid residues is meant to refer to a peptide amounting in total of from 8 to 22 amino acid residues. This does however not exclude that the peptide is further modified by any other means known to the skilled person, such as being linked to other molecules, being comprised in a larger complex, being post-translationally modified and so forth.

Examples of Specific Peptides of the Invention

The peptide according to the present invention may in one particular embodiment consist of the amino acid sequence X-(aa$_1$)$_n$-Y-(aa$_2$)$_m$-Z, wherein (aa$_1$)$_n$ is Ser-Tyr-Ser-Met-Glu (SEQ ID NO:17), Ser-Tyr-Ser-Nle-Glu (SEQ ID NO:18) or Ser-Ser-Ile-Ile-Ser (SEQ ID NO:19); Y is His-Phe-Arg-Trp (SEQ ID NO:16), His-(D-Phe)-Arg-Trp or His-Phe-Arg-(D-Trp); (aa$_2$)$_m$ is Gly and Z is Lys-Pro-Val.

Specifically, in one embodiment (aa$_1$)$_n$ is Ser-Tyr-Ser-Met-Glu (SEQ ID NO:17), Y is His-Phe-Arg-Trp (SEQ ID NO: 16), (aa$_2$)$_m$ is Gly and Z is Lys-Pro-Val. This corresponds to native α-MSH peptide being modified with the X motif as defined herein.

It follows that according to the present invention the peptide may be an α-MSH analogue consisting of a sequence selected from the group consisting of:

```
                                         (SEQ ID NO: 1)
X-Ser-Tyr-Ser-Met-Glu-His-Phe-Arg-Trp-Gly-Lys-Pro-
Val,

X-Ser-Tyr-Ser-Met-Glu-His-(D-Phe)-Arg-Trp-Gly-Lys-
Pro-Val,

X-Ser-Tyr-Ser-Met-Glu-His-Phe-(D-Arg)-Trp-Gly-Lys-
Pro-Val

X-Ser-Tyr-Ser-Met-Glu-His-Phe-Arg-(D-Trp)-Gly-Lys-
Pro-Val,

X-Ser-Tyr-Ser-Met-Glu-His-(D-Phe)-Arg-(D-Trp)-Gly-
Lys-Pro-Val,

X-Ser-Tyr-Ser-Met-Glu-His-Nal-Arg-Trp-Gly-Lys-Pro-
Val,

X-Ser-Tyr-Ser-Met-Glu-His-(D-Nal)-Arg-Trp-Gly-Lys-
Pro-Val,

X-Ser-Tyr-Ser-Met-Glu-His-Phe-Arg-Trp-Gly-Lys-Pro-
(D-Val),

X-Ser-Tyr-Ser-Met-Glu-His-(D-Phe)-Arg-Trp-Gly-Lys-
Pro-(D-Val),

X-Ser-Tyr-Ser-Met-Glu-His-Phe-(D-Arg)-Trp-Gly-Lys-
Pro-(D-Val),

X-Ser-Tyr-Ser-Met-Glu-His-Phe-Arg-(D-Trp)-Gly-Lys-
Pro-(D-Val),

X-Ser-Tyr-Ser-Met-Glu-His-(D-Phe)-Arg-(D-Trp)-Gly-
Lys-Pro-(D-Val),

X-Ser-Tyr-Ser-Met-Glu-His-Nal-Arg-Trp-Gly-Lys-Pro-
(D-Val),

X-Ser-Tyr-Ser-Met-Glu-His-(D-Nal)-Arg-Trp-Gly-Lys-
Pro-(D-Val), (SEQ ID NO: 3)
X-Ser-Tyr-Ser-Met-Glu-His-Phe-Arg-Trp-Gly-Lys-Pro-
Val,

X-Ser-Tyr-Ser-Nle-Glu-His-(D-Phe)-Arg-Trp-Gly-Lys-
Pro-Val,
```

-continued

X-Ser-Tyr-Ser-Nle-Glu-His-Phe-(D-Arg)-Trp-Gly-Lys-
Pro-Val

X-Ser-Tyr-Ser-Met-Glu-His-Phe-Arg-(D-Trp)-Gly-Lys-
Pro-Val,

X-Ser-Tyr-Ser--Nle-Glu-His-(D-Phe)-Arg-(D-Trp)-
Gly-Lys-Pro-Val,

X-Ser-Tyr-Ser-Nle-Glu-His-Nal-Arg-Trp-Gly-Lys-Pro-
Val,

X-Ser-Tyr-Ser-Nle-Glu-His-(D-Nal)-Arg-Trp-Gly-Lys-
Pro-Val,

X-Ser-Tyr-Ser-Nle-Glu-His-Phe-Arg-Trp-Gly-Lys-Pro-
(D-Val),

X-Ser-Tyr-Ser-Nle-Glu-His-(D-Phe)-Arg-Trp-Gly-Lys-
Pro-(D-Val),

X-Ser-Tyr-Ser-Nle-Glu-His-Phe-(D-Arg)-Trp-Gly-Lys-
Pro-(D-Val),

X-Ser-Tyr-Ser-Nle-Glu-His-Phe-Arg-(D-Trp)-Gly-Lys-
Pro-(D-Val),

X-Ser-Tyr-Ser-Nle-Glu-His-(D-Phe)-Arg-(D-Trp)-Gly-
Lys-Pro-(D-Val),

X-Ser-Tyr-Ser-Nle-Glu-His-Nal-Arg-Trp-Gly-Lys-Pro-
(D-Val),

X-Ser-Tyr-Ser-Nle-Glu-His-(D-Nal)-Arg-Trp-Gly-Lys-
Pro-(D-Val), (SEQ ID NO: 5)
X-Ser-Ser-Ile-Ile-Ser-His-Phe-Arg-Trp-Gy-Lys-Pro-
Val,

X-Ser-Ser-Ile-Ile-Ser-His-(D-Phe)-Arg-Trp-Gly-Lys-
Pro-Val,

X-Ser-Ser-Ile-lle-Ser-His-Phe-(D-Arg)-Trp-Gly-Lys-
Pro-Val,

X-Ser-Ser-Ile-Ile-Ser-His-Phe-Arg-(D-Trp)-Gly-Lys-
Pro-Val,

X-Ser-Ser-Ile-Ile-Ser-His-(D-Phe)-Arg-(D-Trp)-Gly-
Lys-Pro-Val,

X-Ser-Ser-Ile-Ile-Ser-His-Nal-Arg-Trp-Gly-Lys-Pro-
Val,

X-Ser-Ser-Ile-Ile-Ser-His-(D-Nal)-Arg-Trp-Gly-Lys-
Pro-Val,

X-Ser-Ser-Ile-Ile-Ser-His-Phe-Arg-Trp-Gly-Lys-Pro-
(D-Val),

X-Ser-Ser-Ile-Ile-Ser-His-(D-Phe)-Arg-Trp-Gly-Lys-
Pro-(D-Val),

X-Ser-Ser-Ile-Ile-Ser-His-Phe-(D-Arg)-Trp-Gly-Lys-
Pro-(D-Val),

X-Ser-Ser-Ile-Ile-Ser-His-Phe-Arg-(D-Trp)-Gly-Lys-
Pro-(D-Val),

X-Ser-Ser-Ile-Ile-Ser-His(D-Phe)-Arg-(D-Ttp)-Gly-
Lys-Pro-(D-Val),

X-Ser-Ser-Ile-Ile-Ser-His-Nal-Arg-Trp-Gly-Lys-Pro-
(D-Val),
and

X-Ser-Ile-Ile-Ser-His-(D-Nal)-Arg-Trp-Gly-Lys-Pro-
(D-Val), wherein X is a branched amino acid probe as defined herein above.

In one embodiment, the most carboxy terminal Val or (D-Val) is a Valine amide.

Furthermore, the peptide according to the present invention may in one particular embodiment consist of the amino acid sequence X-(aa$_1$)$_n$-Y-(aa$_2$)$_m$-Z, wherein (aa$_1$)$_n$ is Tyr-Val-Met-Gly (SEQ ID NO:20) or Tyr-Val-Nle-Gly (SEQ ID NO:21); Y is His-Phe-Arg-Trp (SEQ ID NO:16); His-(D-Phe)-Arg-Trp; His-Phe-(D-Arg)-Trp; His-Phe-Arg-(D-Trp); His-(D-Phe)-Arg-(D-Trp); His-Nat-Arg-Trp or His-(D-Nal)-Arg-Trp; (aa$_2$)$_m$ is Asp and Z is selected from the group consisting of Arg-Phe-Gly; Arg-(D-Phe)-Gly; Arg-Phe and Arg-(D-Phe).

Specifically, in one embodiment (aa$_1$)$_n$ is Tyr-Val-Met-Gly (SEQ ID NO:20), Y is His-Phe-Arg-Trp (SEQ ID NO:16), (aa$_2$)$_m$ is Asp and Z is selected from the group consisting of Arg-Phe-Gly and Arg-Phe. This corresponds to native γ-MSH peptide (type 1 or 2) being modified with the X motif as defined herein.

According to the present invention the peptide may be a γ1-MSH analogue consisting of a sequence selected from the group consisting of:

(SEQ ID NO: 7)
X-Tyr-Val-Met-Gly-His-Phe-Arg-Trp-Asp-Arg-Phe-Gly,

X-Tyr-Val-Met-Gly-His-(D-Phe)-Arg-Trp-Asp-Arg-
Phe-Gly,

X-Tyr-Val-Met-Gly-His-Phe-(D-Arg)-Trp-Asp-Arg-
Phe-Gly,

X-Tyr-Val-Met-Gly-His-Phe-Arg-(D-Trp)-Asp-Arg-
Phe-Gly,

X-Tr-Val-Met-Gly-His-(D-Phe)-Arg-(D-Trp)-Asp-
Arg-Phe-Gly,

X-Tyr-Val-Met-Gly-His-Nal-Arg-Trp-Asp-Arg-Phe-Gly,

X-Tyr-Val-Met-Gly-His-(D-Nal)-Arg-Trp-Asp-Arg-
Phe-Gly,

X-Tyr-Val-Met-Gly-His-Phe-Arg-Trp-Asp-Arg-(D-Phe)-
Gly,

X-Tyr-Val-Met-Gly-His-(D-Phe)-Arg-Trp-Asp-Arg-
(D-Phe)-Gly,

X-Tyr-Val-Met-Gly-His-Phe-(D-Arg)-Trp-Asp-Arg-
(D-Phe)-Gly,

X-Tyr-Val-Met-Gly-His-Phe-Arg-(D-Trp)-Asp-Arg-
(D-Phe)-Gly,

X-Tyr-Val-Met-Gly-His-(D-Phe)-Arg-(D-Trp)-Asp-
Arg-(D-Phe)-Gly,

X-Tyr-Val-Met-Gly-His-Nal-Arg-Trp-Asp-Arg-(D-Phe)-
Gly,

X-Tyr-Val-Met-Gly-His-(D-Nal)-Arg-Trp-Asp-Arg-
(D-Phe)-Gly, (SEQ ID NO: 9)
X-Tyr-Val-Nle-Gly-His-Phe-Arg-Trp-Asp-Arg-Phe-Gly,

X-Tyr-Val-Nle-Gly-His-(D-Phe)-Arg-Trp-Asp-Arg-
Phe-Gly,

X-Tyr-Val-Nle-Gly-His-Phe-(D-Arg)-Trp-Asp-Arg-
Phe-Gly,

-continued

```
X-Tyr-Val-Nle-Gly-His-Phe-Arg-(D-Trp)-Asp-Arg-
Phe-Gly,

X-Tyr-Val-Nle-Gly-His-(D-Phe)-Arg-(D-Trp)-Asp-
Arg-Phe-Gly,

X-Tyr-Val-Nle-Gly-His-Nal-Arg-Trp-Asp-Arg-Phe-Gly,

X-Tyr-Val-Nle-Gly-His(D-Nal)-Arg-Trp-Asp-Arg-
Phe-Gly,

X-Tyr-Val-Nle-Gly-His-Phe-Arg-Trp-Asp-Arg-(D-Phe)-
Gly,

X-Tyr-Val-Nle-Gly-His-(D-Phe)-Arg-Trp-Asp-Arg-
(D-Phe)-Gly,

X-Tyr-Vag-Nle-Gly-His-Phe-(D-Arg)-Trp-Asp-Arg-
(D-Phe)-Gly,

X-Tyr-Val-Nle-Gly-His-Phe-Arg-(D-Trp)-Asp-Arg-
(D-Phe)-Gly,

X-Tyr-Val-Nle-Gly-His-(D-Phe)-Arg-(D-Trp)-Asp-Arg-
(D-Phe)-Gly,

X-Tyr-Val-Nle-Gly-His-Nal-Arg-Trp-Asp-Arg-(D-Phe)-
Gly,
and

X-Tyr-Val-Nle-Gly-His-(D-Nal)-Arg-Trp-Asp-Arg-
(D-Phe)-Gly,
``` wherein X is a branched amino acid probe as defined herein above.

In one embodiment, the most carboxy terminal City is Glycine amide.

According to the present invention the peptide may be a γ2-MSH analogue consisting of a sequence selected from the group consisting of:

```
                                          (SEQ ID NO: 11)
X-Tyr-Val-Met-Gly-His-Phe-Arg-Trp-Asp-Arg-Phe,

X-Tyr-Val-Met-Gly-His-(D-Phe)-Arg-Trp-Asp-Arg-Phe,

X-Tyr-Val-Met-Gly-His-Phe-(D-Arg)-Trp-Asp-Arg-Phe,

X-Tyr-Val-Met-Gly-His-Phe-Arg-(D-Trp)-Asp-Arg-Phe,

X-Tyr-Val-Met-Gly-His-(D-Phe)-Arg-(D-Trp)-Asp-
Arg-Phe,

X-Tyr-Val-Met-Gly-His-Nal-Arg-Trp-Asp-Arg-Phe,

X-Tyr-Val-Met-Gly-His-(D-Nal)-Arg-Trp-Asp-Arg-Phe,

X-Tyr-Val-Met-Gly-His-Phe-Arg-Trp-Asp-Arg-(D-Phe),

X-Tyr-Val-Met-Gly-His-(D-Phe)-Arg-Trp-Asp-Arg-
(D-Phe),

X-Tyr-Val-Met-Gly-His-Phe-(D-Arg)-Trp-Asp-Arg-
(D-Phe),

X-Tyr-Val-Met-Gly-His-Phe-Arg-(D-Trp)-Asp-Arg-
(D-Phe),

X-Tyr-Val-Met-Gly-His-(D-Phe)-Arg-(D-Trp)-Asp-
Arg-(D-Phe),

X-Tyr-Val-Met-Gly-His-Nal-Arg-Trp-Asp-Arg-(D-Phe),

X-Tyr-Val-Met-Gly-His-(D-Nal)-Arg-Trp-Asp-Arg-
(D-Phe),
```

```
                                          (SEQ ID NO: 13)
X-Tyr-Val-Nle-Gly-His-Phe-Arg-Trp-Asp-Arg-Phe,

X-Tyr-Val-Nle-Gly-His-(D-Phe)-Arg-Trp-Asp-Arg-Phe,

X-Tyr-Val-Nle-Gly-His-Phe-(D-Arg)-Trp-Asp-Arg-Phe,

X-Tyr-Val-Nle-Gly-His-Phe-Arg-(D-Trp)-Asp-Arg-Phe,

X-Tyr-Val-Nle-Gly-His-(D-Phe)-Arg-(D-Trp)-Asp-
Arg-Phe,

X-Tyr-Val-Nle-Gly-His-Nal-Arg-Trp-Asp-Arg-Phe,

X-Tyr-Val-Nle-Gly-His-(D-Nal)-Arg-Trp-Asp-Arg-Phe,

X-Tyr-Val-Nle-Gly-His-Phe-Arg-Trp-Asp-Arg-(D-Phe),

X-Tyr-Val-Nle-Gly-His-(D-Phe)-Arg-Trp-Asp-Arg-
(D-Phe),

X-Tyr-Val-Nle-Gly-His-Phe-(D-Arq)-Trp-Asp-Arg-
(D-Phe),

X-Tyr-Val-Nle-Gly-His-Phe-Arg-(D-Trp)-Asp-Arg-
(D-Phe),

X-Tyr-Val-Nle-Gly-His-(D-Phe)-Arg-(D-Trp)-Asp-
Arg-(D-Phe)

X-Tyr-Val-Nle-Gly-His-Nal-Arg-Trp-Asp-Arg-(D-Phe),
and
X-Tyr-Val-Nle-Gly-His-(D-Nal)-Arg-Trp-Asp-Arg-
(D-Phe),
``` wherein X is a branched amino acid probe as defined herein above.

In one embodiment, the most carboxy terminal Phe or (D-Phe) is a Phenylalanine amide.

Activity

The term "agonist" in the present context refers to a substance or peptide as defined herein, capable of binding to, or in some embodiments, capable of binding to at least some extent and/or activating a receptor, or in some embodiments, activating a receptor to at least some extent. A MC1r receptor agonist (MC1r agonist) is thus capable of binding to and/or activating the MC1r receptor. The terms 'MC1r agonist' and 'MC1r receptor agonist' are used interchangeably herein.

An agonist may be an agonist of several different types of receptors, and thus capable of binding and/or activating several different types of receptors. Said agonist can also be a selective agonist which only binds and activates one type of receptor. The term "antagonist" in the present context refers to a substance capable of inhibiting the effect of a receptor agonist.

Full agonists bind (have affinity for) and activate a receptor, displaying full efficacy at that receptor. "Partial agonists" in the present context are peptides able to bind and activate a given receptor, but having only partial efficacy at the receptor relative to a full agonist. Partial agonists can act as antagonists when competing with a full agonist for receptor occupancy and producing a net decrease in the receptor activation compared to the effects or activation observed with the full agonist alone.

"Selective agonists" in the present context are compounds which are selective and therefore predominantly bind and activates one type of receptor. Thus a selective MC1r receptor agonist is selective for the MC1r receptor.

Peptides according to the present invention are in one embodiment capable of binding and activating to some extent one or several melanocortin receptors and can have different binding affinities and/or different receptor activation efficacy for different MC receptors, wherein affinity refers to the number and size of intermolecular forces between a peptide ligand and its receptor, and residence time of the ligand at its receptor binding site; and receptor activation efficacy refers to the ability of the peptide ligand to produce a biological response upon binding to the target receptor and the quantitative magnitude of this response. In some embodiments, such differences in affinity and receptor activation efficacy are determined by receptor binding/activation studies which are conventional in the art, for instance by generating $EC_{50}$ and Emax values for stimulation of ligand binding in cells expressing one or several types of MC receptors as mentioned herein, or on tissues expressing the different types of MC receptors. High affinity means that a lower concentration of a compound is needed to obtain a binding of 50% of the receptors compared to peptides which have lower affinity; high receptor activation efficacy means that a lower concentration of the peptide is needed to obtain a 50% receptor activation response (low $EC_{50}$ value), compared to peptides which have lower affinity and/or receptor activity efficacy (higher $EC_{50}$ value).

In one embodiment of the present invention, the peptides which are combined agonists of two or more of the MC receptors have differing affinities and/or receptor activation efficacies for two or more of the receptors selected from MC1R, MC2r, MC3r, MC4r and MC5r.

The receptor activation potency of peptide agonists of the present invention can also be measured in $p(A_{50})$ values which is a conventional method for determining the receptor activation efficacy of an agonist.

In one particular embodiment, the peptides according to the present invention are capable of binding to and activating at least the melanocortin receptor MC1r. In a further embodiment said peptide is a full agonist of the melanocortin receptor MC1r.

In a further embodiment, said peptide is further capable of binding to and activating melanocortin receptor MC3r. It follows that the peptide of the present invention in one embodiment is capable of binding to and activating the melanocortin receptors MC1r and/or MC3r. In another embodiment, the peptide of the present invention is capable of binding to and activating the melanocortin receptors MC1r and MC3r.

Method of Preparation

The peptides according to the present invention may be prepared by any suitable methods known in the art. Thus, in some embodiments the α- and γ-MSH (native or variants/analogues as defined herein), and the X motif, are prepared by standard peptide-preparation techniques, such as solution synthesis or solid phase peptide synthesis (SPPS) such as Merrifield-type solid phase synthesis.

The peptides of the invention are in one embodiment prepared by solid phase synthesis by first constructing the pharmacologically active peptide sequence (α- or γ-MSH; native or variants as defined herein), using well-known standard protection, coupling and de-protection procedures, thereafter sequentially coupling the branched amino acid sequence of the motif X onto the active peptide in a manner similar to the construction of the active peptide, and finally cleaving off the entire peptide from the carrier. This strategy yields a peptide, wherein the motif X is covalently bound to the pharmacologically active peptide at the N-terminal nitrogen atom of the peptide.

In one embodiment, the alpha nitrogen on the final amino acid in the branched amino acid sequence are capped with acetyl, using standard acylation techniques, prior to or after coupling of the branched amino acid sequence on the active peptide.

Reactive moieties at the N- and C-termini, which facilitates amino acid coupling during synthesis, as well as reactive side chain functional groups, can interact with free termini or other side chain groups during synthesis and peptide elongation and negatively influence yield and purity. Chemical groups are thus developed that bind to specific amino acid functional groups and block, or protect, the functional group from nonspecific reactions. Purified, individual amino acids are reacted with these protecting groups prior to synthesis and then selectively removed during specific steps of peptide synthesis. Examples of N-terminal protecting groups are t-Boc and Fmoc, commonly used in solid-phase peptide synthesis. C-terminal protecting groups are mostly used in liquid-phase synthesis. Because N-terminal deprotection occurs continuously during peptide synthesis, protecting schemes have been established in which the different types of side chain protecting groups (benzyl; Bzl or tert-butyl; tBu) are matched to either Boc or Fmoc, respectively, for optimized deprotection.

In a particular embodiment of the invention, when preparing the branched amino acid probe, examplified by Ac(Ac-Lys-Lys)Lys-, the protection group for Lys is Mtt, which protected amino acid is commercially available (Fmoc-Lys(Mtt)-OH; N-α-Fmoc-N-ε-4-methyltrityl-L-lysine, CAS#167393-62-6). Lys(Mtt) allows for capping Lys with acetyl as it is not cleaved under the conditions that cleave Fmoc, and may be removed without cleavage of other side chain protection groups.

The method of preparation is in some embodiments optimized by routine methods in the art that may increase the yield and/or quality of the thus prepared synthetic peptide. For instance, use of pseudoproline (oxazolidine) dipeptides in the Fmoc SPPS of serine- and threonine-containing peptides may lead to improvements in quality and yield of crude products and may help avoid unnecessary repeat synthesis of failed sequences. These dipeptides are easy to use: simply substitute a serine or threonine residue together with the preceding amino acid residue in the peptide sequence with the appropriate pseudoproline dipeptide. The native sequence is regenerated on cleavage and deprotection.

In one embodiment the sequence of the pharmacologically active peptide sequence (α- or γ-MSH; native or variants as defined herein) and the X-motif (or parts thereof) are each prepared separately by for example solution synthesis, solid phase synthesis, recombinant techniques, or enzymatic synthesis, followed by coupling of the (at least) two sequences by well-known segment condensation procedures, either in solution or using solid phase techniques, or a combination thereof.

In one embodiment, the α- or γ-MSH as defined herein are prepared by recombinant DNA methods and the X motif is prepared by solid or solution phase synthesis. The conjugation of the α- or γ-MSH and the X motif is in one embodiment carried out by using chemical ligation. This technique allows for the assembling of totally unprotected peptide segments in a highly specific manner. In another embodiment, the conjugation is performed by protease-catalysed peptide bond formation, which offers a highly specific technique to combine totally unprotected peptide segments via a peptide bond.

In one embodiment, the C-terminal amino acid of the X-motif or the C-terminal amino acid of the α- or γ-MSH is attached to the solid support material by means of a common linker such as 2,4-dimethoxy-4'-hydroxy-benzophenone, 4-(4-hydroxy-methyl-3-methoxyphenoxy)-butyric acid, 4-hydroxy-methylbenzoic acid, 4-hydroxymethyl-phenoxyacetic acid, 3-(4-hydroxymethylphenoxy)propionic acid, or p-{(R,S)-α-[1-(9H-Fluoren-9-γ1)-methoxyformamido]-2,4-dimethoxybenzyl}-phenoxyacetic acid (Rink amide linker).

Examples of suitable solid support materials (SSM) are e.g., functionalised resins such as polystyrene, polyacrylamide, polydimethylacrylamide, polyethyleneglycol, cellulose, polyethylene, polyethyleneglycol grafted on polystyrene, latex, dynabeads, etc.

The produced peptides of the invention are in some embodiment cleaved from the solid support material by means of an acid such as trifluoracetic acid, trifluoromethanesulfonic acid, hydrogen bromide, hydrogen chloride, hydrogen fluoride, etc. optionally in combination with one phenol, thioanisole, etc., or the peptide conjugate of the invention are in other embodiments cleaved from the solid support by means of a base such as ammonia, hydrazine, an alkoxide, such as sodium ethoxide, an hydroxide, such as sodium hydroxide, etc.

In other embodiments, the peptides of the invention may be prepared or produced by recombinant techniques. Thus, in one aspect of the present invention the peptide is produced by host cells comprising a first nucleic acid sequence encoding the peptide operably associated with a second nucleic acid capable of directing expression in said host cells. In some embodiments the second nucleic acid sequence comprise or even consist of a promoter that will direct the expression of protein of interest in said cells. A skilled person will be readily capable of identifying useful second nucleic acid sequences (e.g. vectors and plasmids) for use in a given host cell.

The process of producing a recombinant peptide in general comprises the steps of: providing a host cell, preparing a gene expression construct comprising a first nucleic acid encoding the peptide operably linked to a second nucleic acid capable of directing expression of said protein of interest in the host cell, transforming the host cell with the construct and cultivating the host cell, thereby obtaining expression of the peptide. In one embodiment of the invention, the recombinantly produced peptide is excreted by the host cells. The host cell include any suitable host cell known in the art, including prokaryotic cells, yeast cells, insect cells and mammalian cells.

In one embodiment, the recombinant peptide thus produced is isolated by any conventional method. The skilled person will be able to identify suitable protein isolation steps for purifying the peptide.

Medicament/Methods of Treatment

It is an aspect to provide α-MSH and γ-MSH-analogues as defined according to the present invention for use as a medicament.

In another aspect, the present invention provides methods for treatment, prevention or alleviation of an ischemic and/or inflammatory condition in the tissue of one or more organs as mentioned herein. Such methods according to the present invention in one embodiment comprise one or more steps of administration or release of an effective amount of a peptide according to the present invention, or a pharmaceutical composition comprising one or more such peptides, to an individual in need thereof. In one embodiment, such steps of administration or release according to the present invention is simultaneous, sequential or separate.

Ischemia is defined as a reduced/arrested blood flow to one or more organs resulting in a reduced oxygen delivery and/or utilization by the tissues. Ischemia induces multiple tissue reactions including neutrophil accumulation, other inflammatory responses and cell death. Ischemia is involved in multiple diseases, is associated with major surgery, and also occurs secondary to other severe diseases.

An individual in need as referred to herein, is in one embodiment an individual that benefits from the administration of a peptide or pharmaceutical composition according to the present invention. Such an individual in one embodiment suffers from an ischemic and/or inflammatory condition in the tissue of one or more organs, or is at risk of suffering therefrom. The individual is in one embodiment any human being, male or female, infant, middle-aged or old. The disorder to be treated or prevented in the individual in one embodiment relates to the age of the individual, the general health of the individual, the medications used for treating the individual and whether or not the individual has a prior history of suffering from diseases or disorders that may have or have induced ischemic and/or inflammatory conditions in the individual.

The terms "treatment" and "treating" as used herein refer to the management and care of a patient for the purpose of combating a condition, disease or disorder. The term is intended to include the full spectrum of treatments for a given condition from which the patient is suffering, such as administration of the peptide or composition for the purpose of: alleviating or relieving symptoms or complications; delaying the progression of the condition, partially arresting the clinical manifestations, disease or disorder; curing or eliminating the condition, disease or disorder; and/or preventing or reducing the risk of acquiring the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications. The patient to be treated is preferably a mammal, in particular a human being. Treatment of animals, such as mice, rats, dogs, cats, cows, horses, sheep and pigs, is, however, also within the scope of the present invention. The patients to be treated according to the present invention can be of various ages, for example, adults, children, children under 16, children age 6-16, children age 2-16, children age 2 months to 6 years or children age 2 months to 5 years.

The peptides referred to are the α-MSH and γ-MSH-analogues according to the present invention and described in detail herein above.

The invention is thus, in one embodiment, directed to a peptide according to the present invention for use in the treatment of an ischemic and/or inflammatory condition in the tissue of one or more organs of a mammal. In one embodiment said treatment is prophylactic, ameliorative and/or curative. In one embodiment, said mammal is a human (*homo sapiens*).

The invention in certain embodiments is also directed to a method for treatment of an ischemic and/or inflammatory condition in the tissue of one or more organs, said method comprising the step of administering a therapeutically effective amount of a peptide according to the present invention to an individual in need thereof.

In a specific embodiment, the invention is also directed to use of a peptide according to the present invention for manufacturing of a medicament for the treatment of an ischemic and/or inflammatory condition in the tissue of one or more organs of a mammal.

When referring to the tissue of one or more organs, said organ is in one embodiment selected from the group consisting of kidney, liver, brain, heart, muscles, bone marrow, skin, skeleton, lungs, the respiratory tract, spleen, exocrine glands, bladder, endocrine glands, reproduction organs including the phallopian tubes, eye, ear, vascular system, the gastroinstestinal tract including small intestines, colon, rectum, canalis analis and the prostate gland.

In one embodiment, the ischemic and/or inflammatory condition in the tissue of one or more organs is an acute, subacute or chronic condition.

In one embodiment, the ischemic and/or inflammatory condition in the tissue of one or more organs is an ischemic condition. In another embodiment, the ischemic and/or inflammatory condition in the tissue of one or more organs is an inflammatory condition.

In a further embodiment, the ischemic condition in the tissue of one or more organs is secondary ischemia.

Secondary ischemia is ischemia which is caused by an underlying condition such that the ischemia typically is secondary to e.g. stroke, injury, septic shock, systemic hypotension, cardiac arrest due to heart attack, cardiac arrhythmia, atheromatous disease with thrombosis, embolism from the heart or from blood vessel from any organ, vasospasm, aortic aneurysm or aneurisms in other organs, coronary stenosis, myocardial infarction, angina pectoris, pericarditis, myocarditis, myxodemia, or endocarditis.

An aortic aneurysm is in one embodiment thoracal or abdominal or dissecting aortic aneurysm. Systemic hypotension is in one embodiment hypotension due to heart disease, hypotension due to systemic disease including infection or allergic reactions, or hypotension due to one or more toxic compound or poison(s) or drug(s).

In one embodiment said ischemic and/or inflammatory condition in the tissue of one or more organs is due to (or caused by) a condition selected from stroke, injury, septic shock, systemic hypotension, cardiac arrest due to heart attack, cardiac arrhythmia, atheromatous disease with thrombosis, embolism from the heart or from blood vessel from any organ, vasospasm, aortic aneurysm or aneurisms in other organs, coronary stenosis, myocardial infarction, angina pectoris, pericarditis, myocarditis, myxodemia, or endocarditis.

In one embodiment, said ischemic condition is myocardial ischemia.

In one embodiment said ischemic and/or inflammatory condition in the tissue of one or more organs is due to cardiac arrhythmia. In one embodiment, said cardiac arrhythmia is the primary disease or secondary to another condition of the individual, including acute infections particularly those affecting the lungs, pulmonary embolism, hypotension, shock, anoxaemia and anaemia.

Cardiac arrhythmias include ventricular or supra ventricular tachyarrhythmias, atrioventricular block, sinus node disease, Wolff-Parkinson-White syndrome, Lenegres disease, Lev's disease any syndrome involving an abnormal myocardial connection between atrium and ventricle.

In one embodiment, secondary Ischemia can also be observed in connection with a range of other diseases and conditions, including but not limited to diabetes mellitus, hyperlipidaemia, thromboangiitis obliterans, Takayasu's syndrome, arteritis temporalis, mucocutaneous lymph node syndrome (Kawasaki disease), cardiovascular syphilis, connective tissue disorders such as Raynaud's disease, phlegmasia coerulae dolens, blood vessel trauma including iatrogene trauma such as cannulation, conditions with increased fasting levels of LDL-Cholesterol, triglycerid, and/or HDL-Cholesterol, retroperitoneal fibrosis, rheumatic diseases, systemic lupus erythematosus, polyarteritis nodosa, scleroderma, polymyositis, dermatomyositis, rheumatoid arthritis, neuromyopathic disorders such as progressive muscular dystrophy of Duchenne, Friedreich's ataxia, and myotonic dystrophy, anaphylaxis, serum sickness, hemolytic anaemia, allergy, and allergic agranulocytosis. In one embodiment the peptides of the present invention are also be useful in the treatment or prevention of said conditions.

Many infections may have an influence on the tissue and disturb the normal function resulting in decreased performance, which in one embodiment is treated by administration of an effective dose of a peptide of the invention. In one embodiment, infections include infections by protozoa, virus, bacteria and fungus and include conditions such as AIDS, bacterial septicemia, systemic fungal infections. Rickettsial diseases, toxic shock syndrome, infectious mononucleosis, *chlamydia thrachomatis, chlamydia psittaci*, cytomegalovirus infection, *Campylobacter, salmonella*, influenza, poliomyelitis, toxoplasmosis, Lassa Fever, Yellow Fever, billharziose, colibacteria, *enterococcus, preteus, klebsiella, pseudomonas, staphylococcus aureus, staphylococcus epidermidis, Candida albicans*, tuberculosis, mumps, infectious mononucleosis, hepatitis and Coxackie virus.

In one embodiment the condition to be treated is caused by a cancer or a by premalignant disorder having an impact on the organ, e.g. on the respiratory system including lung, bronchiole, upper airways, and/or on the heart and/or on the kidney and/or on the gastrointestinal system, including acute leukemia, chronic myelocytic leukemia, chronic lymphocytic leukemia, Hodgkin's disease, lymphosarcoma, myeloma, metastasizing carcinoma of any origin. In one embodiment the peptides of the invention are used in the treatment or prevention of said conditions.

In one embodiment, the ischemic and/or inflammatory condition in the tissue of one or more organs is caused by a physical trauma including electromagnetic radiation.

Surgery and Transplantation

Major surgical interventions including cardiothoracic surgery, abdominal surgery, surgery on the aorta and other major blood vessels, as well as organ transplantation such as lung or heart or combined lung and heart transplantation, liver transplantation or renal transplantation induce a systemic inflammatory response (SIR; or systemic inflammatory response syndrome SIRS) and is associated with post-surgical organ dysfunction including development of renal failure.

Renal failure is a consequence of the SIR and the reduced blood flow generated during the surgical intervention. The result is post-surgical acute kidney injury (AKI) which for a large fraction deteriorates into chronic renal failure. Currently no efficient treatment modality exists to prevent the development of renal failure. Post-surgical renal failure may be defined as a more than 25% reduction in Glomerular filtration rate (GFR) present 3 month after the surgical intervention.

Major cardiac surgery such as repair of one or more cardiac valves, cardiac artery bypass grafting (CABG), surgery on the aortic root, or aortic branch including the common carotid arteries, or combined cardiac surgery such as valve(s) replacement and CABG and/or aortic root surgery is associated with development of renal impairment that, when present, is associated with increased morbidity and mortality.

In one embodiment, treatment with an αMSH or a γMSH analogue according to the present invention reduce the degree of renal impairment. In one embodiment this is achieved by reducing the fall in GFR post-surgery; by reducing the degree of post-surgical increases in serum creatinine or cystatin C or the more immediate increases in urinary excretion of AKI markers NGAL, IL18 or KIM-1; and/or or by reducing the degree of post-surgical SIR (for example by reduced circulating levels of IL-6 and other proinflammatory markers).

Lung transplantation (LTX) is the ultimate treatment modality for end-stage lung disease. The major challenges associated with LTX are scarcity of donors, acute and chronic rejection of the transplanted lungs and side-effects of immune suppressive treatment including development of chronic renal failure (CRF).

While there has been a good development in the treatment of acute rejection by newer immunosuppressive drugs leading to fewer episodes of acute rejection within the first year, fewer organ losses, fewer side effects, fewer infections, and less invasive monitoring methods, the control of chronic organ rejection has not greatly improved and the half-life time in terms of how many years 50% of the patients survive has only marginally improved during the last 2 decades to around 7 years.

Side effects of the immunosuppressive treatment are dominated by 2 major challenges: Nephrotoxicity and post-transplant lymphoproliferative diseases (PTLD), where the latter can be considered as a consequence of the degree of immune-suppression needed to avoid chronic organ rejection—"too much" keeps the rejection on distance, but gives infections and PTLD, while giving "too little" puts the patients at an increased risk of rejecting the graft. Neprotoxicity and development of CRF is despite of extensive research during the last 30 years, still a significant problem. Five years after LTX none of the patients retain normal kidney function and 20% of the long term survivors will end with a kidney transplant as well.

Calcineurin inhibitor treatment (Tacrolimus, Cyclosporin A) is the corner-stone in the immune suppressive treatment strategy for successful solid organ transplantation. The limiting factor in using calcineurin inhibitors is the acute and chronic irreversible nephrotoxicity, Recent data indicate that kidney function (measured as reduction in GFR) is reduced with 40% within the first 14 days after LTX and that this reduction is irreversible.

Heart transplantation (HTX) is the ultimate treatment modality for end-stage heart failure. As for LTX the major challenges associated with HTX are scarcity of donors, acute and chronic rejection of the transplanted hearts and side-effects of immune suppressive treatment including development of CRF. Like for LTX the number of patients with retained kidney function over time is limited or absent and like LTX a major reduction i kidney function is present already two to four weeks post transplantation.

This dramatic effect on kidney function seen after LTX and HTX is probably not caused by calcineurin inhibitor treatment alone, but is the final result of the surgical and anesthesiological trauma in combination with the organ ischemia and side effects of antibiotic, antiviral, antifungal and immunosuppressive drugs. Consequently, in one embodiment pharmacological intervention by employment of the αMSH and γMSH analogues according to the present invention will reduce the degree of renal impairment associated with organ transplantation, such as LTX and HTX.

Surgery, as is outlined herein above in detail, including organ transplantation, may thus be the cause of secondary ischemia.

The invention is thus in one embodiment directed to a peptide according to the present invention for use in the treatment of an ischemic and/or inflammatory condition in the tissue of one or more organs of a mammal, wherein said ischemic and/or inflammatory condition is associated with surgery. In one embodiment said surgery is major surgery or major surgical intervention.

In one embodiment, said surgery is selected from the group consisting of cardiothoracic surgery, abdominal surgery, surgery on the aorta and/or other major blood vessels, repair of one or more cardiac valves, cardiac artery bypass grafting (CABG), surgery on the aortic root or the aortic branch including the common carotid arteries, and combined cardiac surgery such as valve(s) replacement and CABG and/or aortic root surgery.

In one embodiment, said surgery encompasses surgical insertion transplants, devices, grafts, prostheses or other biomedical compounds or devices inserted by surgical operations.

In one embodiment, said major surgery comprises organ transplantation. It follows that the invention in one embodiment is directed to a peptide according to the present invention for use in the treatment of an ischemic and/or inflammatory condition in the tissue of one or more organs of a mammal, wherein said ischemic and/or inflammatory condition is associated with organ transplantation. In one embodiment, said organ transplantation is solid organ transplantation.

In one embodiment said solid organ transplantation is heart transplantation, lung transplantation, combined heart and lung transplantation, liver transplantation or kidney (renal) transplantation.

The invention in another embodiment is directed to a peptide according to the present invention for use in the treatment of post-surgical systemic inflammatory response syndrome (SIRS), post-surgical organ dysfunction and/or post-surgical renal failure such as acute kidney injury (AKI), neprotoxicity and/or chronic renal failure (CRF).

The invention is in one embodiment directed to a peptide according to the present invention for reducing the degree of renal impairment associated with major surgery, in one embodiment organ transplantation.

Reperfusion injury is tissue damage caused when blood supply returns to the tissue after a period of ischemia or lack of oxygen. The absence of oxygen and nutrients from blood during the ischemic period creates a condition in which the restoration of circulation results in inflammation and oxidative damage through the induction of oxidative stress rather than restoration of normal function.

Reperfusion injuries may occur in connection with surgery, such as major surgical interventions including organ transplantations. It is a primary concern when performing liver transplantations, and also during cardiac surgery.

In a particular embodiment, said ischemic and/or inflammatory condition in the tissue of one or more organs is associated with reperfusion injury. Thus, in one embodiment the present invention is directed to a peptide according to the present invention for use in the treatment of an ischemic and/or inflammatory condition in the tissue of one or more organs of a mammal, wherein said ischemic and/or inflammatory condition is associated with reperfusion injury.

In some embodiments, the peptides or compositions of the present invention are to be administered before and/or during surgery and/or organ transplantation.

Toxins and Drugs

In one embodiment the ischemic and/or inflammatory condition in the tissue of one or more organs as described herein is caused by toxin- or drug-induced cell, tissue or organ failure.

The invention is thus in one embodiment directed to a peptide according to the present invention for use in the treatment of an ischemic and/or inflammatory condition in the tissue of one or more organs of a mammal, wherein said ischemic and/or inflammatory condition is caused (or induced) by toxin- or drug-induced cell, tissue or organ failure.

Said drug includes but are not restricted to cancer chemotherapeutics including cisplatin, carboplatin, dacarbezine, procarbazine, altretamine, semustine, lomustine, carmustine, busulfan, thiotepa, melphalan, cyclophosphamide, chlorambucil, mechlorethamine, azadtidine, cladrrbine, cytorabine, fludarabine, fluorouracil, mercaptopurine, metrotrexate, thioguanine, allopunnol, bleomycin, dactinomycin, daunorubicin, docetaxel, doxorubicin (adriamycin), etoposide, idarubicin, irinotecan, mitomycin, paclitaxel, plicamycin, topotecan, vinblastine, vincristine, vinorelbine, amasacrine, asparaginase, hydroxyurea, mititane, mitoxantrone; Antibiotics as aminoglycosides including streptomycin, neomycin, kanamycin, amikacin, gentamicin, tobramycin, sisomicin and nitilmicin; immunodepressive compounds as cyclosporine; tricyclic antidepressants, lithium salts, prenylamine and phenothizine derivatives.

Inflammatory Conditions

Inflammation is a localized defensive response of the body against pathogens and injury. Immune cells and soluble factors take part in this process to neutralize the injurious agent and initiate tissue repair to restore homeostasis. Loss of regulation of these mechanisms can prevent the final resolution of the inflammatory process, leading to chronic inflammation. Chronic inflammation is extremely relevant in today's modem medicine, as it contributes to the pathogenesis of the most important diseases of the industrialized societies including atherosclerosis, acute and chronic heart failure, cancer, diabetes, and obesity-associated diseases. Recent insight into endogenous anti-inflammatory pathways have identified a number of natural anti-inflammatory and pro-resolving molecules and pathways suitable for pharmacological intervention that would make it possible to develop drugs that mimic the natural course of resolving inflammation. Among these natural anti-inflammatory and pro-resolving pathways is the melanocortin system.

The anti-inflammatory effects of melanocortins are exerted through inhibition of inflammatory mediators and by inhibition of inflammatory cell migration. Melanocortins exert these effects in a variety of cells including monocytes, macrophages, subtypes of T-cells, endothelial cells and epithelial cells.

Most cell types responsive to the anti-inflammatory effect of melanocortins express the MCr1, ie monocytes, macrophages, neutrophils, mast cells, fibroblasts, dendritic cells, astrocytes, and microglia. Both human and murine macrophages express the MCr3 and an increasing number of reports have identified MC3r mediated anti-inflammatory effects in vitro and in vivo in models of both acute and more sustained/chronic inflammation.

Consequently, in one embodiment anti-inflammatory intervention targeting the melanocortin system would benefit from targeting both the MC1r and MC3r.

Joint diseases such as rheumatoid arthritis (RA) and gout are characterized by episodes with acute exacerbations, in RA the exacerbations (often described as flairs) typically develop on top of chronic symptoms and develop despite intense pharmacological treatment. A similar pattern can be seen in gout, with the major difference that most gout patients are without symptom between the exacerbations. In both conditions significant neutrophil infiltration into the synovial membrane and joint fluid are the primary pathological hallmark of the exacerbations. The most important pro-inflammatory effectors involved include IL-1β, TNF-α, IL-6, IL-8, and COX-2. Resolution of the acute exacerbations to avoid development or deterioration of chronic inflammation involves activation of macrophages to phagocyte the apoptotic neutrophils.

Melanocortin type 1 and 3 receptors are expressed in synovial tissue of both animals and humans and it appears that the MC3r is upregulated in RA patients with active disease.

Consequently in one embodiment it would be attractive to apply treatment with an αMSH or a γMSH analogue according to the present invention to joint diseases, not at least in order to reduce the severity of exacerbations in existing disease as flairs in rheumatoid arthritis would have major clinical impact. However, not only joint diseases are associated with exacerbations of symptoms. Neurodegenerative diseases such as multiple sclerosis have flair-like exacerbations where treatment with an αMSH or a γMSH analogue according to the present invention in one embodiment could reduce the symptoms and eventually as for Joint diseases reduce the overall deterioration of the patients functional level.

The invention is thus in one embodiment directed to a peptide according to the present invention for use in the treatment of an inflammatory condition in the tissue of one or more organs of a mammal, wherein said ischemic and/or inflammatory condition is an inflammatory disease.

In one embodiment, said inflammatory disease is Arthritis. In one embodiment, said inflammatory disease is selected from the group consisting of an arthropathy (a disease of a joint, Arthritis (including diseases associated with arthritis), osteoartritis, rheumatoid arthritis; spondylarthropathies (e.g. ankylosing spondilitis), reactive arthritis (including arthritis following rheumatic fever), Henoch-Schonlein purpura, Reiter's disease, Juvenile Chronic arthritis including Still's disease, juvenile rheumatoid arthritis, juvenile ankylosing spondylitis, psoriasis, osteoarthritis, osteoarthritis secondary to hypermobilty, congenital dysplasias, slipped femoral epiphysis, Perthes' disease, intra-articular fractures, meniscectomy, obesity, recurrent dislocation, repetitive actions, crystal depositions and diseases and metabolic abnormalities of cartilage including pyrophosphate arthropathy, ochronosis, haemochromatosis, avascular necrosis including Sickle Cell disease, therapy with corticoids or other drugs, Caisson disease, septic or infectious arthritis (including tuberculous arthritis, meningococcal arthritis, gonococcal arthritis, *salmonella* arthritis), infective endocarditis, viral arthritis, recurrent haemarthrosis, and all kinds of deposition diseases such as Gout, pyrophosphate arthopathy and acute calcific periarthritis.

In one embodiment, said inflammatory disease is a connective tissue disorder; in one embodiment selected from the group consisting of systemic lupus erythematosus, polymyositis/dermatomyositis, systemic sclerosis, mixed connective tissue disease, sarcoidosis and primary Sjogrens syndrome including keratoconjunctivitis sicca, polymyalgia rheumatica, and other types of vasculitis, crystal deposition diseases (including gout), pyrophosphate arthropathy, and acute calcific periarthritis.

In one embodiment, said inflammatory disease is a soft-tissue rheumatism including bursitis, tenosynovitis or peritendonitis, enthesitis, nerve compression, periarthritis or capsulitis, muscle tension and muscle dysfunction.

In one embodiment, said inflammatory disease is selected from the group consisting of vasculitis including vasculitis secondary to rheumatoid arthritis, infective vasculitis due to infections with bacterial species including spirochaetal diseases as Lyme disease, syphilis, rickettsial and mycobacterial infections, fungal, viral or protozoal infections, non-infective vasculitis secondary to hypersensibility and leucocytoplastic vasculitis including Serum Sickness and Henoch-Schonlein purpura, Drug induced vasculitis, essential mixed cryoglobulinaemia, hypocomplentaemia, Vasculitis associated with other kinds of malignancy, non-infective vascultitis including Takayasu's arteritis/disease, Giant Cell Arteritis (Temporal arteritis and polymyalgia rheumatica), Buerger's disease, polyarteritis nodosa, microscopic polyarteritis, Wegener's granulomatose, Churg-Strauss syndrome, and vasculitis secondary to connective tissue diseases including Systemic Lupus Erythematosus, Polymyositis/Dermatomyositis, Systemic Sclerosis, Mixed Connetive Tissue Disease, sarcoidosis and Primary Sjogrens syndrome.

In one embodiment, said inflammatory disease is inflammatory diseases of the gastrointestinal system. Said inflammatory diseases of the gastrointestinal system may be selected from the group consisting of inflammatory bowel disease, coeliac disease, gluten sensitive enteropathy, eosinophilic gastroenteritis, intestinal lympangiectasia, inflammatory bowel disease (including Chrohn's disease and ulcerative colitis), diverticular disease of the colon, radiation enteritis, irritable bowel syndrome, Whipple's diease, stomatitis of all kinds, salivary gland diseases (such as sarcoidosis, salivary duct obstruction and Sjogrens syndrome), inflammation of the oesophagus (e.g. due to gastro-oesophagel reflux or infections with *Candida* species, herpes simplex and cytomegalus virus), inflammatory diseases of the stomach (including acute and chronic gastritis, *helicobacter pylori* infection and Mentriers disease), and inflammation of the small intestine.

In one embodiment, said Inflammatory disease is a neurodegenerative disease, such as a neurodegenerative disease having an inflammatory component, such as multiple sclerosis (MS).

In one embodiment, said inflammatory disease is selected from the group consisting of dermatitis, pemfigus, bulloid pemphigoid, benign mucous membrane pemphigoid, dermatitis herpitiformis, tropical sprue, systemic amyloidosis, primary biliary cirrhosis, Goodpasture syndrome, all kinds of deposition diseases as Gout, pyrophosphate arthopathy and acute calcific periarthritis, pancreatitis, septic discitis, tuberculosis, malignancies (such as matastases, myeloma and others), spinal tumours, ancylosing spondylitis, acute disc prolapse, chronic disc disease/osteoarthritis, osteoporosis, and osteomalacia, Pagets disease, hyperparathyroidism, renal osteodystrophy, spondylolisthesis, spinal stenosis congenital abnormalities and fibromyalgia.

In one embodiment, said inflammatory disease is selected from the group consisting of upper and lower airway diseases such as chronic obstructive pulmonary diseases (COPD), allergic and non-allergic asthma, allergic rhinitis, allergic and non-allergic conjunctivitis, allergic and non-allergic dermatitis and lung inflammation.

Second Active Ingredients

In some embodiments, the peptides of the present invention are combined with or comprise one or more second active ingredients which are understood as other therapeutical compounds or pharmaceutically acceptable derivatives thereof.

Methods for treatment according to the present invention in one embodiment thus further comprise one or more steps of administration of one or more second active ingredients, either concomitantly or sequentially, and in any suitable ratios. In one embodiment, such second active ingredients is, for example, selected from compounds used to treat or prevent ischemic and/or inflammatory condition in the tissue of one or more organs or symptoms and complications associated with ischemic and/or inflammatory condition in the tissue of one or more organs.

Methods of treatment according to the present invention in one embodiment include a step wherein the pharmaceutical composition or peptide as defined herein is administered simultaneously, sequentially or separately in combination with one or more second active ingredients.

Kit of Parts

In one embodiment the present invention provides a kit of parts. A kit of parts according to the present invention in one embodiment comprises one or more of the peptides or compositions as defined herein for treatment, prevention or alleviation of ischemic and/or inflammatory condition in the tissue of one or more organs. Kits according to the present invention in one embodiment allows for simultaneous, sequential or separate administration of peptides or second active ingredients as described herein.

In one embodiment of the present invention, the kit of parts comprises one or more second active ingredients as described herein.

Administration and Dosage

According to the present invention, a composition comprising a MSH-analogue as defined herein is in one embodiment administered to individuals in need of treatment in pharmaceutically effective doses or a therapeutically effective amount.

A therapeutically effective amount of a peptide according to the present invention is in one embodiment an amount sufficient to cure, prevent, reduce the risk of, alleviate or partially arrest the clinical manifestations of a given disease or disorder and its complications. The amount that is effective for a particular therapeutic purpose will depend on the severity and the sort of the disorder as well as on the weight and general state of the subject. An amount adequate to accomplish this is defined as a "therapeutically effective amount".

In one embodiment of the present invention, the composition is administered in doses of from 1 µg/day to 100 mg/day; such as from 1 µg/day to 10 µg/day, such as 10 µg/day to 100 µg/day, such as 100 µg/day to 250 µg/day, such as 250 µg/day to 500 µg/day, such as 500 µg/day to 750 µg/day, such as 750 µg/day to 1 mg/day, such as 1 mg/day to 2 mg/day, such as 2 mg/day to 5 mg/day, or such as 5 mg/day to 10 mg/day, such as 10 mg/day to 20 mg/day, such as 20 mg/day to 30 mg/day, such as 30 mg/day to 40 mg/day, such as 40 mg/day to 50 mg/day, such as 50 mg/day to 75 mg/day, or such as 75 mg/day to 100 mg/day.

In one embodiment of the present invention, one single dose of the composition is administered and may comprise of from 1 µg/kg body weight to 100 mg/kg body weight; such as from 1 to 10 µg/kg body weight, such as 10 to 100 µg/day, such as 100 to 250 µg/kg body weight, such as 250 to 500 µg/kg body weight, such as 500 to 750 µg/kg body weight, such as 750 µg/kg body weight to 1 mg/kg body weight, such as 1 mg/kg body weight to 2 mg/kg body weight, such as 2 to 5 mg/kg body weight, such as 5 to 10 mg/kg body weight, such as 10 to 20 mg/kg body weight, such as 20 to 30 mg/kg body weight, such as 30 to 40 mg/kg body weight, such as 40 to 50 mg/kg body weight, such as 50 to 75 mg/kg body weight, or such as 75 to 100 mg/kg body weight.

In one embodiment, a dose according to the present invention is administered one or several times per day, such as from 1 to 6 times per day, such as from 1 to 5 times per day, such as from 1 to 4 times per day, such as from 1 to 3 times per day, such as from 1 to 2 times per day, such as from 2 to 4 times per day, such as from 2 to 3 times per day. In one embodiment, the composition comprising a peptide according to the invention is administered preoperatively (before operation or surgery) and/or peroperatively (during operation or surgery).

Routes of Administration

It will be appreciated that the preferred route of administration will depend on the general condition and age of the subject to be treated, the nature of the condition to be treated, the location of the tissue to be treated in the body and the active ingredient chosen.

In one embodiment of the present invention, the route of administration allows for the peptide to cross the blood-brain barrier.

Systemic Treatment

In one embodiment, the route of administration allows for introducing the peptide into the blood stream to ultimately target the sites of desired action.

In one embodiment the routes of administration is any suitable routes, such as an enteral route (including the oral, rectal, nasal, pulmonary, buccal, sublingual, transdermal, intracisternal and intraperitoneal administration), and/or a parenteral route (including subcutaneous, intramuscular, intrathecal, intravenous and intradermal administration).

Appropriate dosage forms for such administration may be prepared by conventional techniques.

Parenteral Administration

Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration or subcutaneous administration. Furthermore, parenteral administration includes inhalations and topical administration.

Accordingly, the peptide or composition is in one embodiment administered topically to cross any mucosal membrane of an animal to which the substance or peptide is to be given. e.g. in the nose, vagina, eye, mouth, genital tract, lungs, gastrointestinal tract, or rectum, for example the mucosa of the nose, or mouth, and accordingly, parenteral administration may also include buccal, sublingual, nasal, rectal, vaginal and intraperitoneal administration as well as pulmonal and bronchial administration by inhalation or installation. In some embodiments, the peptide is administered topically to cross the skin.

In one embodiment, the intravenous, subcutaneous and intramuscular forms of parenteral administration are employed.

Local Treatment

In one embodiment, the peptide or composition according to the invention is used as a local treatment, i.e. is introduced directly to the site(s) of action. Accordingly, the peptide may be applied to the skin or mucosa directly, or the peptide may be injected into the site of action, for example into the diseased tissue or to an end artery leading directly to the diseased tissue.

Pharmaceutical Formulations

In one embodiment, the peptides according to the present invention or pharmaceutically acceptable derivatives thereof are administered alone or in combination with pharmaceutically acceptable carriers or excipients, in either single or multiple doses. The pharmaceutical compositions or compounds according to the invention may be formulated with pharmaceutically acceptable carriers or diluents as well as any other known adjuvants and excipients in accordance with conventional techniques such as those disclosed in Remington: The Science and Practice of Pharmacy, 20$^{th}$ Edition, Gennaro, Ed., Mack Publishing Co., Easton, Pa., 2000.

The term "pharmaceutically acceptable derivative" in present context includes pharmaceutically acceptable salts, which indicate a salt which is not harmful to the patient. Such salts include pharmaceutically acceptable basic or acid addition salts as well as pharmaceutically acceptable metal salts, ammonium salts and alkylated ammonium salts. A pharmaceutically acceptable derivative further includes esters and prodrugs, or other precursors of a compound which may be biologically metabolized into the active compound, or crystal forms of a compound.

The pharmaceutical composition or pharmaceutically acceptable composition may be specifically formulated for administration by any suitable route, such as an enteral route, the oral, rectal, nasal, pulmonary, buccal, sublingual, transdermal, intracisternal, intraperitoneal, and parenteral (including subcutaneous, intramuscular, intrathecal, intravenous and intradermal) route.

In an embodiment of the present invention, the pharmaceutical compositions or compounds of the present invention are formulated for crossing the blood-brain-barrier.

Pharmaceutical compositions for oral administration include solid dosage forms such as hard or soft capsules, tablets, troches, dragees, pills, lozenges, powders and granules. Where appropriate, they can be prepared with coatings such as enteric coatings, or they can be formulated so as to provide controlled release of the active ingredient, such as sustained or prolonged release, according to methods well known in the art. In the same solid dosage form two active ingredients may be combined so as to provide controlled release of one active ingredient and immediate release of another active ingredient.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions, as well as sterile powders to be reconstituted in sterile injectable solutions or dispersions prior to use. Depot injectable formulations are also regarded as being within the scope of the present invention.

Other suitable administration forms include suppositories, sprays, ointments, cremes/lotions, gels, inhalants, dermal patches, implants, etc.

In one embodiment, a compound or peptide for use according to the present invention is generally utilized as the free substance or as a pharmaceutically derivative such as a pharmaceutically acceptable ester or such as a salt thereof. Examples of the latter are: an acid addition salt of a compound having a free base functionality, and a base addition salt of a compound having a free acid functionality. The term "pharmaceutically acceptable salt" refers to a non-toxic salt of a compound for use according to the present invention, which salts are generally prepared by reacting a free base with a suitable organic or inorganic acid, or by reacting an acid with a suitable organic or inorganic base. When a compound for use according to the present invention contains a free base functionality, such salts are prepared in a conventional manner by treating a solution or suspension of the compound with a chemical equivalent of a pharmaceutically acceptable acid. When a compound for use according to the present invention contains a free acid functionality, such salts are prepared in a conventional manner by treating a solution or suspension of the compound with a chemical equivalent of a pharmaceutically acceptable base. Physiologically acceptable salts of a compound with a hydroxy group include the anionic form of the compound in combination with a suitable cation, such as sodium or ammonium ion. Other salts which are not pharmaceutically acceptable may be useful in the preparation of compounds of the invention, and these form a further aspect of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

In one embodiment of the present invention, the peptides of the present invention are on crystalline forms, for example co-crystallized forms or hydrates of crystalline forms.

The term "prodrug" refers to peptides that are rapidly transformed in vivo to yield the parent compound of the above formulae, for example, by hydrolysis in blood or by metabolism in cells, such as for example the cells of the basal ganglia. A thorough discussion is provided in T. Higuchi and V Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference. Examples of prodrugs include pharmaceutically acceptable, non-toxic esters of the compounds of the present invention. Esters of the compounds of the present invention may be prepared according to conventional methods "March's Advanced Organic Chemistry, 5$^{th}$ Edition". M. B. Smith & J. March, John Wiley & Sons, 2001.

In one embodiment, for parenteral administration, solutions of peptides for use according to the present invention in sterile aqueous solution, in aqueous propylene glycol or in sesame or peanut oil are employed. Aqueous solutions should be suitably buffered where appropriate, and the liquid diluent rendered isotonic with, e.g., sufficient saline or glucose. Aqueous solutions are particularly suitable for intravenous, intramuscular, subcutaneous and intraperitoneal administration. The sterile aqueous media to be employed are all readily available by standard techniques known to those skilled in the art.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Moreover, the carrier or diluent may include any sustained release material known in the art, such as glyceryl monostearate or glyceryl distearate, alone or mixed with a wax. The pharmaceutical compositions formed by combining the compounds for use according to the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units, such as capsules or tablets, which each contain a predetermined amount of the active ingredient, and which may include a suitable excipient.

Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavouring agents, colouring agents and preserving agents in order to provide pharmaceutically elegant and palatable preparations. Tablets may contain the active ingredient(s) in admixture with non-toxic pharmaceutically acceptable excipients which are suitable for the manufacture of tablets. These excipients may, for example, be: inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, the contents of which are incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsules wherein the active ingredient is mixed with water or an oil medium, for example peanut oil, liquid paraffin, or olive oil. Aqueous suspensions may contain the compound for use according to the present invention in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising peptides for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agent. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the compound with a suitable non-irritating excipient which is solid at ordinary temperatures but liquid at the rectal temperature and will thus melt in the rectum to release the drug. Such materials include, for example, cocoa butter and polyethylene glycols.

Peptides of the present invention may also be administered in the form of liposome delivery systems, such as small unilamellar vesicles, large unilamellar vesicles, and multi-lamellar vesicles. Liposomes may be formed from a variety of phospholipids, such as but not limited to cholesterol, stearylamine or phosphatidylcholines.

In addition, some peptides of the present invention may form solvates with water or common organic solvents. Such solvates are also encompassed within the scope of the invention.

Thus, a further embodiment provides a pharmaceutical composition comprising a peptide for use according to the present invention, or a pharmaceutically acceptable salt, solvate, or prodrug thereof, and one or more pharmaceutically acceptable carriers, excipients, or diluents.

APPENDIX

Examples of sequences of MSH analogues

```
a-MSH analogues
X = Ac-(Ac-Lys-Lys)Lys-:
Ac-(Ac-Lys-Lys)Lys-Ser-Tyr-Ser-Met-Glu-Phe-Arg-Trp-Gly-Lys-Pro-Val  (Ac-(Ac-
Lys-Lys)Lys-SEQ ID NO: 1)
Ac-(Ac-Lys-Lys)Lys-Ser-Tyr-Ser-Met-Glu-His-(D-Phe)Arg-Trp-Gly-Lys-Pro-Val
Ac-(Ac-Lys-Lys)Lys-Ser-Tyr-Ser-Met-Glu-His-Phe-(D-Arg)-Trp-Gly-Lys-Pro-Val
Ac-(Ac-Lys-Lys)Lys-Ser-Tyr-Ser-Met-Glu-His-Phe-Arg-(D-Trp)-Gly-Lys-Pro-Val
Ac-(Ac-Lys-Lys)Lys-Ser-Tyr-Ser-Met-Glu-His-(D-Phe)-Arg-(D-Trp)-Gly-Lys-Pro-Val
Ac-(Ac-Lys-Lys)Lys-Ser-Tyr-Ser-Met-Glu-His-Nal-Arg-Trp-Gly-Lys-Pro-Val
Ac-(Ac-Lys-Lys)Lys-Ser-Tyr-Ser-Met-Glu-His-(D-Nal)-Arg-Trp-Gly-Lys-Pro-Val
Ac-(Ac-Lys-Lys)Lys-Ser-Tyr-Ser-Met-Glu-His-Phe-Arg-Trp-Gly-Lys-Pro-(D-Val)
Ac-(Ac-Lys-Lys)Lys-Ser-Tyr-Ser-Met-Glu-His-(D-Phe)-Arg-Trp-Gly-Lys-Pro-(D-Val)
Ac-(Ac-Lys-Lys)Lys-Ser-Tyr-Ser-Met-Glu-His-Phe-(D-Arg)-Trp-Gly-Lys-Pro-(D-Val)
Ac-(Ac-Lys-Lys)Lys-Ser-Tyr-Ser-Met-Glu-His-Phe-Arg-(D-Trp)-Gly-Lys-Pro-(D-Val)
Ac-(Ac-Lys-Lys)Lys-Ser-Tyr-Ser-Met-Glu-His-(D-Phe)-Arg-(D-Trp)-Gly-Lys-Pro-(D-Val)
Ac-(Ac-Lys-Lys)Lys-Ser-Tyr-Ser-Met-Glu-His-Nal-Arg-Trp-Gly-Lys-Pro-(D-Val)
Ac-(Ac-Lys-Lys)Lys-Ser-Tyr-Ser-Met-Glu-His-(D-Nal)-Arg-Trp-Gly-Lys-Pro-(D-Val)
Ac-(Ac-Lys-Lys)Lys-Ser-Tyr-Ser-Nle-Glu-His-Phe-Arg-Trp-Gly-Lys-Pro-Val  (Ac-(Ac-
Lys-Lys)Lys-SEQ ID NO: 3)
Ac-(Ac-Lys-Lys)Lys-Ser-Tyr-Ser-Nle-Glu-His-(D-Phe)-Arg-Trp-Gly-Lys-Pro-Val
Ac-(Ac-Lys-Lys)Lys-Ser-Tyr-Ser-Nle-Glu-His-Phe-(D-Arg)-Trp-Gly-Lys-Pro-Val
Ac-(Ac-Lys-Lys)Lys-Ser-Tyr-Ser-Nle-Glu-His-Phe-Arg-(D-Trp)-Gly-Lys-Pro-Val
Ac-(Ac-Lys-Lys)Lys-Ser-Tyr-Ser-Nle-Glu-His-(D-Phe)-Arg-(D-Trp)-Gly-Lys-Pro-Val
Ac-(Ac-Lys-Lys)Lys-Ser-Tyr-Ser-Nle-Glu-His-Nal-Arg-Trp-Gly-Lys-Pro-Val
Ac-(Ac-Lys-Lys)Lys-Ser-Tyr-Ser-Nle-Glu-His-(D-Nal)-Arg-Trp-Gly-Lys-Pro-Val
Ac-(Ac-Lys-Lys)Lys-Ser-Tyr-Ser-Nle-Glu-His-Phe-Arg-Trp-Gly-Lys-Pro-(D-Val)
Ac-(Ac-Lys-Lys)Lys-Ser-Tyr-Ser-Nle-Glu-His-(D-Phe)-Arg-Trp-Gly-Lys-Pro-(D-Val)
Ac-(Ac-Lys-Lys)Lys-Ser-Tyr-Ser-Nle-Glu-His-Phe-(D-Arg)-Trp-Gly-Lys-Pro-(D-Val)
Ac-(Ac-Lys-Lys)Lys-Ser-Tyr-Ser-Nle-Glu-His-Phe-Arg-(D-Trp)-Gly-Lys-Pro-(D-Val)
Ac-(Ac-Lys-Lys)Lys-Ser-Tyr-Ser-Nle-Glu-His-(D-Phe)-Arg-(D-Trp)-Gly-Lys-Pro-(D-Val)
Ac-(Ac-Lys-Lys)Lys-Ser-Tyr-Ser-Nle-Glu-His-Nal-Arg-Trp-Gly-Lys-Pro-(D-Val)
```

APPENDIX-continued

Examples of sequences of MSH analogues

```
Ac-(Ac-Lys-Lys)Lys-Ser-Tyr-Ser-Nle-Glu-His-(D-Nal)-Arg-Trp-Gly-Lys-Pro-(D-Val)
Ac-(Ac-Lys-Lys)Lys-Ser-Ser-Ile-Ile-Ser-His-Phe-Arg-Trp-Gly-Lys-Pro-Val (Ac-(Ac-Lys-
Lys)Lys-SEQ ID NO: 5)
Ac-(Ac-Lys-Lys)Lys-Ser-Ser-Ile-Ile-Ser-His-(D-Phe)-Arg-Trp-Gly-Lys-Pro-Val
Ac-(Ac-Lys-Lys)Lys-Ser-Ser-Ile-Ile-Ser-His-Phe-(D-Arg)-Trp-Gly-Lys-Pro-Val
Ac-(Ac-Lys-Lys)Lys-Ser-Ser-Ile-Ile-Ser-His-Phe-Arg-(D-Trp)-Gly-Lys-Pro-Val
Ac-(Ac-Lys-Lys)Lys-Ser-Ser-Ile-Ile-Ser-His-(D-Phe)-Arg-(D-Trp)-Gly-Lys-Pro-Val
Ac-(Ac-Lys-Lys)Lys-Ser-Ser-Ile-Ile-Ser-His-Nal-Arg-Trp-Gly-Lys-Pro-Val
Ac-(Ac-Lys-Lys)Lys-Ser-Ser-Ile-Ile-Ser-His-(D-Nal)-Arg-Trp-Gly-Lys-Pro-Val
Ac-(Ac-Lys-Lys)Lys-Ser-Ser-Ile-Ile-Ser-His-Phe-Arg-Trp-Gly-Lys-Pro-(D-Val)
Ac-(Ac-Lys-Lys)Lys-Ser-Ser-Ile-Ile-Ser-His-(D-Phe)-Arg-Trp-Gly-Lys-Pro-(D-Val)
Ac-(Ac-Lys-Lys)Lys-Ser-Ser-Ile-Ile-Ser-His-Phe-(D-Arg)-Trp-Gly-Lys-Pro-(D-Val)
Ac-(Ac-Lys-Lys)Lys-Ser-Ser-Ile-Ile-Ser-His-Phe-Arg-(D-Trp)-Gly-Lys-Pro-(D-Val)
Ac-(Ac-Lys-Lys)Lys-Ser-Ser-Ile-Ile-Ser-His-(D-Phe)-Arg-(D-Trp)-Gly-Lys-Pro-(D-Val)
Ac-(Ac-Lys-Lys)Lys-Ser-Ser-Ile-Ile-Ser-His-Nal-Arg-Trp-Gly-Lys-Pro-(D-Val)
Ac-(Ac-Lys-Lys)Lys-Ser-Ser-Ile-Ile-Ser-His-(D-Nal)-Arg-Trp-Gly-Lys-Pro-(D-Val)
The C-terminal Valine may be amidated (NH2).

X = Ac-(Ac-Lys-Lys-Lys)Lys-:
Ac-(Ac-Lys-Lys-Lys)Lys-Ser-Tyr-Ser-Met-Glu-His-Phe-Arg-Trp-Gly-Lys-Pro-Val (Ac-
(Ac-Lys-Lys-Lys)Lys-SEQ ID NO: 1)
Ac-(Ac-Lys-Lys-Lys)Lys-Ser-Tyr-Ser-Met-Glu-His-(D-Phe)-Arg-Trp-Gly-Lys-Pro-Val
Ac-(Ac-Lys-Lys-Lys)Lys-Ser-Tyr-Ser-Met-Glu-His-Phe-(D-Arg)-Trp-GlY-Lys-Pro-Val
Ac-(Ac-Lys-Lys-Lys)Lys-Ser-Tyr-Ser-Met-Glu-His-Phe-Arg-(D-Trp)-Gly-Lys-Pro-Val
Ac-(Ac-Lys-Lys-Lys)Lys-Ser-Tyr-Ser-Met-Glu-His-(D-Phe)-Arp-(D-Trp)-Gly-Lys-Pro-Val
Ac-(Ac-Lys-Lys-Lys)Lys-Ser-Tyr-Ser-Met-Glu-His-Nal-Arp-Trp-Gly-Lys-Pro-Val
Ac-(Ac-Lys-Lys-Lys)Lys-Ser-Tyr-Ser-Met-Glu-His-(D-Nal)-Arg-Trp-Gly-Lys-Pro-Val
Ac-(Ac-Lys-Lys-Lys)Lys-Ser-Tyr-Ser-Met-Glu-His-Phe-Arg-Trp-Gly-Lys-Pro-(D-Val)
Ac-(Ac-Lys-Lys-Lys)Lys-Ser-Tyr-Ser-Met-Glu-His-(D-Phe)-Arg-Trp-Gly-Lys-Pro-(D-Val)
Ac-(Ac-Lys-Lys-Lys)Lys-Ser-Tyr-Ser-Met-Glu-His-Phe-(D-Arg)-Trp-Gly-Lys-Pro-(D-Val)
Ac-(Ac-Lys-Lys-Lys)Lys-Ser-Tyr-Ser-Met-Glu-His-Phe-Arg-(D-Trp)-Gly-Lys-Pro-(D-Val)
Ac-(Ac-Lys-Lys-Lys)Lys-Ser-Tyr-Ser-Mot-Glu-His-(D-Phe)-Arg-(D-Trp)-Gly-Lys-Pro-(D-
Val)
Ac-(Ac-Lys-Lys-Lys)Lys-Ser-Tyr-Ser-Met-Glu-His-Nal-Arg-Trp-Gly-Lys-Pro-(D-Val)
Ac-(Ac-Lys-Lys-Lys)Lys-Ser-Tyr-Ser-Met-Glu-His-(D-Nal)-Arg-Trp-Gly-Lys-Pro-(D-Val)
Ac-(Ac-Lys-Lys-Lys)Lys-Ser-Tyr-Ser-Nle-Glu-His-Phe-Arg-Trp-Gly-Lys-Pro-Val (Ac-
(Ac-Lys-Lys-Lys)Lys-SEQ ID NO: 3)
Ac-(Ac-Lys-Lys-Lys)Lys-Ser-Tyr-Ser-Nle-Glu-His-(D-Phe)-Arg-Trp-Gly-Lys-Pro-Val
Ac-(Ac-Lys-Lys-Lys)Lys-Ser-Tyr-Ser-Nle-Glu-His-Phe-(D-Arg)-Trp-Gly-Lys-Pro-Val
Ac-(Ac-Lys-Lys-Lys)Lys-Ser-Tyr-Ser-Nle-Glu-His-Phe-Arg-(D-Trp)-Gly-Lys-Pro-Val
Ac-(Ac-Lys-Lys-Lys)Lys-Ser-Tyr-Ser-Nle-Glu-His-(D-Phe)-Arg-(D-Trp)-Gly-Lys-Pro-Val
Ac-(Ac-Lys-Lys-Lys)Lys-Ser-Tyr-Ser-Nle-Glu-His-Nal-Arg-Trp-Gly-Lys-Pro-Val
Ac-(Ac-Lys-Lys-Lys)Lys-Ser-Tyr-Ser-Nle-Glu-His-(D-Nal)-Arg-Trp-Gly-Lys-Pro-Val
Ac-(Ac-Lys-Lys-Lys)Lys-Ser-Tyr-Ser-Nle-Glu-His-Phe-Arg-Trp-Gly-Lys-Pro-(D-Val)
Ac-(Ac-Lys-Lys-Lys)Lys-Ser-Tyr-Ser-Nle-Glu-His-(D-Phe)-Arp-Trp-Gly-Lys-Pro-(D-Val)
Ac-(Ac-Lys-Lys-Lys)Lys-Ser-Tyr-Ser-Nle-Glu-His-Phe-(D-Arp)-Trp-Gly-Lys-Pro-(D-Val)
Ac-(Ac-Lys-Lys-Lys)Lys-Ser-Tyr-Ser-Nle-Glu-His-Phe-Arg-(D-Trp)-Gly-Lys-Pro-(D-Val)
Ac-(Ac-Lys-Lys-Lys)Lys-Ser-Tyr-Ser-Nle-Glu-His-(D-Phe)-Arg-(D-Trp)-Gly-Lys-Pro-(D-
Val)
Ac-(Ac-Lys-Lys-Lys)Lys-Ser-Tyr-Ser-Nle-Glu-His-Nal-Arg-Trp-Gly-Lys-Pro-(D-Val)
Ac-(Ac-Lys-Lys-Lys)Lys-Ser-Tyr-Ser-Nle-Glu-His-(D-Nal)-Arg-Trp-GIy-Lys-Pro-(D-Val)
Ac-(Ac-Lys-Lys-Lys)Lys-Ser-Ser-Ile-Ile-Ser-His-Phe-Arg-Trp-Gly-Lys-Pro-Val (Ac-(Ac-
Lys-Lys-Lys)Lys-SEQ ID NO: 5)
Ac-(Ac-Lys-Lys-Lys)Lys-Ser-Ser-Ile-Ile-Ser-His-(D-Phe)-Arg-Trp-Gly-Lys-Pro-Val
Ac-(Ac-Lys-Lys-Lys)Lys-Ser-Ser-Ile-Ile-Ser-His-Phe-(D-Arg)-Trp-Gly-Lys-Pro-Val
Ac-(Ac-Lys-Lys-Lys)Lys-Ser-Ser-Ile-Ile-Ser-His-Phe-Arg-(D-Trp)-Gly-Lys-Pro-Val
Ac-(Ac-Lys-Lys-Lys)Lys-Ser-Ser-Ile-Ile-Ser-His-(D-Phe)-Arg-(D-Trp)-Gly-Lys-Pro-Val
Ac-(Ac-Lys-Lys-Lys)Lys-Ser-Ser-Ile-Ile-Ser-His-Nal-Arg-Trp-Gly-Lys-Pro-Val
Ac-(Ac-Lys-Lys-Lys)Lys-Ser-Ser-Ile-Ile-Ser-His-(D-Nal)-Arg-Trp-Gly-Lys-Pro-Val
Ac-(Ac-Lys-Lys-Lys)Lys-Ser-Ser-Ile-Ile-Ser-His-Phe-Arg-Trp-Gly-Lys-Pro-(D-Val)
Ac-(Ac-Lys-Lys-Lys)Lys-Ser-Ser-Ile-Ile-Ser-His-(D-Phe)-Arg-Trp-Gly-Lys-Pro-(D-Val)
Ac-(Ac-Lys-Lys-Lys)Lys-Ser-Ser-Ile-Ile-Ser-His-Phe-(D-Arp)-Trp-Gly-Lys-Pro-(D-Val)
Ac-(Ac-Lys-Lys-Lys)Lys-Ser-Ser-Ile-Ile-Ser-His-Phe-Arg-(D-Trp)-Gly-Lys-Pro-(D-Val)
Ac-(Ac-Lys-Lys-Lys)Lys-Ser-Ser-Ile-Ile-Ser-His-(D-Phe)-Arg-(D-Trp)-Gly-Lys-Pro-(D-
Val)
Ac-(Ac-Lys-Lys-Lys)Lys-Ser-Ser-Ile-Ile-Ser-His-Nal-Arg-Trp-Gly-Lys-Pro-(D-Val)
Ac-(Ac-Lys-Lys-Lys)Lys-Ser-Ser-Ile-Ile-Ser-His-(D-Nal)-Arg-Trp-Gly-Lys-Pro-(D-Val)
The C-terminal Valine may be amidated (NH2).

X = Ac-(Ac-Lys-Gly-Lys)Lys-:
Ac-(Ac-Lys-Gly-Lys)Lys-Ser-Tyr-Ser-Met-Glu-His-Phe-Arg-Trp-Gly-Lys-Pro-Val (Ac-
(Ac-Lys-Gly-Lys)Lys-SEQ ID NO: 1)
Ac-(Ac-Lys-Gly-Lys)Lys-Ser-Tyr-Ser-Met-Glu-His-(D-Phe)-Arg-Trp-Gly-Lys-Pro-Val
Ac-(Ac-Lys-Gly-Lys)Lys-Ser-Tyr-Ser-Met-Glu-His-Phe-(D-Arg)-Trp-Gly-Lys-Pro-Val
Ac-(Ac-Lys-Gly-Lys)Lys-Ser-Tyr-Ser-Met-Glu-His-Phe-Arg-(D-Trp)-Gly-Lys-Pro-Val
Ac-(Ac-Lys-Gly-Lys)Lys-Ser-Tyr-Ser-Met-Glu-His-(D-Phe)-Arg-(D-Trp)-Gly-Lys-Pro-Val
Ac-(Ac-Lys-Gly-Lys)Lys-Ser-Tyr-Ser-Met-Glu-His-Nal-Arg-Trp-Gly-Lys-Pro-Val
Ac-(Ac-Lys-Gly-Lys)Lys-Ser-Tyr-Ser-Met-Glu-His-(D-Nal)-Arg-Trp-Gly-Lys-Pro-Val
```

APPENDIX-continued

Examples of sequences of MSH analogues

Ac-(Ac-Lys-Gly-Lys)Lys-Ser-Tyr-Ser-Met-Glu-His-Phe-Arg-Trp-Gly-Lys-Pro-(D-Val)
Ac-(Ac-Lys-Gly-Lys)Lys-Ser-Tyr-Ser-Met-Glu-His-(D-Phe)-Arg-Trp-Gly-Lys-Pro-(D-Val)
Ac-(Ac-Lys-Gly-Lys)Lys-Ser-Tyr-Ser-Met-Glu-His-Phe-(D-Arg)-Trp-Gly-Lys-Pro-(D-Val)
Ac-(Ac-Lys-Gly-Lys)Lys-Ser-Tyr-Ser-Met-Glu-His-Phe-Arg-(D-Trp)-Gly-Lys-Pro-(D-Val)
Ac-(Ac-Lys-Gly-Lys)Lys-Ser-Tyr-Ser-Met-Glu-His-(D-Phe)-Arg-(D-Trp)-Gly-Lys-Pro-(D-Val)
Ac-(Ac-Lys-Gly-Lys)Lys-Ser-Tyr-Ser-Met-Glu-His-Nal-Arg-Trp-Gly-Lys-Pro-(D-Val)
Ac-(Ac-Lys-Gly-Lys)Lys-Ser-Tyr-Ser-Met-Glu-His-(D-Nal)-Arg-Trp-Gly-Lys-Pro-(D-Val)
Ac-(Ac-Lys-Gly-Lys)Lys-Ser-Tyr-Ser-Nle-Glu-His-Phe-Arg-Trp-Gly-Lys-Pro-Val (Ac-(Ac-Lys-Gly-Lys)Lys-SEQ ID NO: 3)
Ac-(Ac-Lys-Gly-Lys)Lys-Ser-Tyr-Ser-Nle-Glu-His-(D-Phe)-Arg-Trp-Gly-Lys-Pro-Val
Ac-(Ac-Lys-Gly-Lys)Lys-Ser-Tyr-Ser-Nle-Glu-His-Phe-(D-Arg)-Trp-Gly-Lys-Pro-Val
Ac-(Ac-Lys-Gly-Lys)Lys-Ser-Tyr-Ser-Met-Glu-His-Phe-Arg-(D-Trp)-Gly-Lys-Pro-Val
Ac-(Ac-Lys-Gly-Lys)Lys-Ser-Tyr-Ser-Nle-Glu-His-(D-Phe)-Arg-(D-Trp)-Gly-Lys-Pro-Val
Ac-(Ac-Lys-Gly-Lys)Lys-Ser-Tyr-Ser-Nle-Glu-His-Nal-Arg-Trp-Gly-Lys-Pro-Val
Ac-(Ac-Lys-Gly-Lys)Lys-Ser-Tyr-Ser-Nle-Glu-His-(D-Nal)-Arg-Trp-Gly-Lys-Pro-Val
Ac-(Ac-Lys-Gly-Lys)Lys-Ser-Tyr-Ser-Nle-Glu-His-Phe-Arg-Trp-Gly-Lys-Pro-(D-Val)
Ac-(Ac-Lys-Gly-Lys)Lys-Ser-Tyr-Ser-Nle-Glu-His-(D-Phe)-Arg-Trp-Gly-Lys-Pro-(D-Val)
Ac-(Ac-Lys-Gly-Lys)Lys-Ser-Tyr-Ser-Nle-Glu-His-Phe-(D-Arg)-Trp-Gly-Lys-Pro-(D-Val)
Ac-(Ac-Lys-Gly-Lys)Lys-Ser-Tyr-Ser-Nle-Glu-His-Phe-Arg-(D-Trp)-Gly-Lys-Pro-(D-Val)
Ac-(Ac-Lys-Gly-Lys)Lys-Ser-Tyr-Ser-Nle-Glu-His-(D-Phe)-Arg-(D-Trp)-Gly-Lys-Pro-(D-Val)
Ac-(Ac-Lys-Gly-Lys)Lys-Ser-Tyr-Ser-Nle-Glu-His-Nal-Arg-Trp-Gly-Lys-Pro-(D-Val)
Ac-(Ac-Lys-Gly-Lys)Lys-Ser-Tyr-Ser-Nle-Glu-His-(D-Nal)-Arg-Trp-Gly-Lys-Pro-(D-Val)
Ac-(Ac-Lys-Gly-Lys)Lys-Ser-Ser-Ile-Ile-Ser-His-Phe-Arg-Trp-Gly-Lys-Pro-Val (Ac-(Ac-Lys-Gly-Lys)Lys-SEQ ID NO: 5)
Ac-(Ac-Lys-Gly-Lys)Lys-Ser-Ser-Ile-Ile-Ser-His-(D-Phe)-Arg-Trp-Gly-Lys-Pro-Val
Ac-(Ac-Lys-Gly-Lys)Lys-Ser-Ser-Ile-Ile-Ser-His-Phe-(D-Arg)-Trp-Gly-Lys-Pro-Val
Ac-(Ac-Lys-Gly-Lys)Lys-Ser-Ser-Ile-Ile-Ser-His-Phe-Arg-(D-Trp)-Gly-Lys-Pro-Val
Ac-(Ac-Lys-Gly-Lys)Lys-Ser-Ser-Ile-Ile-Ser-His-(D-Phe)-Arg-(D-Trp)-Gly-Lys-Pro-Val
Ac-(Ac-Lys-Gly-Lys)Lys-Ser-Ser-Ile-Ile-Ser-His-Nal-Arg-Trp-Gly-Lys-Pro-Val
Ac-(Ac-Lys-Gly-Lys)Lys-Ser-Ser-Ile-Ile-Ser-His-(D-Nal)-Arg-Trp-Gly-Lys-Pro-Val
Ac-(Ac-Lys-Gly-Lys)Lys-Ser-Ser-Ile-Ile-Ser-His-Phe-Arg-Trp-Gly-Lys-Pro-(D-Val)
Ac-(Ac-Lys-Gly-Lys)Lys-Ser-Ser-Ile-Ile-Ser-His-(D-Phe)-Arg-Trp-Gly-Lys-Pro-(D-Val)
Ac-(Ac-Lys-Gly-Lys)Lys-Ser-Ser-Ile-Ile-Ser-His-Phe-(D-Arg)-Trp-Gly-Lys-Pro-(D-Val)
Ac-(Ac-Lys-Gly-Lys)Lys-Ser-Ser-Ile-Ile-Ser-His-Phe-Arg-(D-Trp)-Gly-Lys-Pro-(D-Val)
Ac-(Ac-Lys-Gly-Lys)Lys-Ser-Ser-IIe-Ile-Ser-His-(D-Phe)-Arg-(D-Trp)-Gly-Lys-Pro-(D-Val)
Ac-(Ac-Lys-Gly-Lys)Lys-Ser-Ser-Ile-Ile-Ser-His-Nal-Arg-Trp-Gly-Lys-Pro-(D-Val)
Ac-(Ac-Lys-Gly-Lys)Lys-Ser-Ser-Ile-Ile-Ser-His-(D-Nal)-Arg-Trp-Gly-Lys-Pro-(D-Val)
The C-terminal Valine may be amidate (NH$_2$).

X = Ac-(Ac-Lys)Lys-Lys-:
Ac-(Ac-Lys-Lys-Gly)Lys-Ser-Tyr-Ser-Met-Glu-His-Phe-Arg-Trp-Gly-Lys-Pro-Val (Ac-(Ac-Lys-Lys-Gly)Lys-SEQ ID NO: 1)
Ac-(Ac-Lys-Lys-Gly)Lys-Ser-Tyr-Ser-Met-Glu-His-(D-Phe)-Arg-Trp-Gly-Lys-Pro-Val
Ac-(Ac-Lys-Lys-Gly)Lys-Ser-Tyr-Ser-Met-Glu-His-Phe-(D-Arg)-Trp-Gly-Lys-Pro-Val
Ac-(Ac-Lys-Lys-Gly)Lys-Ser-Tyr-Ser-Met-Glu-His-Phe-Arg-(D-Trp)-Gly-Lys-Pro-Val
Ac-(Ac-Lys-Lys-Gly)Lys-Ser-Tyr-Ser-Met-Glu-His-(D-Phe)-Arg-(D-Trp)-Gly-Lys-Pro-Val
Ac-(Ac-Lys-Lys-Gly)Lys-Ser-Tyr-Ser-Met-Glu-His-Nal-Arg-Trp-Gly-Lys-Pro-Val
Ac-(Ac-Lys-Lys-Gly)Lys-Ser-Tyr-Ser-Met-Glu-His-(D-Nal)-Arg-Trp-Gly-Lys-Pro-Val
Ac-(Ac-Lys-Lys-Gly)Lys-Ser-Tyr-Ser-Met-Glu-His-Phe-Arg-Trp-Gly-Lys-Pro-(D-Val)
Ac-(Ac-Lys-Lys-Gly)Lys-Ser-Tyr-Ser-Met-Glu-His-(D-Phe)-Arg-Trp-Gly-Lys-Pro-(D-Val)
Ac-(Ac-Lys-Lys-Gly)Lys-Ser-Tyr-Ser-Met-Glu-His-Phe-(D-Arg)-Trp-Gly-Lys-Pro-(D-Val)
Ac-(Ac-Lys-Lys-Gly)Lys-Ser-Tyr-Ser-Met-Glu-His-Phe-Arg-(D-Trp)-Gly-Lys-Pro-(D-Val)
Ac-(Ac-Lys-Lys-Gly)Lys-Ser-Tyr-Ser-Met-Glu-His-(D-Phe)-Arg-(D-Trp)-Gly-Lys-Pro-(D-Val)
Ac-(Ac-Lys-Lys-Gly)Lys-Ser-Tyr-Ser-Met-Glu-His-Nal-Arg-Trp-Gly-Lys-Pro-(D-Val)
Ac-(Ac-Lys-Lys-Gly)Lys-Ser-Tyr-Ser-Met-Glu-His-(D-Nal)-Arg-Trp-Gly-Lys-Pro-(D-Val)
Ac-(Ac-Lys-Lys-Gly)Lys-Ser-Tyr-Ser-Nle-Glu-His-Phe-Arg-Trp-Gly-Lys-Pro-Val (Ac-(Ac-Lys-Lys-Gly)Lys-SEQ ID NO: 3)
Ac-(Ac-Lys-Lys-Gly)Lys-Ser-Tyr-Ser-Nle-Glu-His-(D-Phe)-Arg-Trp-Gly-Lys-Pro-Val
Ac-(Ac-Lys-Lys-Gly)Lys-Ser-Tyr-Ser-Nle-Glu-His-Phe-(D-Arg)-Trp-Gly-Lys-Pro-Val
Ac-(Ac-Lys-Lys-Gly)Lys-Ser-Tyr-Ser-Nle-Glu-His-Phe-Arg-(D-Trp)-Gly-Lys-Pro-Val
Ac-(Ac-Lys-Lys-Gly)Lys-Ser-Tyr-Ser-Nle-Glu-His-(D-Phe)-Arg-(D-Trp)-Gly-Lys-Pro-Val
Ac-(Ac-Lys-Lys-Gly)Lys-Ser-Tyr-Ser-Nle-Glu-His-Nal-Arg-Trp-Gly-Lys-Pro-Val
Ac-(Ac-Lys-Lys-Gly)Lys-Ser-Tyr-Ser-Nle-Glu-His-(D-Nal)-Arg-Trp-Gly-Lys-Pro-Val
Ac-(Ac-Lys-Lys-Gly)Lys-Ser-Tyr-Ser-Nle-Glu-His-Phe-Arg-Trp-Gly-Lys-Pro-(D-Val)
Ac-(Ac-Lys-Lys-Gly)Lys-Ser-Tyr-Ser-Nle-Glu-His-(D-Phe)-Arg-Trp-Gly-Lys-Pro-(D-Val)
Ac-(Ac-Lys-Lys-Gly)Lys-Ser-Tyr-Ser-Nle-Glu-His-Phe-(D-Arg)-Trp-Gly-Lys-Pro-(D-Val)
Ac-(Ac-Lys-Lys-Gly)Lys-Ser-Tyr-Ser-Nle-Glu-His-Phe-Arg-(D-Trp)-Gly-Lys-Pro-(D-Val)
Ac-(Ac-Lys-Lys-Gly)Lys-Ser-Tyr-Ser-Nle-Glu-His-(D-Phe)-Arg-(D-Trp)-Gly-Lys-Pro-(D-Val)
Ac-(Ac-Lys-Lys-Gly)Lys-Ser-Tyr-Ser-Nle-Glu-His-Nal-Arg-Trp-Gly-Lys-Pro-(D-Val)
Ac-(Ac-Lys-Lys-Gly)Lys-Ser-Tyr-Ser-Nle-Glu-His-(D-Nal)-Arg-Trp-Gly-Lys-Pro-(D-Val)
Ac-(Ac-Lys-Lys-Gly)Lys-Ser-Ser-Ile-Ile-Ser-His-Phe-Arg-Trp-Gly-Lys-Pro-Val (Ac-(Ac-Lys-Lys-Gly)Lys-SEQ ID NO: 5)
Ac-(Ac-Lys-Lys-Gly)Lys-Ser-Ser-Ile-Ile-Ser-His-(D-Phe)-Arg-Trp-Gly-Lys-Pro-Val

APPENDIX-continued

Examples of sequences of MSH analogues

Ac-(Ac-Lys-Lys-Gly)Lys-Ser-Ser-Ile-Ile-Ser-His-Phe-(D-Arg)-Trp-Gly-Lys-Pro-Val
Ac-(Ac-Lys-Lys-Gly)Lys-Ser-Ser-Ile-Ile-Ser-His-Phe-Arg-(D-Trp)-Gly-Lys-Pro-Val
Ac-(Ac-Lys-Lys-Gly)Lys-Ser-Ser-Ile-Ile-Ser-His-(D-Phe)-Arg-(D-Trp)-Gly-Lys-Pro-Val
Ac-(Ac-Lys-Lys-Gly)Lys-Ser-Ser-Ile-Ile-Ser-His-Nal-Arg-Trp-Gly-Lys-Pro-Val
Ac-(Ac-Lys-Lys-Gly)Lys-Ser-Ser-Ile-Ile-Ser-His-(D-Nal)-Arg-Trp-Gly-Lys-Pro-Val
Ac-(Ac-Lys-Lys-Gly)Lys-Ser-Ser-Ile-Ile-Ser-His-Phe-Arg-Trp-Gly-Lys-Pro-(D-Val)
Ac-(Ac-Lys-Lys-Gly)Lys-Ser-Ser-Ile-Ile-Ser-His-(D-Phe)-Arp-Tro-Gly-Lys-Pro-(D-Val)
Ac-(Ac-Lys-Lys-Gly)Lys-Ser-Ser-Ile-Ile-Ser-His-Phe-(D-Arg)-Trp-Gly-Lys-Pro-(D-Val)
Ac-(Ac-Lys-Lys-Gly)Lys-Ser-Ser-Ile-Ile-Ser-His-Phe-Arg-(D-Trp)-Gly-Lys-Pro-(D-Val)
Ac-(Ac-Lys-Lys-Gly)Lys-Ser-Ser-Ile-Ile-Ser-Hls-(D-Phe)-Arg-(D-Trp)-Gly-Lys-Pro-(D-Val)
Ac-(Ac-Lys-Lys-Gly)Lys-Ser-Ser-Ile-Ile-Ser-His-Nal-Arg-Trp-Gly-Lys-Pro-(D-Val)
Ac-(Ac-Lys-Lys-Gly)Lys-Ser-Ser-Ile-Ile-Ser-His-(D-Nal)-Arg-Trp-Gly-Lys-Pro-(D-Val)
The C-terminal Valine may be amidated (NH$_2$).

X = Ac-(Ac-Lys)Lys-Lys-:
Ac-(Ac-Lys)Lys-Lys-Ser-Tyr-Ser-Met-Glu-His-Phe-Arg-Trp-Gly-Lys-Pro-Val (Ac-(Ac-Lys)Lys-Lys-SEQ ID NO: 1)
Ac-(Ac-Lys)Lys-Lys-Ser-Tyr-Ser-Met-Glu-His-(D-Phe)-Arg-Trp-Gly-Lys-Pro-Val
Ac-(Ac-Lys)Lys-Lys-Ser-Tyr-Ser-Met-Glu-His-Phe-(D-Arg)-Trp-Gly-Lys-Pro-Val
Ac-(Ac-Lys)Lys-Lys-Ser-Tyr-Ser-Met-Glu-His-Phe-Arg-(D-Trp)-Gly-Lys-Pro-Val
Ac-(Ac-Lys)Lys-Lys-Ser-Tyr-Ser-Met-Glu-His-(D-Phe)-Arg-(D-Trp)-Gly-Lys-Pro-Val
Ac-(Ac-Lys)Lys-Lys-Ser-Tyr-Ser-Met-Glu-His-Nal-Arg-Trp-Gly-Lys-Pro-Val
Ac-(Ac-Lys)Lys-Lys-Ser-Tyr-Ser-Met-Glu-His-(D-Nal)-Arg-Trp-Gly-Lys-Pro-Val
Ac-(Ac-Lys)Lys-Lys-Ser-Tyr-Ser-Met-Glu-His-Phe-Arg-Trp-Gly-Lys-Pro-(D-Val)
Ac-(Ac-Lys)Lys-Lys-Ser-Tyr-Ser-Met-Glu-His-(D-Phe)-Arg-Trp-Gly-Lys-Pro-(D-Val)
Ac-(Ac-Lys)Lys-Lys-Ser-Tyr-Ser-Met-Glu-His-Phe-(D-Arg)-Trp-Gly-Lys-Pro-(D-Val)
Ac-(Ac-Lys)Lys-Lys-Ser-Tyr-Ser-Met-Glu-His-Phe-Arg-(D-Trp)-Gly-Lys-Pro-(D-Val)
Ac-(Ac-Lys)Lys-Lys-Ser-Tyr-Ser-Met-Glu-His-(D-Phe)-Arg-(D-Trp)-Gly-Lys-Pro-(D-Val)
Ac-(Ac-Lys)Lys-Lys-Ser-Tyr-Ser-Met-Glu-His-Nal-Arg-Trp-Gly-Lys-Pro-(D-Val)
Ac-(Ac-Lys)Lys-Lys-Ser-Tyr-Ser-Met-Glu-His-(D-Nal)-Arg-Trp-Gly-Lys-Pro-(D-Val)
Ac-(Ac-Lys)Lys-Lys-Ser-Tyr-Ser-Met-Glu-His-Phe-Arg-Trp-Gly-Lys-Pre-Val (Ac-(Ac-Lys)Lys-Lys-SEQ ID NO: 3)
Ac-(Ac-Lys)Lys-Lys-Ser-Tyr-Ser-Nle-Glu-His-(D-Phe)-Arg-Trp-Gly-Lys-Pro-Val
Ac-(Ac-Lys)Lys-Lys-Ser-Tyr-Ser-Nle-Glu-His-Phe-(D-Arg)-Trp-Gly-Lys-Pro-Val
Ac-(Ac-Lys)Lys-Lys-Ser-Tyr-Ser-Nle-Glu-His-Phe-Arg-(D-Trp)-Gly-Lys-Pro-Val
Ac-(Ac-Lys)Lys-Lys-Ser-Tyr-Ser-Nle-Glu-His-(D-Phe)-Arg-(D-Trp)-Gly-Lys-Pro-Val
Ac-(Ac-Lys)Lys-Lys-Ser-Tyr-Ser-Nle-Glu-His-Nal-Arg-Trp-Gly-Lys-Pro-Val
Ac-(Ac-Lys)Lys-Lys-Ser-Tyr-Ser-Nle-Glu-His-(D-Nal)-Arg-Trp-Gly-Lys-Pro-Val
Ac-(Ac-Lys)Lys-Lys-Ser-Tyr-Ser-Nle-Glu-His-Phe-Arg-Trp-Gly-Lys-Pro-(D-Val)
Ac-(Ac-Lys)Lys-Lys-Ser-Tyr-Ser-Nle-Glu-His-(D-Phe)-Arg-Trp-Gly-Lys-Pro-(D-Val)
Ac-(Ac-Lys)Lys-Lys-Ser-Tyr-Ser-Nle-Glu-His-Phe-(D-Arg)-Trp-Gly-Lys-Pro-(D-Val)
Ac-(Ac-Lys)Lys-Lys-Ser-Tyr-Ser-Nle-Glu-His-Phe-Arg-(D-Trp)-Gly-Lys-Pro-(D-Val)
Ac-(Ac-Lys)Lys-Lys-Ser-Tyr-Ser-Nle-Glu-His-(D-Phe)-Arg-(D-Trp)-Gly-Lys-Pro-(D-Val)
Ac-(Ac-Lys)Lys-Lys-Ser-Tyr-Ser-Nle-Glu-His-Nal-Arg-Trp-Gly-Lys-Pro-(D-Val)
Ac-(Ac-Lys)Lys-Lys-Ser-Tyr-Ser-Nle-Glu-His-(D-Nal)-Arg-Trp-Gly-Lys-Pro-(D-Val)
Ac-(Ac-Lys)Lys-Lys-Ser-Ser-Ile-Ile-Ser-His-Phe-Arg-Trp-Gly-Lys-Pro-Val (Ac-(Ac-Lys)Lys-Lys-SEQ ID NO: 5)
Ac-(Ac-Lys)Lys-Lys-Ser-Ser-Ile-Ile-Ser-His-(D-Phe)-Arg-Trp-Gly-Lys-Pro-Nal
Ac-(Ac-Lys)Lys-Lys-Ser-Ser-Ile-Ile-Ser-His-Phe-(D-Arg)-Trp-Gly-Lys-Pro-Val
Ac-(Ac-Lys)Lys-Lys-Ser-Ser-Ile-Ile-Ser-His-Phe-Arg-(D-Trp)-Gly-Lys-Pro-Val
Ac-(Ac-Lys)Lys-Lys-Ser-Ser-Ile-Ile-Ser-His-(D-Phe)-Arg-(D-Trp)-Gly-Lys-Pro-Val
Ac-(Ac-Lys)Lys-Lys-Ser-Ser-Ile-Ile-Ser-His-Nal-Arg-Trp-Gly-Lys-Pro-Val
Ac-(Ac-Lys)Lys-Lys-Ser-Ser-Ile-Ile-Ser-His-(D-Nal)-Arg-Trp-Gly-Lys-Pro-Val
Ac-(Ac-Lys)Lys-Lys-Ser-Ser-Ile-Ile-Ser-His-Phe-Arg-Trp-Gly-Lys-Pro-(D-Val)
Ac-(Ac-Lys)Lys-Lys-Ser-Ser-Ile-Ile-Ser-His-(D-Phe)-Arg-Trp-Gly-Lys-Pro-(D-Val)
Ac-(Ac-Lys)Lys-Lys-Ser-Ser-Ile-Ile-Ser-His-Phe-(D-Arg)-Trp-Gly-Lys-Pro-(D-Val)
Ac-(Ac-Lys)Lys-Lys-Ser-Ser-Ile-Ile-Ser-His-Phe-Arg-(D-Trp)-Gly-Lys-Pro-(D-Val)
Ac-(Ac-Lys)Lys-Lys-Ser-Ser-Ile-Ile-Ser-His-(D-Phe)-Arg-(D-Trp)-Gly-Lys-Pro-(D-Val)
Ac-(Ac-Lys)Lys-Lys-Ser-Ser-Ile-Ile-Ser-His-Nal-Arg-Trp-Gly-Lys-Pro-(D-Val)
Ac-(Ac-Lys)Lys-Lys-Ser-Ser-Ile-Ile-Ser-Hls-(D-Nal)-Arg-Trp-Gly-Lys-Pro-(D-Val)
The C-terminal Valine may be amidated (NH$_2$).

X = Ac-(Ac-Lys-Lys)Lys-Lys-:
Ac-Lys-(Ac-Lys-Lys)Lys-Lys-Ser-Tyr-Ser-Met-Glu-His-Phe-Arg-Trp-Gly-Lys-Pro-Val (Ac-(Ac-Lys-Lys)Lys-Lys-SEQ ID NO: 1)
Ac-(Ac-Lys-Lys)Lys-Lys-Ser-Tyr-Ser-Met-Glu-His-Phe-(D-Arg)-Trp-Gly-Lys-Pro-Val
Ac-(Ac-Lys-Lys)Lys-Lys-Ser-Tyr-Ser,Met-Glu-His-Phe-Arg-(D-Trp)-Gly-Lys-Pro,Val
Ac-(Ac-Lys-Lys)Lys-Lys-Ser-Tyr-Ser-Met-Glu-His-(D-Phe)-Arg-(D-Trp)-Gly-Lys-Pro-Val
Ac-(Ac-Lys-Lys)Lys-Lys-Ser-Tyr-Ser-Met-Glu-His-Nal-Arg-Trp-Gly-Lys-Pro-Val
Ac-(Ac-Lys-Lys)Lys-Lys-Ser-Tyr-Ser-Met-Glu-His-(D-Nal)-Arg-Trp-Gly-Lys-Pro-Val
Ac-(Ac-Lys-Lys)Lys-Lys-Ser-Tyr-Ser-Met-Glu-His-Phe-Arg-Trp-Gly-Lys-Pro-(D-Val)
Ac-(Ac-Lys-Lys)Lys-Lys-Ser-Tyr-Ser-Met-Glu-His-(D-Phe)-Arg-Trp-Gly-Lys-Pro-(D-Val)
Ac-(Ac-Lys-Lys)Lys-Lys-Ser-Tyr-Ser-Met-Glu-His-Phe-(D-Arg)-Trp-Gly-Lys-Pro-(D-Val)
Ac-(Ac-Lys-Lys)Lys-Lys-Ser-Tyr-Ser-Met-Glu-His-Phe-Arg-(D-Trp)-Gly-Lys-Pro-(D-Val)
Ac-(Ac-Lys-Lys)Lys-Lys-Ser-Tyr-Ser-Met-Glu-His-(D-Phe)-Arg-(D-Trp)-Gly-Lys-Pro-(D-Val)
Ac-(Ac-Lys-Lys)Lys-Lys-Ser-Tyr-Ser-Met-Glu-His-Nal-Arg-Trp-Gly-Lys-Pro-(D-Val)

APPENDIX-continued

Examples of sequences of MSH analogues

Ac-(Ac-Lys-Lys)Lys-Lys-Ser-Tyr-Ser-Met-Glu-His-(D-Nal)-Arg-Trp-Gly-Lys-Pro-(D-Val)
Ac-(Ac-Lys-Lys)Lys-Lys-Ser-Tyr-Ser-Nle-Glu-His-Phe-Arg-Trp-Gly-Lys-Pro-Val (Ac-(Ac-Lys-Lys)Lys-Lys-SEQ ID NO: 3)
Ac-(Ac-Lys-Lys)Lys-Lys-Ser-Tyr-Ser-Nle-Glu-His-(D-Phe)-Arg-Trp-Gly-Lys-Pro-Val
Ac-(Ac-Lys-Lys)Lys-Lys-Ser-Tyr-Ser-Nle-Glu-His-Phe-(D-Arg)-Trp-Gly-Lys-Pro-Val
Ac-(Ac-Lys-Lys)Lys-Lys-Ser-Tyr-Ser-Nle-Glu-His-Phe-Arg-(D-Trp)-Gly-Lys-Pro-Val
Ac-(Ac-Lys-Lys)Lys-Lys-Ser-Tyr-Ser-Nle-Glu-His-(D-Phe)-Arg-(D-Trp)-Gly-Lys-Pro-Val
Ac-(Ac-Lys-Lys)Lys-Lys-Ser-Tyr-Ser-Nle-Glu-His-Nal-Arg-Trp-Gly-Lys-Pro-Val
Ac-(Ac-Lys-Lys)Lys-Lys-Ser-Tyr-Ser-Nle-Glu-His-(D-Nal)-Arg-Trp-Gly-Lys-Pro-Val
Ac-(Ac-Lys-Lys)Lys-Lys-Ser-Tyr-Ser-Nle-Glu-His-Phe-Arg-Trp-Gly-Lys-Pro-(D-Val)
Ac-(Ac-Lys-Lys)Lys-Lys-Ser-Tyr-Ser-Nle-Glu-His-(D-Phe)-Arg-Trp-Gly-Lys-Pro-(D-Val)
Ac-(Ac-Lys-Lys)Lys-Lys-Ser-Tyr-Ser-Nle-Glu-His-Phe-(D-Arg)-Trp-Gly-Lys-Pro-(D-Val)
Ac-(Ac-Lys-Lys)Lys-Lys-Ser-Tyr-Ser-Nle-Glu-His-Phe-Arg-(D-Trp)-Gly-Lys-Pro-(D-Val)
Ac-(Ac-Lys-Lys)Lys-Lys-Ser-Tyr-Ser-Nle-Glu-His-(D-Phe)-Arg-(D-Trp)-Gly-Lys-Pro-(D-Val)
Ac-(Ac-Lys-Lys)Lys-Lys-Ser-Tyr-Ser-Nle-Glu-His-Nal-Arg-Trp-Gly-Lys-Pro-(D-Val)
Ac-(Ac-Lys-Lys)Lys-Lys-Ser-Tyr-Ser-Nle-Glu-His-(D-Nal)-Arg-Trp-Gly-Lys-Pro-(D-Val)
Ac-(Ac-Lys-Lys)Lys-Lys-Ser-Ser-Ile-Ile-Ser-His-Phe-Arg-Trp-Gly-Lys-Pro-Val (Ac-(Ac-Lys-Lys)Lys-Lys-SEQ ID NO: 5)
Ac-(Ac-Lys-Lys)Lys-Lys-Ser-Ser-Ile-Ile-Ser-His-(D-Phe)-Arg-Trp-Gly-Lys-Pro-Val
Ac-(Ac-Lys-Lys)Lys-Lys-Ser-Ser-Ile-Ile-Ser-His-Phe-(D-Arg)-Trp-Gly-Lys-Pro-Val
Ac-(Ac-Lys-Lys)Lys-Lys-Ser-Ser-Ile-Ile-Ser-His-Phe-Arg-(D-Trp)-Gly-Lys-Pro-Val
Ac-(Ae-Lys-Lys)Lys-Lys-Ser-Ser-Ile-Ile-Ser-His-(D-Phe)-Arg-(D-Trp)-Gly-Lys-Pro-Val
Ac-(Ac-Lys-Lys)Lys-Lys-Ser-Ser-Ile-Ile-Ser-His-Nal-Arg-Trp-Gly-Lys-Pro-Val
Ac-(Ac-Lys-Lys)Lys-Lys-Ser-Ser-Ile-Ile-Ser-His-(D-Nal)-Arg-Trp-Gly-Lys-Pro-Val
Ac-(Ac-Lys-Lys)Lys-Lys-Ser-Ser-Ile-Ile-Ser-His-Phe-Arg-Trp-Gly-Lys-Pro-(D-Val)
Ac-(Ac-Lys-Lys)Lys-Lys-Ser-Ser-Ile-Ile-Ser-His-(D-Phe)-Arg-Trp-Gly-Lys-Pro-(D-Val)
Ac-(Ac-Lys-Lys)Lys-Lys-Ser-Ser-Ile-Ile-Ser-His-Phe-(D-Arg)-Trp-Gly-Lys-Pro-(D-Val)
Ac-(Ac-Lys-Lys)Lys-Lys-Ser-Ser-Ile-Ile-Ser-His-Phe-Arg-(D-Trp)-Gly-Lys-Pro-(D-Val)
Ac-(Ac-Lys-Lys)Lys-Lys-Ser-Ser-Ile-Ile-Ser-His-(D-Phe)-Arg-(D-Trp)-Gly-Lys-Pro-(D-Val)
Ac-(Ac-Lys-Lys)Lys-Lys-Ser-Ser-Ile-Ile-Ser-His-Nal-Arg-Trp-Gly-Lys-Pro-(D-Val)
Ac-(Ac-Lys-Lys)Lys-Lys-Ser-Ile-Ile-Ser-His-(D-Nal)-Arg-Trp-Gly-Lys-Pro-(D-Val)
The C-terminal Valine may be amidated (NH₂).

X = Ac-Lys-(Ac-Lys)Lys-:
Ac-Lys-(Ac-Lys)Lys-Ser-Tyr-Ser-Met-Glu-His-Phe-Arg-Trp-Gly-Lys-Pro-Val (Ac-Lys-(Ac-Lys)Lys-SEQ ID NO: 1)
Ac-Lys-(Ac-Lys)Lys-Ser-Tyr-Ser-Met-Glu-His-(D-Phe)-Arg-Trp-Gly-Lys-Pro-Val
Ac-Lys-(Ac-Lys)Lys-Ser-Tyr-Ser-Met-Glu-His-Phe-(D-Arg)-Trp-Gly-Lys-Pro-Val
Ac-Lys-(Ac-Lys)Lys-Ser-Tyr-Ser-Met-Glu-His-Phe-Arg-(D-Trp)-Gly-Lys-Pro-Val
Ac-Lys-(Ac-Lys)Lys-Ser-Tyr-Ser-Met-Glu-His-(D-Phe)-Arg-(D-Trp)-Gly-Lys-Pro-Val
Ac-Lys-(Ac-Lys)Lys-Ser-Tyr-Ser-Met-Glu-His-Nal-Arg-Trp-Gly-Lys-Pre-Val
Ac-Lys-(Ac-Lys)Lys-Ser-Tyr-Ser-Met-Glu-His-(D-Nal)-Arg-Trp-Gly-Lys-Pro-Val
Ac-Lys-(Ac-Lys)Lys-Ser-Tyr-Ser-Met-Glu-His-Phe-Arg-Trp-Gly-Lys-Pro-(D-Val)
Ac-Lys-(Ac-Lys)Lys-Ser-Tyr-Ser-Met-Glu-His-(D-Phe)-Arg-Trp-Gly-Lys-Pro-(D-Val)
Ac-Lys-(Ac-Lys)Lys-Ser-Tyr-Ser-Met-Glu-His-Phe-(D-Arg)-Trp-Gly-Lys-Pro-(D-Val)
Ac-Lys-(Ac-Lys)Lys-Ser-Tyr-Ser-Met-Glu-His-Phe-Arg-(D-Trp)-Gly-Lys-Pro-(D-Val)
Ac-Lys-(Ac-Lys)Lys-Ser-Tyr-Ser-Nle-Glu-His-(D-Phe)-Arg-(D-Trp)-Gly-Lys-Pro-(D-Val)
Ac-Lys-(Ac-Lys)Lys-Ser-Tyr-Ser-Met-Glu-His-Nal-Arg-Trp-Gly-Lys-Pro-(D-Val)
Ac-Lys-(Ac-Lys)Lys-Ser-Tyr-Ser-Met-Glu-His-(D-Nal)-Arg-Trp-Gly-Lys-Pro-(D-Val)
Ac-Lys-(Ac-Lys)Lys-Ser-Tyr-Ser-Nle-Glu-His-Phe-Arg-Trp-Gly-Lys-Pro-Val (Ac-Lys-(Ac-Lys)Lys-SEQ ID NO: 3)
Ac-Lys-(Ac-Lys)Lys-Ser-Tyr-Ser-Nle-Glu-His-(D-Phe)-Arg-Trp-Gly-Lys-Pro-Val
Ac-Lys-(Ac-Lys)Lys-Ser-Tyr-Ser-Nle-Glu-His-Phe-(D-Arg)-Trp-Gly-Lys-Pro-Val
Ac-Lys-(Ac-Lys)Lys-Ser-Tyr-Ser-Nle-Glu-His-Phe-Arg-(D-Trp)-Gly-Lys-Pro-Val
Ac-Lys-(Ac-Lys)Lys-Ser-Tyr-Ser-Nle-Glu-His-(D-Phe)-Arg-(D-Trp)-Gly-Lys-Pro-Val
Ac-Lys-(Ac-Lys)Lys-Ser-Tyr-Ser-Nle-Glu-His-Nal-Arg-Trp-Gly-Lys-Pro-Val
Ac-Lys-(Ac-Lys)Lys-Ser-Tyr-Ser-Nle-Glu-His-(D-Nal)-Arg-Trp-Gly-Lys-Pro-Val
Ac-Lys-(Ac-Lys)Lys-Ser-Tyr-Ser-Nle-Glu-His-Phe-Arg-Trp-Gly-Lys-Pro-(D-Val)
Ac-Lys-(Ac-Lys)Lys-Ser-Tyr-Ser-Nle-Glu-His-(D-Phe)-Arg-Trp-Gly-Lys-Pro-(D-Val)
Ac-Lys-(Ac-Lys)Lys-Ser-Tyr-Ser-Nle-Glu-His-Phe-(D-Arg)-Trp-Gly-Lys-Pro-(D-Val)
Ac-Lys-(Ac-Lys)Lys-Ser-Tyr-Ser-Nle-Glu-His-Phe-Arg-(D-Trp)-Gly-Lys-Pro-(D-Val)
Ac-Lys-(Ac-Lys)Lys-Ser-Tyr-Ser-Nle-Glu-His-(D-Phe)-Arg-(D-Trp)-Gly-Lys-Pro-(D-Val)
Ac-Lys-(Ac-Lys)Lys-Ser-Tyr-Ser-Nle-Glu-His-Nal-Arg-Trp-Gly-Lys-Pre-p-Val)
Ac-Lys-(Ac-Lys)Lys-Ser-Tyr-Ser-Nle-Glu-His-(D-Nal)-Arg-Trp-Gly-Lys-Pro-(D-Val)
Ac-Lys-(Ac-Lys)Lys-Ser-Ser-Ile-Ile-Ser-His-Phe-Arg-Trp-Gly-Lys-Pro-Val (Ac-Lys-(Ac-Lys)Lys-SEQ ID NO: 5)
Ac-Lys-(Ac-Lys)Lys-Ser-Ser-Ile-Ile-Ser-His-(D-Phe)-Arg-Trp-Gly-Lys-Pro-Val
Ac-Lys-(Ae-Lys)Lys-Ser-Ser-Ile-Ile-Ser-His-Phe-(D-Arg)-Trp-Gly-Lys-Pro-Val
Ac-Lys-(Ac-Lys)Lys-Ser-Ser-Ile-Ile-Ser-His-Phe-Arg-(D-Trp)-Gly-Lys-Pro-Val
Ac-Lys-(Ac-Lys)Lys-Ser-Ser-Ile-Ile-Ser-His-(D-Phe)-Arg-(D-Trp)-Gly-Lys-Pro-Val
Ac-Lys-(Ac-Lys)Lys-Ser-Ser-Ile-Ile-Ser-His-Nal-Arg-Trp-Gly-Lys-Pro-Val
Ac-Lys-(Ac-Lys)Lys-Ser-Ser-Ile-Ile-Ser-His-(D-Nal)-Arg-Trp-Gly-Lys-Pro-Val
Ac-Lys-(Ac-Lys)Lys-Ser-Ser-Ile-Ile-Ser-His-Phe-Arg-Trp-Gly-Lys-Pro-(D-Val)
Ac-Lys-(Ac-Lys)Lys-Ser-Ser-Ile-Ile-Ser-His-(D-Phe)-Arg-Trp-Gly-Lys-Pro-(D-Val)
Ac-Lys-(Ac-Lys)Lys-Ser-Ser-Ile-Ile-Ser-His-Phe-(D-Arg)-Trp-Gly-Lys-Pro-(D-Val)
Ac-Lys-(Ac-Lys)Lys-Ser-Ser-Ile-Ile-Ser-His-Phe-Arg-(D-Trp)-Gly-Lys-Pro-(D-Val)

APPENDIX-continued

Examples of sequences of MSH analogues

Ac-Lys-(Ac-Lys)Lys-Ser-Ser-Ile-Ile-Ser-His-(D-Phe)-Arg-(D-Trp)-Gy-Lys-Pro-(D-Val)
Ac-Lys-(Ac-Lys)Lys-Ser-Ser-Ile-Ile-Ser-His-Nal-Arg-Trp-Gly-Lys-Pro-(D-Val)
Ac-Lys-(Ac-Lys)Lys-Ser-Ser-Ile-Ile-Ser-His-(D-Nal)-Arg-Trp-Gly-Lys-Pro-(D-Val)
The C-terminal Valine may be amidated (NH$_2$).

X = Ac-Lys-(Ac-Lys-Lys)Lys-:
Ac-Lys-(Ac-Lys-Lys)Lys-Ser-Tyr-Ser-Met-Glu-His-Phe-Arg-Trp-Gly-Lys-Pro-Val (Ac-Lys-(Ac-Lys-Lys)Lys-SEQ ID NO: 1)
Ac-Lys-(Ac-Lys-Lys)Lys-Ser-Tyr-Ser-Met-Glu-His-(D-Phe)-Arg-Trp-Gly-Lys-Pro-Val
Ac-Lys-(Ac-Lys-Lys)Lys-Ser-Tyr-Ser-Met-Glu-His-Phe-(D-Arg)-Trp-Gly-Lys-Pro-Val
Ac-Lys-(Ac-Lys-Lys)Lys-Ser-Tyr-Ser-Met-Glu-His-Phe-Arg-(D-Trp)-Gly-Lys-Pro-Val
Ac-Lys-(Ac-Lys-Lys)Lys-Ser-Tyr-Ser-Met-Glu-His-(D-Phe)-Arg-(D-Trp)-Gly-Lys-Pro-Val
Ac-Lys-(Ac-Lys-Lys)Lys-Ser-Tyr-Ser-Met-Glu-His-Nal-Arg-Trp-Gly-Lys-Pro-Val
Ac-Lys-(Ac-Lys-Lys)Lys-Ser-Tyr-Ser-Met-Glu-His-(D-Nal)-Arg-Trp-Gly-Lys-Pro-Val
Ac-Lys-(Ac-Lys-Lys)Lys-Ser-Tyr-Ser-Met-Glu-His-Phe-Arg-Trp-Gly-Lys-Pro-(D-Val)
Ac-Lys-(Ac-Lys-Lys)Lys-Ser-Tyr-Ser-Met-Glu-His-(D-Phe)-Arg-Trp-Gly-Lys-Pro-(D-Val)
Ac-Lys-(Ac-Lys-Lys)Lys-Ser-Tyr-Ser-Met-Glu-His-Phe-(D-Arg)-Trp-Gly-Lys-Pro-(D-Val)
Ac-Lys-(Ac-Lys-Lys)Lys-Ser-Tyr-Ser-Met-Glu-His-Phe-Arg-(D-Trp)-Gly-Lys-Pro-(D-Val)
Ac-Lys-(Ac-Lys-Lys)Lys-Ser-Tyr-Ser-Met-Glu-His-(D-Phe)-Arg-(D-Trp)-Gly-Lys-Pro-(D-Val)
Ac-Lys-(Ac-Lys-Lys)Lys-Ser-Tyr-Ser-Met-Glu-His-Nal-Arg-Trp-Gly-Lys-Pro-(D-Val)
Ac-Lys-(Ac-Lys-Lys)Lys-Ser-Tyr-Ser-Met-Glu-His-(D-Nal)-Arg-Trp-Gly-Lys-Pro-(D-Val)
Ac-Lys-(Ac-Lys-Lys)Lys-Ser-Tyr-Ser-Nle-Glu-His-Phe-Arg-Trp-Gly-Lys-Pro-Val (Ac-Lys-(Ac-Lys-Lys)Lys-SEQ ID NO: 3)
Ac-Lys-(Ac-Lys-Lys)Lys-Ser-Tyr-Ser-Nle-Glu-His-(D-Phe)-Arg-Trp-Gly-Lys-Pro-Val
Ac-Lys-(Ac-Lys-Lys)Lys-Ser-Tyr-Ser-Nle-Glu-His-Phe-p-Arg)-Trp-Gly-Lys-Pro-Val
Ac-Lys-(Ac-Lys-Lys)Lys-Ser-Tyr-Ser-Nle-Glu-His-Phe-Arg-(D-Trp)-Gly-Lys-Pro-Val
Ac-Lys-(Ac-Lys-Lys)Lys-Ser-Tyr-Ser-Nle-Glu-His-(D-Phe)-Arg-(D-Trp)-Gly-Lys-Pro-Val
Ac-Lys-(Ac-Lys-Lys)Lys-Ser-Tyr-Ser-Nle-Glu-His-Nal-Arg-Trp-Gly-Lys-Pro-Val
Ac-Lys-(Ac-Lys-Lys)Lys-Ser-Tyr-Ser-Nle-Glu-His-(D-Nal)-Arg-Trp-Gly-Lys-Pro-Val
Ac-Lys-(Ac-Lys-Lys)Lys-Ser-Tyr-Ser-Nle-Glu-His-Phe-Arg-Trp-Gly-Lys-Pro-(D-Val)
Ac-Lys-(Ac-Lys-Lys)Lys-Ser-Tyr-Ser-Nle-Glu-His-(D-Phe)-Arg-Trp-Gly-Lys-Pro-(D-Val)
Ac-Lys-(Ac-Lys-Lys)Lys-Ser-Tyr-Ser-Nle-Glu-His-Phe-(D-Arg)-Trp-Gly-Lys-Pro-(D-Val)
Ac-Lys-(Ac-Lys-Lys)Lys-Ser-Tyr-Ser-Nle-Glu-His-Phe-Arg-(D-Trp)-Gly-Lys-Pre-(D-Val)
Ac-Lys-(Ac-Lys-Lys)Lys-Ser-Tyr-Ser-Nle-Glu-His-(D-Phe)-Arg-(D-Trp)-Gly-Lys-Pro-(D-Val)
Ac-Lys-(Ac-Lys-Lys)Lys-Ser-Tyr-Ser-Nle-Glu-His-Nal-Arg-Trp-Gly-Lys-Pro-(D-Val)
Ac-Lys-(Ac-Lys-Lys)Lys-Ser-Tyr-Ser-Nle-Glu-His-(D-Nal)-Arg-Trp-Gly-Lys-Pro-(D-Val)
Ac-Lys-(Ac-Lys-Lys)Lys-Ser-Ser-Ile-Ile-Ser-His-Phe-Arg-Trp-Gly-Lys-Pre-Val (Ac-Lys-(Ac-Lys-Lys)Lys-SEQ ID NO: 5)
Ac-Lys-(Ac-Lys-Lys)Lys-Ser-Ser-Ile-Ile-Ser-His-(D-Phe)-Arg-Trp-Gly-Lys-Pro-Val
Ac-Lys-(Ac-Lys-Lys)Lys-Ser-Ser-Ile-Ile-Ser-His-Phe-(D-Arg)-Trp-Gly-Lys-Pro-Val
Ac-Lys-(Ac-Lys-Lys)Lys-Ser-Ser-Ile-Ile-Ser-His-Phe-Arg-(D-Trp)-Gly-Lys-Pro-Val
Ac-Lys-(Ac-Lys-Lys)Lys-Ser-Ser-Ile-Ile-Ser-His-(D-Phe)-Arg-(D-Trp)-Gly-Lys-Val
Ac-Lys-(Ac-Lys-Lys)Lys-Ser-Ser-Ile-Ile-Ser-His-Nal-Arg-Trp-Gly-Lys-Pro-Val
Ac-Lys-(Ac-Lys-Lys)Lys-Ser-Ser-Ile-Ile-Ser-His-(D-Nal)-Arg-Trp-Gly-Lys-Pro-Val
Ac-Lys-(Ac-Lys-Lys)Lys-Ser-Ser-lie-Ile-Ser-His-Phe-Arg-Trp-Gly-Lys-Pro-(D-Val)
Ac-Lys-(Ac-Lys-Lys)Lys-Ser-Ser-Ile-Ile-Ser-His-(D-Phe)-Arg-Trp-Gly-Lys-Pro-(D-Val)
Ac-Lys-(Ac-Lys-Lys)Lys-Ser-Ser-Ile-Ile-Ser-His-Phe-(D-Arg)-Trp-Gly-Lys-Pro-(D-Val)
Ac-Lys-(Ac-Lys-Lys)Lys-Ser-Ser-Ile-Ile-Ser-His-Phe-Arg-(D-Trp)-Gly-Lys-Pro-(D-Val)
Ac-Lys-(Ac-Lys-Lys)Lys-Ser-Ser-Ile-Ile-Ser-His-(D-Phe)-Arg-(D-Trp)-Gly-Lys-Pro-(D-Val)
Ac-Lys-(Ac-Lys-Lys)Lys-Ser-Ser-Ile-Ile-Ser-His-Nal-Arg-Trp-Gly-Lys-Pro-(D-Val)
Ac-Lys-(Ac-Lys-Lys)Lys-Ser-Ser-Ile-Ile-Ser-His-(D-Nal)-Arg-Trp-Gly-Lys-Pro-(D-Val)
The C-terminal Valine may be amidated (NH$_2$).

X = Ac-(Ac-Lys)Lya-(Ac-Lys)Lys-:
Ac-(Ac-Lys)Lys-(Ac-Lys-)Lys-Ser-Tyr-Ser-Met-Glu-His-Phe-Arg-Trp-Gly-Lys-Pro-Val (Ac-(Ac-Lys)Lys-(Ac-Lys-)Lys-SEQ ID NO: 1)
Ac-(Ac-Lys)Lys-(Ac-Lys-)Lys-Ser-Tyr-Ser-Met-Glu-His-(D-Phe)-Arg-Trp-Gly-Lys-Pro-Val
Ac-(Ac-Lys)Lys-(Ac-Lys-)Lys-Ser-Tyr-Ser-Met-Glu-His-Phe-(D-Arg)-Trp-Gly-Lys-Pro-Val
Ac-(Ac-Lys)Lys-(Ac-Lys-)Lys-Ser-Tyr-Ser-Met-Glu-His-Phe-Arg-(D-Trp)-Gly-Lys-Pro-Val
Ac-(Ac-Lys)Lys-(Ac-Lys-)Lys-Ser-Tyr-Ser-Met-Glu-His-(D-Phe)-Arg-(D-Trp)-Gly-Lys-Pro-Val
Ac-(Ac-Lys)Lys-(Ac-Lys-)Lys-Ser-Tyr-Ser-Met-Glu-His-Nal-Arg-Trp-Gly-Lys-Pro-Val
Ac-(Ac-Lys)Lys-(Ac-Lys-)Lys-Ser-Tyr-Ser-Met-Glu-His-(D-Nal)-Arg-Trp-Gly-Lys-Pro-Val
Ac-(Ac-Lys)Lys-(Ac-Lys-)Lys-Ser-Tyr-Ser-Met-Glu-His-Phe-Arg-Trp-Gly-Lys-Pro-(D-Val)
Ac-(Ac-Lys)Lys-(Ac-Lys-)Lys-Ser-Tyr-Ser-Met-Glu-His-(D-Phe)-Arg-Trp-Gly-Lys-Pro-(D-Val)
Ac-(Ac-Lys)Lys-(Ac-Lys-)Lys-Ser-Tyr-Ser-Met-Glu-His-Phe-(D-Arg)-Trp-Gly-Lys-Pro-(D-Val)
Ac-(Ac-Lys)Lys-(Ac-Lys-)Lys-Ser-Tyr-Ser-Met-Glu-His-Phe-Arg-(D-Trp)-Gly-Lys-Pro (D-Val)
Pro-(D-Val)

APPENDIX-continued

Examples of sequences of MSH analogues

Ac-(Ac-Lys)Lys-(Ac-Lys-)Lys-Ser-Tyr-Ser-Met-Glu-His-Nal-Arg-Trp-Gly-Lys-Pro-(D-Val)
Ac-(Ac-Lys)Lys-(Ac-Lys-)Lys-Ser-Tyr-Ser-Met-Glu-His-(D-Nal)-Arg-Trp-Gly-Lys-Pro-(D-Val)
Ac-(Ac-Lys)Lys-(Ac-Lys-)Lys-Ser-Tyr-Ser-Nle-Glu-His-Phe-Arg-Trp-Gly-Lys-Pro-Val (Ac-(Ac-Lys)Lys-(Ac-Lys-)Lys-SEQ ID NO: 3)
Ac-(Ac-Lys)Lys-(Ac-Lys-)Lys-Ser-Tyr-Ser-Nle-Glu-His-(D-Phe)-Arg-Trp-Gly-Lys-Pro-Val
Ac-(Ac-Lys)Lys-(Ac-Lys-)Lys-Ser-Tyr-Ser-Nle-Glu-His-Phe-(D-Arg)-Trp-Gly-Lys-Pro-Val
Ac-(Ac-Lys)Lys-(Ac-Lys-)Lys-Ser-Tyr-Ser-Nle-Glu-His-Phe-Arg-(D-Trp)-Gly-Lys-Pro-Val
Ac-(Ac-Lys)Lys-(Ac-Lys-)Lys-Ser-Tyr-Ser-Nle-Glu-His-(D-Phe)-Arg-(D-Trp)-Gly-Lys-Pro-Val
Ac-(Ac-Lys)Lys-(Ac-Lys-)Lys-Ser-Tyr-Ser-Nle-Glu-His-Nal-Arg-Trp-Gly-Lys-Pro-Val
Ac-(Ac-Lys)Lys-(Ac-Lys-)Lys-Ser-Tyr-Ser-Nle-Glu-His-(D-Nal)-Arg-Trp-Gly-Lys-Pro-Val
Ac-(Ac-Lys)Lys-(Ac-Lys-)Lys-Ser-Tyr-Ser-Nle-Glu-His-Phe-Arg-Trp-Gly-Lys-Pro-(D-Val)
Ac-(Ac-Lys)Lys-(Ac-Lys-)Lys-Ser-Tyr-Ser-Nle-Glu-His-(D-Phe)-Arg-Trp-Gly-Lys-Pro-(D-Val)
Ac-(Ac-Lys)Lys-(Ac-Lys-)Lys-Ser-Tyr-Ser-Nle-Glu-His-Phe-(D-Arg)-Trp-Gly-Lys-Pro-(D-Val)
Ac-(Ac-Lys)Lys-(Ac-Lys-)Lys-Ser-Tyr-Ser-Nle-Glu-His-Phe-Arg-(D-Trp)-Gly-Lys-Pro-(D-Val)
Ac-(Ac-Lys)Lys-(Ac-Lys-)Lys-Ser-Tyr-Ser-Nle-Glu-His(D-Phe)-Arg-(D-Trp)-Gly-Lys-Pro-(D-Val)
Ac-(Ac-Lys)Lys-(Ac-Lys-)Lys-Ser-Tyr-Ser-Nle-Glu-His-Nal-Arg-Trp-Gly-Lys-Pro-(D-Val)
Ac-(Ac-Lys)Lys-(Ac-Lys-)Lys-Ser-Tyr-Ser-Nle-Glu-His-(D-Nal)-Arg-Trp-Gly-Lys-Pro-(D-Val)
Ac-(Ac-Lys)Lys-(Ac-Lys-)Lys-Ser-Ser-Ile-Ile-Ser-His-Phe-Arg-Trp-Gly-Lys-Pro-Val (Ac-(Ac-Lys)Lys-(Ac-Lys-)Lys-SEQ ID NO: 5)
Ac-(As-Lys)Lys-(Ac-Lys-)Lys-Ser-Ser-Ile-IIe-Ser-His-(D-Phe)-Arg-Trp-Gly-Lys-Pro-Val
Ac-(Ac-Lys)Lys-(Ac-Lys-)Lys-Ser-Ser-Ile-Ile-Ser-His-Phe-(D-Arg)-Trp-Gly-Lys-Pro-Val
Ac-(Ac-Lys)Lys-(Ac-Lys-)Lys-Ser-Ser-Ile-Ile-Ser-His-Phe-Arg-(D-Trp)-Gly-Lys-Pro-Val
Ac-(Ac-Lys)Lys-(Ac-Lys-)Lys-Ser-Ser-lIe-Ile-Ser-His-(D-Phel-Arg-(D-Trp)-Gly-Lys-Pro-Val
Ac-(Ac-Lys)Lys-(Ac-Lys-)Lys-Ser-Ser-Ile-Ile-Ser-His-Nal-Arg-Trp-Gly-Lys-Pro-Val
Ac-(Ac-Lys)Lys-(Ac-Lys-)Lys-Ser-Ser-Ile-Ile-Ser-His-(D-Nal)-Arg-Trp-Gly-Lys-Pro-Val
Ac-(Ac-Lys)Lys-(Ac-Lys-)Lys-Ser-Ser-Ile-Ile-Ser-His-Phe-Arg-Trp-Gly-Lys-Pro-(D-Val)
Ac-(Ac-Lys)Lys-(Ac-Lys-)Lys-Ser-Ser-lIe-Ile-Ser-His-(D-Phe)-Arg-Trp-Gly-Lys-Pro-(D-Val)
Ac-(Ac-Lys)Lys-(Ac-Lys-)Lys-Ser-Ser-Ile-Ile-Ser-His-Phe-(D-Arg)-Trp-Gly-Lys-Pro-(D-Val)
Ac-(Ac-Lys)Lys-(Ac-Lys-)Lys-Ser-Ser-Ile-Ile-Ser-His-Phe-Arg-(D-Trp)-Gly-Lys-Pro-(D-Val)
Ac-(Ac-Lys)Lys-(Ac-Lys-)Lys-Ser-Ser-Ile-Ile-Ser-His-(D-Phe)-Arg-(D-Trp)-Gly-Lys-Pro-(D-Val)
Ac-(Ac-Lys)Lys-(Ac-Lys-)Lys-Ser-Ser-Ile-Ile-Ser-His-Nal-Arg-Trp-Gly-Lys-Pro-(D-Val)
Ac-(Ac-Lys)Lys-(Ac-Lys-)Lys-Ser-Ser-Ile-Ile-Ser-His-(D-NaI)-Arg-Trp-Gly-Lys-Pro-(D-Val)
The C-terminal Valine may be amidated (NH$_2$)

X = Ac-Lys-Lys-(Ac-Lys)Lys-:
Ac-Lys-Lys-(Ac-Lys)Lys-Ser-Tyr-Ser-Met-Glu-His-Phe-Arg-Trp-Gly-Lys-Pro-Val (Ac-Lys-Lys-(Ac-Lys)Lys-SEQ ID NO: 1)
Ac-Lys-Lys-(Ac-Lys)Lys-Ser-Tyr-Ser-Met-Glu-His-(D-Phe)-Arg-Trp-Gly-Lys-Pro-Val
Ac-Lys-Lys-(Ac-Lys)Lys-Ser-Tyr-Ser-Met-Glu-His-Phe-(D-Arg)-Trp-Gly-Lys-Pro-Val
Ac-Lys-Lys-(Ac-Lys)Lys-Ser-Tyr-Ser-Met-Glu-His-Phe-Arg-(D-Trp)-Gly-Lys-Pro-Val
Ac-Lys-Lys-(Ac-Lys)Lys-Ser-Tyr-Ser-Met-Glu-His-(D-Phe)-Arg-(D-Trp)-Gly-Lys-Pro-Val
Ac-Lys-Lys-(Ac-Lys)Lys-Ser-Tyr-Ser-Met-Glu-His-Nal-Arg-Trp-Gly-Lys-Pro-Val
Ac-Lys-Lys-(Ac-Lys)Lys-Ser-Tyr-Ser-Met-Glu-His-(D-Nal)-Arg-Trp-Gly-Lys-Pro-Val
Ac-Lys-Lys-(Ac-Lys)Lys-Ser-Tyr-Ser-Met-Glu-His-Phe-Arg-Trp-Gly-Lys-Pro-(D-Val)
Ac-Lys-Lys-(Ac-Lys)Lys-Ser-Tyr-Ser-Met-Glu-His-(D-Phe)-Arg-Trp-Gly-Lys-Pro-(D-Val)
Ac-Lys-Lys-(Ac-Lys)Lys-Ser-Tyr-Ser-Met-Glu-His-Phe-(D-Arg)-Trp-Gly-Lys-Pro-(D-Val)
Ac-Lys-Lys-(Ac-Lys)Lys-Ser-TYr-Ser-Met-Glu-His-Phe-Arg-(D-Trp)-Gly-Lys-Pro-(D-Val)
Ac-Lys-Lys-(Ac-Lys)Lys-Ser-Tyr-Ser-Met-Glu-His-(D-Phe)-Arg-(D-Trp)-Gly-Lys-Pro-(D-Val)
Ac-Lys-Lys-(Ac-Lys)Lys-Ser-Tyr-Ser-Met-Glu-His-Nal-Arg-Trp-Gly-Lys-Pro-(D-Val)
Ac-Lys-Lys-(Ac-Lys)Lys-Ser-Tyr-Ser-Met-Glu-His-(D-Nal)-Arg-Trp-Gly-Lys-Pro-(D-Val)
Ac-Lys-Lys-(Ac-Lys)Lys-Ser-Tyr-Ser-Nle-Glu-His-Phe-Arg-Trp-Gly-Lys-Pro-Val (Ac-Lys-Lys-(Ac-Lys)Lys-SEQ ID NO: 3)
Ac-Lys-Lys-(Ac-Lys)Lys-Ser-Tyr-Ser-Nle-Glu-His-(D-Phe)-Arg-Trp-Gly-Lys-Pro-Val
Ac-Lys-Lys-(Ac-Lys)Lys-Ser-Tyr-Ser-Nle-Glu-His-Phe-(D-Arg)-Trp-Gly-Lys-Pro-Val
Ac-Lys-Lys-(Ac-Lys)Lys-Ser-Tyr-Ser-Nle-Glu-His-Phe-Arg-(D-Trp)-Gly-Lys-Pro-Val
Ac-Lys-Lys-(Ac-Lys)Lys-Ser-Tyr-Ser-Nle-Glu-His-(D-Phs)-Arg-(D-Trp)-Gly-Lys-Pro-Val
Ac-Lys-Lys-(Ac-Lys)Lys-Ser-Tyr-Ser-Nle-Glu-His-Nal-Arg-Trp-Gly-Lys-Pro-Val
Ac-Lys-Lys-(Ac-Lys)Lys-Ser-Tyr-Ser-Nle-Glu-His-(D-Nal)-Arg-Trp-Giy-Lys-Pro-Val
Ac-Lys-Lys-(Ac-Lys)Lys-Ser-Tyr-Ser-Nle-Glu-His-Phe-Arg-Trp-Gly-Lys-Pro-(D-Val)
Ac-Lys-Lys-(Ac-Lys)Lys-Ser-Tyr-Ser-Nle-Glu-His-(D-Phe)-Arg-Trp-Gly-Lys-Pro-(D-Val)

APPENDIX-continued

Examples of sequences of MSH analogues

```
Ac-Lys-Lys-(Ac-Lys)Lys-Ser-Tyr-Ser-Nle-Glu-His-Phe-(D-Arg)-Trp-Gly-Lys-Pro-(D-Val)
Ac-Lys-Lys-(Ac-Lys)Lys-Ser-Tyr-Ser-Nle-Glu-His-Pho-Arg-(D-Trp)-Gly-Lys-Pro-(D-Val)
Ac-Lys-Lys-(Ac-Lys)Lys-Ser-Tyr-Ser-Nle-Glu-His-(D-Phe)-Arg-(D-Trp)-Gly-Lys-Pro-(D-
Val)
Ac-Lys-Lys-(Ac-Lys)Lys Ser-Tyr-Ser-Nle-Glu-His-Nal-Arg-Trp-Gly-Lys-Pro-M-Val)
Ac-Lys-Lys-(Ac-Lys)Lys-Ser-Tyr-Ser-Nle-Glu-His-(D-Nal)-Arg-Trp-Gly-Lys-Pro-(D-Val)
Ac-Lys-Lys-(Ac-Lys)Lys-Ser-Ser-Ile-Ile-Ser-His-Phe-Arg-Trp-Gly-Lys-Pro-Val (Ac-Lys-
Lys-(Ac-Lys)Lys-SEQ ID NO: 5)
Ac-Lys-Lys-(Ac-Lys)Lys-Ser-Ser-Ile-Ile-Ser-His-(D-Phe)-Arg-Trp-Gly-Lys-Pro-Val
Ac-Lys-Lys-(Ac-Lys)Lys-Ser-Ser-Ile-Ile-Ser-His-Phe-(D-Arg)-Trp-Gly-Lys-Pro-Val
Ac-Lys-Lys-(Ac-Lys)Lys-Ser-Ser-Ile-Ile-Ser-His-Phe-Arg-(D-Trp)-Gly-Lys-Pro-Val
Ac-Lys-Lys-(Ac-Lys)Lys-Ser-Ser-Ile-Ile-Ser-His-(D-Phe)-Arg-(D-Trp)-Gly-Lys-Pro-Val
Ac-Lys-Lys-(Ac-Lys)Lys-Ser-Ser-Ile-Ile-Ser-His-Nal-Arg-Trp-Gly-Lys-Pro-Val
Ac-Lys-Lys-(Ac-Lys)Lys-Ser-Ser-Ile-Ile-Ser-His-(D-Nal)-Arg-Trp-Gly-Lys-Pro-Val
Ac-Lys-Lys-(Ac-Lys)Lys-Ser-Ser-Ile-Ile-Ser-His-Phe-Arg-Trp-Gly-Lys-Pro-(D-Val)
Ac-Lys-Lys-(Ac-Lys)Lys-Ser-Ser-Ile-Ile-Ser-His-(D-Phe)-Arg-Trp-Gly-Lys-Pro-(D-Val)
Ao-Lys-Lys-(Ac-Lys)Lys-Ser-Ser-Ile-Ile-Ser-His-Phe-(D-Arg)-Tro-Gly-Lys-Pro-(D-Val)
Ac-Lys-Lys-(Ac-Lys)Lys-Ser-Ser-Ile-Ile-Ser-His-Phe-Arg-(D-Trp)-Gly-Lys-Pro-(D-Val)
Ac-Lys-Lys-(Ac-Lys)Lys-Ser-Ser-Ile-ile-Ser-His-(D-Phe)-Arg-(D-Trp)-Gly-Lys-Pro-(D-
Val)
Ac-Lys-Lys-(Ac-Lys)Lys-Ser-Ser-Ile-Ile-Ser-His-Nal-Arg-Trp-Gly-Lys-Pro-(D-Val)
Ac-Lys-Lys-(Ac-Lys)Lys-Ser-Ser-Ile-Ile-Ser-His-(D-Nal)-Arg-Trp-Gly-Lys-Pro-(D-Val)
The C-terminal may be amidated (NH2).

X = Ac-Lys-(Ac-Lys)Lys-Lys-:
Ac-Lys-(Ac-Lys)Lys-Lys-Ser-Tyr-Ser-Met-Glu-His-Phe-Arg-Trp-Gly-Lys-Pro-Val (Ac-
Lys-(Ac-Lys)Lys-Lys-SEQ ID NO: 1)
Ac-Lys-(Ac-Lys)Lys-Lys-Ser-Tyr-Ser-Met-Glu-His-(D-Phe)-Arg-Trp-Gly-Lys-Pro-Val
Ac-Lys-(Ac-Lys)Lys-Lys-Ser-Tyr-Ser-Met-Glu-His-Phe-(D-Arg)-Trp-Gly-Lys-Pro-Val
Ac-Lys-(Ac-Lys)Lys-Lys-Ser-Tyr-Ser-Met-Glu-His-Phe-Arg-(D-Trp)-Gly-Lys-Pro-Val
Ac-Lys-(Ac-Lys)Lys-Lys-Ser-Tyr-Ser-Met-Glu-His-(D-Phe)-Arg-(D-Trp)-Gly-Lys-Pro-Val
Ac-Lys-(Ac-Lys)Lys-Lys-Ser-Tyr-Ser-Met-Glu-His-Nal-Arg-Trp-Gly-Lys-Pro-Val
Ac-Lys-(Ac-Lys)Lys-Lys-Ser-Tyr-Ser-Met-Glu-His-(D-Nal)-Arg-Trp-Gly-Lys-Pro-Val
Ac-Lys-(Ac-Lys)Lys-Lys-Ser-Tyr-Ser-Met-Glu-His-Phe-Arg-Trp-Gly-Lys-Pro-(D-Val)
Ac-Lys-(Ac-Lys)Lys-Lys-Ser-Tyr-Ser-Met-Glu-His-(D-Phe)-Arg-Trp-Gly-Lys-Pro-(D-Val)
Ac-Lys-(Ac-Lys)Lys-Lys-Ser-Tyr-Ser-Met-Glu-His-Phe-(D-Arg)-Trp-Gly-Lys-Pro-(D-Val)
Ac-Lys-(Ac-Lys)Lys-Lys-Ser-Tyr-Ser-Met-Glu-His-Phe-Arg-(D-Trp)-Gly-Lys-Pro-(D-Val)
Ac-Lys-(Ac-Lys)Lys-Lys-Ser-Tyr-Ser-Met-Glu-His-(D-Phe)-Arg-(D-Trp)-Gly-Lys-Pro-(D-Val)
Ac-Lys-(Ac-Lys)Lys-Lys-Ser-Tyr-Ser-Met-Glu-His-Nal-Arg-Trp-Gly-Lys-Pro-(D-Val)
Ac-Lys-(Ac-Lys)Lys-Lys-Ser-Tyr-Ser-Met-Glu-His-(D-Nal)-Arg-Trp-Gly-Lys-Pro-(D-Val)
Ac-Lys-(Ac-Lys)Lys-Lys-Ser-Tyr-Ser-Nle-Glu-His-Pho-Arg-Trp-Gly-Lys-Pro-Val
Ac-Lys-(Ac-Lys)Lys-Lys-Ser-Tyr-Ser-Nle-Glu-His-(D-Phe)-Arg-Trp-Gly-Lys-Pro-
Ac-Lys-(Ac-Lys)Lys-Lys-Ser-Tyr-Ser-Nle-Glu-His-Phe-(D-Arg)-Trp-Gly-Lys-Pro-Val
Ac-Lys-(Ac-Lys)Lys-Lys-Ser-Tyr-Ser-Nle-Glu-His-Phe-Arg-(D-Trp)-Gly-Lys-Pro-Val
Ac-Lys-(Ac-Lys)Lys-Lys-Ser-Tyr-Ser-Nle-Glu-His-(D-Phey-Arg-(D-Trp)-Gly-Lys-Pro-Val
Ac-Lys-(Ac-Lys)Lys-Lys-Ser-Tyr-Ser-Nle-Glu-His-Nal-Arg-Trp-Gly-Lys-Pro-Val (Ac-Lys-
(Ac-Lys)Lys-Lys-SEQ ID NO: 3)
Ac-Lys-(Ac-Lys)Lys-Lys-Ser-Tyr-Ser-Nle-Glu-His-(D-Nal)-Arg-Trp-Gly-Lys-Pro-Val
Ac-Lys-(Ac-Lys)Lys-Lys-Ser-Tyr-Ser-Nle-Glu-His-Phe-Arg-Trp-Gly-Lys-Pro-(D-Val)
Ac-Lys-(Ac-Lys)Lys-Lys-Ser-Tyr-Ser-Nle-Glu-His-(D-Phe)-Arg-Trp-Gly-Lys-Pro-(D-Val)
Ac-Lys-(Ac-Lys)Lys-Lys-Ser-Tyr-Ser-Nle-Glu-His-Phe-(D-Arg)-Trp-Gly-Lys-Pro-(D-Val)
Ac-Lys-(Ac-Lys)Lys-Lys-Ser-Tyr-Ser-Nle-Glu-His-Phe-Arg-(D-Trp)-Gly-Lys-Pro-(D-Val)
Ac-Lys-(Ac-Lys)Lys-Lys-Ser-Tyr-Ser-Nle-Glu-His-(D-Phe)-Arg-(D-Trp)-Gly-Lys-Pro-(D-
Val)
Ac-Lys-(Ac-Lys)Lys-Lys-Ser-Tyr-Ser-Nle-Glu-His-Nal-Arg-Trp-Gly-Lys-Pro-(D-Val)
Ac-Lys-(Ac-Lys)Lys-Lys-Ser-Tyr-Ser-Nle-Glu-His-(D-Nal)-Arg-Trp-Gly-Lys-Pro-(D-Val)
Ac-Lys-(Ac-Lys)Lys-Lys-Ser-Ser-Ile-Ile-Ser-His-Phe-Arg-Trp-Gly-Lys-Pro-Val (Ac-Lys-
(Ac-Lys)Lys-Lys-SEQ ID NO: 5)
Ac-Lys-(Ac-Lys)Lys-Lys-Ser-Ser-Ile-Ile-Ser-His-(D-Phe)-Arg-Trp-Gly-Lys-Pro-Val
Ac-Lys-(Ac-Lys)Lys-Lys-Ser-Ser-Ile-Ile-Ser-His-Phe-(D-Arg)-Trp-Gly-Lys-Pro-Val
Ac-Lys-(Ac-Lys)Lys-Lys-Ser-Ser-Ile-Ile-Ser-His-Phe-Arg-(D-Trp)-Gly-Lys-Pro-Val
Ac-Lys-(Ac-Lys)Lys-Lys-Ser-Ser-Ile-Ile-Ser-His-(D-Phe)-Arg-(D-Trp)-Gly-Lys-Pro-Val
Ac-Lys-(Ac-Lys)Lys-Lys-Ser-Ser-Ile-Ile-Ser-His-Nal-Arg-Trp-Gly-Lys-Pro-Val
Ac-Lys-(Ac-Lys)Lys-Lys-Ser-Ser-Ile-Ile-Ser-His-(D-Nal)-Arg-Trp-Gly-Lys-Pro-Val
Ac-Lys-(Ac-Lys)Lys-Lys-Ser-Ser-Ile-Ile-Ser-His-Phe-Arg-Trp-Gly-Lys-Pro-(D-Val)
Ac-Lys-(Ac-Lys)Lys-Lys-Ser-Ser-Ile-Ile-Ser-His-(D-Phe)-Arg-Trp-Gly-Lys-Pro-(D-Val)
Ac-Lys-(Ac-Lys)Lys-lys-Ser-Ser-Ile-Ile-Ser-His-Phe-(D-Arg)-Trp-Gly-Lys-Pro-(D-Val)
Ac-Lys-(Ac-Lys)Lys-Lys-Ser-Ser-Ile-Ile-Ser-His-Phe-Arg-(D-Trp)-Gly-Lys-Pro-(D-Val)
Ac-Lys-(Ac-Lys)Lys-Lys-Ser-Ser-Ile-Ile-Ser-His-(D-Phe)-Arg-(D-Trp)-Gly-Lys-Pro-(D-
Val)
Ac-Lys-(Ac-Lys)Lys-Lys-Ser-Ser-Ile-Ile-Ser-His-Nal-Arg-Trp-Gly-Lys-Pro-(D-Val)
Ac-Lys-(Ac-Lys)Lys-Lys-Ser-Ser-Ile-Ile-Ser-His-(D-Nal)-Arg-Trp-Gly-Lys-Pro-(D-Val)
The C-terminal Valine may be amidated (NH$_2$).

X = Ac-(Ac-Lys)Lys-Lys-Lys-:
Ac-(Ac-Lys)Lys-Lys-Lys-Ser-Tyr-Ser-Met-Glu-His-Phe-Arg-Trp-Gly-Lys-Pro-Val (Ac-
(Ac-Lys)Lys-Lys-Lys-SEQ ID NO: 1)
Ac-(Ac-Lys)Lys-Lys-Lys-Ser-Tyr-Ser-Met-Glu-His-(D-Phe)-Arg-Trp-Gly-Lys-Pro-Val
```

APPENDIX-continued

Examples of sequences of MSH analogues

Ac-(Ac-Lys)Lys-Lys-Lys-Ser-Tyr-Ser-Met-Glu-His-Phe-(D-Arg)-Trp-Gly-Lys-Pro-Val
Ac-(Ac-Lys)Lys-Lys-Lys-Ser-Tyr-Ser-Met-Glu-His-Phe-Arg-(D-Trp)-Gly-Lys-Pro-Val
Ac-(Ac-Lys)Lys-Lys-Lys-Ser-Tyr-Ser-Met-Glu-His-(D-Phe)-Arg-(D-Trp)-Gly-Lys-Pro-Val
Ac-(Ac-Lys)Lys-Lys-Lys-Ser-Tyr-Ser-Met-Glu-His-Nal-Arg-Trp-Gly-Lys-Pro-Val
Ac-(Ac-Lys)Lys-Lys-Lys-Ser-Tyr-Ser-Met-Glu-His-(D-Nal)-Arg-Trp-Gly-Lys-Pro-Val
Ac-(Ac-Lys)Lys-Lys-Lys-Ser-Tyr-Ser-Met-Glu-His-Phe-Arg-Trp-Gly-Lys-Pro-(D-Val)
Ac-(Ac-Lys)Lys-Lys-Lys-Ser-Tyr-Ser-Met-Glu-His-(D-Phe)-Arg-Trp-Gly-Lys-Pro-(D-Val)
Ac-(Ac-Lys)Lys-Lys-Lys-Ser-Tyr-Ser-Met-Glu-His-Phe-(D-Arg)-Trp-Gly-Lys-Pro-(D-Val)
Ac-(Ac-Lys)Lys-Lys-Lys-Ser-Tyr-Ser-Met-Glu-His-Phe-Arg-(D-Trp)-Gly-Lys-Pro-(D-Val)
Ac-(Ac-Lys)Lys-Lys-Lys-Ser-Tyr-Ser-Met-Glu-His-(D-Phe)-Arg-(D-Trp)-Gly-Lys-Pro-(D-Val)
Ac-(As-Lys)Lys-Lys-Lys-Ser-Tyr-Ser-Met-Glu-His-Nal-Arg-Trp-Gly-Lys-Pro-(D-Val)
Ac-(Ac-Lys)Lys-Lys-Lys-Ser-Tyr-Ser-Met-Glu-His-(D-Nal)-Arg-Trp-Gly-Lys-Pro-(D-Val)
Ac-(Ac-Lys)Lys-Lys-Lys-Ser-Tyr-Ser-Nle-Glu-His-Phe-Arg-Trp-Gly-Lys-Pro-Val (Ac-(Ac-Lys)Lys-Lys-Lys-SEQ ID NO: 3)
Ac-(Ac-Lys)Lys-Lys-Lys-Ser-Tyr-Ser-Nle-Glu-His-(D-Phe)-Arg-Trp-Gly-Lys-Pro-Val
Ac-(Ac-Lys)Lys-Lys-Lys-Ser-Tyr-Ser-Nle-Glu-His-Phe-(D-Arg)-Trp-Gly-Lys-Pro-Val
Ac-(Ac-Lys)Lys-Lys-Lys-Ser-Tyr-Ser-Nle-Glu-His-Phe-Arg-(D-Trp)-Gly-Lys-Pro-Val
Ac-(Ac-Lys)Lys-Lys-Lys-Ser-Tyr-Ser-Nle-Glu-His-(D-Phe)-Arg-(D-Trp)-Gly-Lys-Pro-Val
Ac-(Ac-Lys)Lys-Lys-Lys-Ser-Tyr-Ser-Nle-Glu-His-Nal-Arg-Trp-Gly-Lys-Pro-Val
Ac-(Ac-Lys)Lys-Lys-Lys-Ser-Tyr-Ser-Nle-Glu-His-(D-Nal)-Arg-Trp-Gly-Lys-Pro-Val
Ac-(Ac-Lys)Lys-Lys-Lys-Ser-Tyr-Ser-Nle-Glu-His-Phe-Arg-Trp-Gly-Lys-Pro-(D-Val)
Ac-(Ac-Lys)Lys-Lys-Lys-Ser-Tyr-Ser-Nle-Glu-His-(D-Phe)-Arg-Trp-Gly-Lys-Pro-(D-Val)
Ac-(Ac-Lys)Lys-Lys-Lys-Ser-Tyr-Ser-Nle-Glu-His-Phe-(D-Arg)-Trp-Gly-Lys-Pro-(D-Val)
Ac-(Ac-Lys)Lys-Lys-Lys-Ser-Tyr-Ser-Nle-Glu-His-Phe-Arg-(D-Trp)-Gly-Lys-Pro-(D-Val)
Ac-(Ac-Lys)Lys-Lys-Lys-Ser-Tyr-Ser-Nle-Glu-His-(D-Phe)-Arg-(D-Trp)-Gly-Lys-Pro-(D-Val)
Ac-(Ac-Lys)Lys-Lys-Lys-Ser-Tyr-Ser-Nle-Glu-His-Nal-Arg-T-Gly-Lys-Pro-(D-Val)
Ac-(Ac-Lys)Lys-Lys-Lys-Ser-Tyr-Ser-Nle-Glu-His-(D-Nal)-Arg-Trp-Gly-Lys-Pro-(D-Val)
Ac-(Ac-Lys)Lys-Lys-Lys-Ser-Ser-Ile-Ile-Ser-His-Phe-Arg-Trp-Gly-Lys-Pro-Val (Ac-(Ac-Lys)Lys-Lys-Lys-SEQ ID NO: 5)
Ac-(Ac-Lys)Lys-Lys-Lys-Ser-Ser-Ile-Ile-Ser-His-(D-Phe)-Arg-Trp-Gly-Lys-Pro-Val
Ac-(Ac-Lys)Lys-Lys-Lys-Ser-Ser-Ile-Ile-Ser-His-Phe-(D-Arg)-Trp-Gly-Lys-Pro-Val
Ac-(Ac-Lys)Lys-Lys-Lys-Ser-Ser-Ile-Ile-Ser-His-Phe-Arg-(D-Trp)-Gly-Lys-Pro-Val
Ac-(Ac-Lys)Lys-Lys-Lys-Ser-Ser-Ile-Ile-Ser-His-(D-Phe)-Arg-(D-Trp)-Gly-Lys-Pro-Val
Ac-(Ac-Lys)Lys-Lys-Lys-Ser-Ser-Ile-Ile-Ser-His-Nal-Arg-Trp-Gly-Lys-Pro-Val
Ac-(Ac-Lys)Lys-Lys-Lys-Ser-Ser-Ile-Ile-Ser-His-(D-Nal)-Arg-Trp-Gly-Lys-Pro-Val
Ac-(Ac-Lys)Lys-Lys-Lys-Ser-Ser-Ile-Ile-Ser-His-Phe-Arg-Trp-Gly-Lys-Pro-(D-Val)
Ac-(Ac-Lys)Lys-Lys-Lys-ser-Ser-Ile-Ile-Ser-His-(D-Phe)-Arg-Trp-Gly-Lys-Pro-(D-Val)
Ac-(Ac-Lys)Lys-Lys-Lys-Ser-Ser-Ile-Ile-Ser-His-Phe-(D-Arg)-Trp-Gly-Lys-Pro-(D-Val)
Ac-(Ae-Lys)Lys-Lys-Lys-Ser-Ser-Ile-Ile-Ser-His-Phe-Arg-(D-Trp)-Gly-Lys-Pro-(D-Val)
Ac-(Ao-Lys)Lys-Lys-Lys-Ser-Ser-Ile-Ile-Ser-His-(D-Phe)-Arg-(D-Trp)-Gly-Lys-Pro-(D-Val)
Ac-(Ac-Lys)Lys-Lys-Lys-Ser-Ser-Ile-Ile-Ser-His-Nal-Arg-Trp-Gly-Lys-Pro-(D-Val)
Ac-(Ac-Lys)Lys-Lys-Lys-Ser-Ser-Ile-Ile-Ser-His-(D-Nal)-Arg-Trp-Gly-Lys-Pro-(D-Val)
The C-terminal Valine may be amidated (NH2).

X = Ac-(Ac-Lys-Gly)Lys-Lys-:
Ac-(Ac-Lys-Gly)Lys-Lys-Ser-Tyr-Ser-Met-Glu-His-Phe-Arg-Trp-Gly-Lys-Pro-Val (Ac-(Ac-Lys-Gly)Lys-Lys-SEQ ID NO: 1)
Ac-(Ac-Lys-Gly)Lys-Lys-Ser-Tyr-Ser-Met-Glu-His-(D-Phe)-Arg-Trp-Gly-Lys-Pro-Val
Ac-(Ac-Lys-Gly)Lys-Lys-Ser-Tyr-Ser-Met-Glu-His-Phe-(D-Arg)-Trp-Gly-Lys-Pro-Val
Ac-(Ac-Lys-Gly)Lys-Lys-Ser-Tyr-Ser-Met-Glu-His-Phe-Arg-(D-Trp)-Gly-Lys-Pro-Val
Ac-(Ac-Lys-Gly)Lys-Lys-Ser-Tyr-Ser-Met-Glu-His-(D-Phe)-Arg-(D-Trp)-Gly-Lys-Pro-Val
Ac-(Ac-Lys-Gly)Lys-Lys-Ser-Tyr-Ser-Met-Glu-His-Nal-Arg-Trp-Gly-Lys-Pro-Val
Ac-(Ac-Lys-Gly)Lys-Lys-Ser-Tyr-Ser-Met-Glu-His-(D-Nal)-Arg-Trp-Gly-Lys-Pro-Val
Ac-(Ac-Lys-Gly)Lys-LYs-Ser-Tyr-Ser-Met-Glu-His-Phe-Arg-Trp-Gly-Lys-Pro-(D-Val)
Ac-(Ac-Lys-Gly)Lys-Lys-Ser-Tyr-Ser-Met-Glu-His-(D-Phe)-Arg-Trp-Gly-Lys-Pro-(D-Val)
Ac-(Ac-Lys-Gly)Lys-Lys-Ser-Tyr-Ser-Met-Glu-His-Phe-(D-Arg)-Trp-Gly-Lys-Pro-(D-Val)
Ac-(Ac-Lys-Gly)Lys-Lys-Ser-Tyr-Ser-Met-Glu-His-Phe-Arg-(D-Trp)-Gly-Lys-Pro-(D-Val)
Ac-(Ae-Lys-Gly)Lys-Lys-Ser-Tyr-Ser-Met-Glu-His-(D-Phe)-Arg-(D-Trp)-Gly-Lys-Pre-(D-Val)
Ac-(Ac-Lys-Gly)Lys-Lys-Ser-Tyr-Ser-Met-Glu-His-Nal-Arg-Trp-Gly-Lys-Pro
Ac-(Ac-Lys-Gly)Lys-Lys-Ser-Tyr-Ser-Met-Glu-His-(D-Nal)-Arg-Trp-Gly-Lys-Pre-(D-Val)
Ac-(Ac-Lys-Gly)Lys-Lys-Ser-Tyr-Ser-Nle-Glu-His-Phe-Arg-Trp-Gly-Lys-Pro-Val (Ac-(Ac-Lys-Gly)Lys-Lys-SEQ ID NO: 3)
Ac-(Ac-Lys-Gly)Lys-Lys-Ser-Tyr-Ser-Nle-Glu-His-(D-Phe)-Arg-Trp-Gly-Lys-Pro-Val
Ac-(Ac-Lys-Gly)Lys-Lys-Ser-Tyr-Ser-Nle-Glu-His-Phe-(D-Arg)-Trp-Gly-Lys-Pro-Val
Ac-(Ac-Lys-Gly)Lys-Lys-Ser-Tyr-Ser-Nle-Glu-His-Phe-Arg-(D-Trp)-Gly-Lys-Pro-Val
Ac-(Ac-Lys-Gly)Lys-Lys-Ser-Tyr-Ser-Nle-Glu-His-(D-Phe)-Arg-(D-Trp)-Gly-Lys-Pro-Val
Ac-(Ac-Lys-Gly)Lys-Lys-Ser-Tyr-Ser-Nle-Glu-His-Nal-Arg-Trp-Gly-Lys-Pro-Val
Ac-(Ac-Lys-Gly)Lys-Lys-Ser-Tyr-Ser-Nle-Glu-His-(D-Nal)-Arg-Trp-Gly-Lys-Pro-Val
Ac-(Ac-Lys-Gly)Lys-Lys-Ser-Tyr-Ser-Nle-Glu-His-Phe-Arg-Trp-Gly-Lys-Pro-(D-Val)
Ac-(Ac-Lys-GlY)Lys-Lys-Ser-Tyr-Ser-Nle-Glu-His-(D-Phe)-Arg-Trp-Gly-Lys-Pro-(D-Val)
Ac-(Ac-Lys-Gly)Lys-Lys-Ser-Tyr-Ser-Nle-Glu-His-Phe-(D-Arg)-Trp-Gly-Lys-Pro-(D-Val)
Ac-(Ac-Lys-Gly)Lys-Lys-Ser-Tyr-Ser-Nle-Glu-His-Phe-Arg-(D-Trp)-Gly-Lys-Pro-(D-Val)
Ac-(Ac-Lys-Gly)Lys-Lys-Ser-Tyr-Ser-Nle-Glu-His-(D-Phe)-Arg-(D-Trp)-Gly-Lys-Pro-(D-Val)

APPENDIX-continued

Examples of sequences of MSH analogues

Ac-(Ac-Lys-Gly)Lys-Lys-Ser-Tyr-Ser-Nle-Glu-His-Nal-Arg-Trp-Gly-Lys-Pro-(D-Val)
Ac-(Ac-Lys-Gly)Lys-Lys-Ser-Tyr-Ser-Nle-Glu-His-(D-Nal)-Arg-Trp-Gly-Lys-Pro-(D-Val)
Ac-(Ac-Lys-Gly)Lys-Lys-Ser-Ser-Ile-Ile-Ser-His-Phe-Arg-Trp-Gly-Lys-Pro-Val (Ac-(Ac-Lys-Gly)Lys-Lys-SEQ ID NO: 5)
Ac-(Ac-Lys-Gly)Lys-Lys-Ser-Ser-Ile-Ile-Ser-His-(D-Phe)-Arg-Trp-Gly-Lys-Pro-Val
Ac-(Ac-Lys-Gly)Lys-Lys-Ser-Ser-Ile-Ile-Ser-His-Phe-(D-Arg)-Trp-Gly-Lys-Pro-Val
Ac-(Ac-Lys-Gly)Lys-Lys-Ser-Ser-Ile-Ile-Ser-His-Phe-Arg-(D-Trp)-Gly-Lys-Pro-Val
Ac-(Ac-Lys-Gly)Lys-Lys-Ser-Ser-Ile-Ile-Ser-His-(D-Phe)-Arg-(D-Trp)-Gly-Lys-Pro-Val
Ac-(Ac-Lys-Gly)Lys-Lys-Ser-Ser-Ile-Ile-Ser-His-Nal-Arg-Trp-Gly-Lys-Pro-Val
Ac-(Ac-Lys-Gly)Lys-Lys-Ser-Ser-Ile-Ile-Ser-His-(D-Nal)-Arg-Trp-Gly-Lys-Pro-Val
Ac-(Ac-Lys-Gly)Lys-Lys-Ser-Ser-Ile-Ile-Ser-His-Phe-Arg-Trp-Gly-Lys-Pro-(D-Val)
Ac-(Ac-Lys-Gly)Lys-Lys-Ser-Ser-Ile-Ile-Ser-His-(D-Phe)-Arg-Trp-Gly-Lys-Pro-(D-Val)
Ac-(Ac-Lys-Gly)Lys-Lys-Ser-Ser-Ile-Ile-Ser-His-Phes(D-Arg)-Trp-Gly-Lys-Pro-(D-Val)
Ac-(Ac-Lys-Gly)Lys-Lys-Ser-Ser-Ile-Ile-Ser-His-Phe-Arg-(D-Trp)-Gly-Lys-Pro-(D-Val)
Ac-(Ac-Lys-Gly)Lys-Lys-Ser-Ser-Ile-Ile-Ser-His-(D-Phe)-Arg-(D-Trp)-Gly-Lys-Pro-(D-Val)
Ac-(Ac-Lys-Gly)Lys-Lys-Ser-Ser-Ile-Ile-Ser-His-Nal-Arg-Trp-Gly-Lys-Pro-(D-Val)
Ac-(Ac-Lys-Gly)Lys-Lys-Ser-Ser-Ile-Ile-Ser-His-(D-Nal)-Arg-Trp-Gly-Lys-Pro-(D-Val)
The C-terminal Valine may be amidated (NH$_2$).

X = Ac-Lys-(Ac-Lys-Gly)Lys-:
Ac-Lys-(Ac-Lys-Gly)Lys-Ser-Tyr-Ser-Met-Glu-His-Phe-Arg-Trp-Gly-Lys-Pro-Val (Ac-Lys-(Ac-Lys-Gly)Lys-SEQ ID NO: 1)
Ac-Lys-(Ac-Lys-Gly)Lys-Ser-Tyr-Ser-Met-Glu-His-(D-Phe)-Arg-Trp-Gly-Lys-Pro-Val
Ac-Lys-(Ac-Lys-Gly)Lys-Ser-Tyr-Ser-Met-Glu-His-Phe-(D-Arg)-Trp-Gly-Lys-Pro-Val
Ac-Lys-(Ac-Lys-Gly)Lys-Ser-Tyr-Ser-Met-Glu-His-Phe-Arg-(D-Trp)-Gly-Lys-Pro-Val
Ac-Lys-(Ac-Lys-Gly)Lys-Ser-Tyr-Ser-Met-Glu-His-(D-Phe)-Arg-(D-Trp)-Gly-Lys-Pro-Val
Ac-Lys-(Ac-Lys-Gly)Lys-Ser-Tyr-Ser-Met-Glu-His-Nal-Arg-Trp-Gly-Lys-Pro-Val
Ac-Lys-(Ac-Lys-Gly)Lys-Ser-Tyr-Ser-Met-Glu-His-(D-Nah-Arg-Trp-Gy-Lys-Pro-Val
Ac-Lys-(Ac-Lys-Gly)Lys-Ser-Tyr-Ser-Met-Glu-His-Phe-Arg-Trp-Gly-Lys-Pro-(D-Val)
Ac-Lys-(Ac-Lys-Gly)Lys-Ser-Tyr-Ser-Met-Glu-His-(D-Phe)-Arg-Trp-Gly-Lys-Pro-(D-Val)
Ac-Lys-(Ac-Lys-Gly)Lys-Ser-Tyr-Ser-Met-Glu-His-Phe-(D-Arg)-Trp-Gly-Lys-Pro-(D-Val)
Ac-Lys-(Ac-Lys-Gly)Lys-Ser-Tyr-Ser-Met-Glu-His-Phe-Arg-(D-Trp)-Gly-Lys-Pro-(D-Val)
Ac-Lys-(Ac-Lys-GIy)Lys-Ser-Tyr-Ser-Met-Glu-His-(D-Phe)-Arg-(D-Trp)-Gly-Lys-Pro-(D-Val)
Ac-Lys-(Ac-Lys-Gly)Lys-Ser-Tyr-Ser-Met-Glu-His-Nal-Arg-Trp-Gly-Lys-Pro-(D-Val)
Ac-Lys-(Ac-Lys-Gly)Lys-Ser-Tyr-Ser-Met-Glu-His-(D-Nal)-Arg-Trp-Gly-Lys-Pro-(D-Val)
Ac-Lys-(Ac-Lys-Gly)Lys-Ser-Tyr-Ser-Nle-Glu-His-Phe-Arg-Trp-Gly-Lys-Pro-Val (Ac-Lys-(Ac-Lys-Gly)Lys-SEQ ID NO: 3)
Ae-Lys-(Ac-Lys-Gly)Lys-Ser-Tyr-Ser-Nle-Glu-His-(D-Phe)-Arg-Trp-Gly-Lys-Pro-Val
Ac-Lys-(Ac-Lys-Gly)Lys-Ser-Tyr-Ser-NIe-Glu-His-Phe-(D-Arg)-Trp-Gly-Lys-Pro-Val
Ac-Lys-(Ac-Lys-Gly)Lys-Ser-Tyr-Ser-Nle-Glu-His-Phe-Ng-(D-Trp)-Gly-Lys-Pro-Val
Ac-Lys-(Ac-Lys-Gly)Lys-Ser-Tyr-Ser-Nle-Glu-His-(D-Phe)-Arg-(D-Trp)-Gly-Lys-Pro-Val
Ac-Lys-(Ac-Lys-Gly)Lys-Ser-Tyr-Ser-Nle-Glu-His-Nal-Arg-Trp-Gly-Lys-Pro-Val
Ac-Lys-(Ac-Lys-Gly)Lys-Ser-Tyr-Ser-Nie-Glu-His-(D-Nal)-Arg-Trp-Gly-Lys-Pro-Val
Ac-Lys-(Ac-Lys-Gly)Lys-Ser-Tyr-Ser-Nle-Glu-His-Phe-Arg-Trp-Gly-Lys-Pro-(D-Val)
Ac-Lys-(Ac-Lys-Gly)Lys-Ser-Tyr-Ser-Nle-Glu-His-(D-Phe)-Arg-Trp-Gly-Lys-Pro-(D-Val)
Ac-Lys-(Ac-Lys-Gly)Lys-Ser-Tyr-Ser-Nle-Glu-His-Phe-(D-Arg)-Trp-Gly-Lys-Pro-(D-Val)
Ac-Lys-(Ac-Lys-Gly)Lys-Ser-Tyr-Ser-Nle-Glu-His-Phe-Arg-(D-Trp)-Gly-Lys-Pro-(D-Val)
Ac-Lys-(Ac-Lys-Gly)Lys-Ser-Tyr-Ser-Nle-Glu-His-(D-Phe)-Arg-(D-Trp)-Gly-Lys-Pro-(D-Val)
Ac-Lys-(Ac-Lys-Gly)Lys-Ser-Tyr-Ser-Nle-Glu-His-Nal-Arg-Trp-Gly-Lys-Pro-(D-Val)
Ac-Lys-(Ac-Lys-Gly)Lys-Ser-Tyr-Ser-Nle-Glu-His-(D-Nal)-Arg-Trp-Gly-Lys-Pro-(D-Val)
Ac-Lys-(Ac-Lys-Gly)Lys-Ser-Ser-Ile-Ile-Ser-His-Phe-Arg-Trp-Gly-Lys-Pro-Val (Ac-Lys-(Ac-Lys-Gly)Lys-SEQ ID NO: 5)
Ac-Lys-(Ac-Lys-Gly)Lys-Ser-Ser-Ile-Ile-Ser-His-(D-Phe)-Arg-Trp-Gly-Lys-Pro-Val
Ac-Lys-(Ac-Lys-Gly)Lys-Ser-Ser-Ile-Ile-Ser-His-Phe-(D-Arg)-Trp-Gly-Lys-Pro-Val
Ac-Lys-(Ac-Lys-Gly)Lys-Ser-Ser-Ile-Ile-Ser-His-Phe-Arg-(D-Trp)-Gly-Lys-Pro-Val
Ac-Lys-(Ac-Lys-Gly)Lys-Ser-Ser-Ile-Ile-Ser-His-(D-Phe)-Arg-(D-Trp)-Gly-Lys-Pro-Val
Ac-Lys-(Ac-Lys-Gly)Lys-Ser-Ser-Ile-Ile-Ser-His-Nal-Arg-Trp-Gly-Lys-Pro-Val
Ac-Lys-(Ac-Lys-Gly)Lys-Ser-Ser-Ile-Ile-Ser-His-(D-Na)-Arg-Trp-Gly-Lys-Pro-Val
Ac-Lys-(Ac-Lys-Gly)Lys-Ser-Ser-Ile-Ile-Ser-His-Phe-Arg-Trp-Gly-Lys-Pro-(D-Val)
Ac-Lys-(Ac-Lys-Gly)Lys-Ser-Ser-Ile-Ile-Ser-His-(D-Phe)-Arg-Tre-Gly-Lys-Pro-(D-Val)
Ac-Lys-(Ac-Lys-Gly)Lys-Ser-Ser-Ile-Ile-Ser-His-Phe-(D-Arg)-Trp-Gly-Lys-Pro-(D-Val)
Ac-Lys-(Ac-Lys-Gly)Lys-Ser-Ser-Ile-Ile-Ser-His-Phe-Arg-(D-Trp)-Gly-Lys-Pro-(D-Val)
Ac-Lys-(Ac-Lys-Gly)Lys-Ser-Ser-Ile-Ile-Ser-His-(D-Phe)-Arg-(D-Trp)-Gly-Lys-Pro-(D-Val)
Ac-Lys-(Ac-Lys-Gly)Lys-Ser-Ser-Ile-Ile-Ser-His-Nal-Arg-Trp-Gly-Lys-Pro-(D-Val)
Ac-Lys-(Ac-Lys-Gly)Lys-Ser-Ser-Ile-Ile-Ser-Hs-(D-Nal)-Arg-Trp-Gly-Lys-Pro-(D-Val)
The C-terminal Valine may be amidated (NH$_2$).

X = Ac-(Ac-Lys-Lys)Lys-:
Ac-(Ac-Lys-Lys)Lys-Tyr-Val-Met-Gly-His-Phe-Arg-Trp-Asp-Arg-Phe-[Gly](Ac-(Ac-Lys-Lys)Lys-SEQ ID NO:s 11 or 7)
Ac-(Ac-Lys-Lys)Lys-Tyr-Val-Met-Gly-His-(D-Phe)-Arg-Trp-Asp-Arg-Phe-[Gly]
Ac-(Ac-Lys-Lys)Lys-Tyr-Val-Met-Gly-His-Phe-(D-Arg)-Trp-Asp-Arg-Phe-[Gly]
Ac-(Ac-Lys-Lys)Lys-Tyr-Val-Met-Gly-His-Phe-Arg-(D-Trp)-Asp-Arg-Phe-[Gly]
Ac-(Ac-Lys-Lys)Lys-Tyr-Val-Met-Gly-His-(D-Phe)-Arg-(D-Trp)-Asp-Arg-Phe-[Gly]

APPENDIX-continued

Examples of sequences of MSH analogues

Ac-(Ac-Lys-Lys)Lys-Tyr-Val-Met-Gly-His-Nal-Arg-Trp-Asp-Arg-Phe-[Gly]
Ac-(Ac-Lys-Lys)Lys-Tyr-Val-Met-Gly-His-(D-Nal)-Arg-Trp-Asp-Arg-Phe-[Gly]
Ac-(Ac-Lys-Lys)Lys-Tyr-Val-Met-Gly-His-Phe-Arg-Trp-Asp-Arg-(D-Phe)-[Gly]
Ac-(Ac-Lys-Lys)Lys-Tyr-Val-Met-Gly-His-(D-Phe)-Arg-Trp-Asp-Arg-(D-Phe)-[Gly]
Ac-(Ac-Lys-Lys)Lys-Tyr-Val-Met-Gly-His-Phe-(D-Arg)-Trp-Asp-Arg-(D-Phe)-[Gly]
Ac-(Ac-Lys-Lys)Lys-Tyr-Val-Met-Gly-His-Phe-Arg-(D-Trp)-Asp-Arg-(D-Phe)-[Gly]
Ac-(Ac-Lys-Lys)Lys-Tyr-Val-Met-Gly-His-(D-Phe)-Arg-(D-Trp)-Asp-Arg-(D-Phe)-[Gly]
Ac-(Ac-Lys-Lys)Lys-Tyr-Val-Met-Gly-His-Nal-Arg-Trp-Asp-Arg-(D-Phe)-[Gly]
Ac-(Ac-Lys-Lys)Lys-Tyr-Val-Met-Gly-His-(D-Nal)-Arg-Trp-Asp-Arg-(D-Phe)-[Gly]
Ac-(Ac-Lys-Lys)Lys-Tyr-Val-Nle-Gly-His-Phe-Arg-Trp-Asp-Arg-Phe-[Gly] (Ac-(Ac-Lys-Lys)Lys-SEQ ID NOs 13 or 9)
Ac-(Ac-Lys-Lys)Lys-Tyr-Val-Nle-Gly-His-(D-Phe)-Arg-Trp-Asp-Arg-Phe-[Gly]
Ac-(Ac-Lys-Lys)Lys-Tyr-Val-Nle-Gly-His-Phe-(D-Arg)-Trp-Asp-Arg-Phe-[Gly]
Ac-(Ac-Lys-Lys)Lys-Tyr-Val-Nle-Gly-His-Phe-Arg-(D-Trp)-Asp-Arg-Phe-[Gly]
Ac-(Ac-Lys-Lys)Lys-Tyr-Val-Nle-Gly-His-(D-Phe)-Arg-(D-Trp)-Asp-Arg-Phe-[Gly]
Ac-(Ac-Lys-Lys)Lys-Tyr-Val-Nle-Gly-His-Nal-Arg-Trp-Asp-Arg-Phe-[Gly]
Ac-(Ac-Lys-Lys)Lys-Tyr-Val-Nle-Gly-His-(D-Nal)-Arg-Trp-Asp-Arg-Phe-[Gly]
Ac-(Ac-Lys-Lys)Lys-Tyr-Val-Nle-Gly-His-Phe-Arg-Trp-Asp-Arg-(D-Phe)-[Gly]
Ac-(Ac-Lys-Lys)Lys-Tyr-Val-Nle-Gly-His-(D-Phe)-Arg-Trp-Asp-Arg-(D-Phe)-[Gly]
Ac-(Ac-Lys-Lys)Lys-Tyr-Val-Nle-Gly-His-Phe-(D-Arg)-Trp-Asp-Arg-(D-Phe)-[Gly]
Ac-(Ac-Lys-Lys)Lys-Tyr-Val-Nle-Gly-His-Phe-Arg-(D-TrP)-AsP-Arg-(D-Phe)-[Gly]
Ac-(Ac-Lys-Lys)Lys-Tyr-Val-Nle-Gly-His-(D-Phe)-Arg-(D-Trp)-Asp-Arg-(D-Phe)-(Gly]
Ac-(Ac-Lys-Lys)Lys-Tyr-Val-Nle-Gly-His-Nal-Arg-Trp-Asp-Arg-(D-Phe)-[Gly]
Ac-(Ac-Lys-Lys)Lys-Tyr-Val-Nle-Gly-His-(D-Nal)-Arg-Trp-Asp-Arg-(D-Phe)-[Gly]
[Gly] is an optional amino acid in the sequence (may be present or absent)
The C-terminal Phe or Gly may be amidated (NH$_2$).

X = Ac-(Ac-Lys-Lys-Lys)Lys-:
(Ac-Lys-Lys-Lys)Lys-Tyr-Val-Met-Gly-His-Phe-Arg-Trp-Asp-Arg-Phe-[Gly] (Ac-(Ac-Lys-Lys-Lys)Lys-SEQ ID NO:s 11 or 7)
Ac-(Ac-Lys-Lys-Lys)Lys-Tyr-Val-Met-Gly-His-(D-Phe)-Arg-Trp-Asp-Arg-Phe-[Gly]
Ac-(Ac-Lys-Lys-Lys)Lys-Tyr-Val-Met-Gly-His-Phe-(D-Arg)-Trp-Asp-Arg-Phe-[Gly]
Ac-(Ac-Lys-Lys-Lys)Lys-Tyr-Val-Met-Gly-His-Phe-Arg-(D-Trp)-Asp-Arg-Phe-[Gly]
Ac-(Ac-Lys-Lys-Lys)Lys-Tyr-Val-Met-Gly-His-(D-Phe)-Arg-(D-Trp)-Asp-Arg-Phe-[Gly]
Ac-(Ac-Lys-Lys-Lys)Lys-Tyr-Val-Met-Gly-His-Nal-Arg-Trp-Asp-Arg-Phe-[Gly]
Ac-(Ac-Lys-Lys-Lys)Lys-Tyr-Val-Met-Gly-His-(D-Nal)-Arg-Trp-Asp-Arg-Phe-[Gly]
Ac-(Ac-Lys-Lys-Lys)Lys-Tyr-Val-Met-Gly-His-Phe-Arg-Trp-Asp-Arg-(D-Phe)-[Gly]
Ac-(Ac-Lys-Lys-Lys)Lys-Tyr-Val-Met-Gly-His-(D-Phe)-Arg-Trp-Asp-Arg-(D-Phe)-[Gly]
Ac-(Ac-Lys-Lys-Lys)Lys-Tyr-Val-Met-Gly-His-Phe-(D-Arg)-Trp-Asp-Arg-(D-Phe)-[Gly]
Ac-(Ac-Lys-Lys-Lys)Lys-Tyr-Val-Met-Gly-His-Phe-Arg-(D-Tip)-Asp-Arg-(D-Phe)-[Gly]
Ac-(Ac-Lys-Lys-Lys)Lys-Tyr-Val-Met-Gly-His-(D-Phe)-Arg-(D-Trp)-Asp-Arg-(D-Phe)-[Gly]
Ac-(Ac-Lys-Lys-Lys)Lys-Tyr-Val-Met-Gly-His-Nal-Arg-Trp-Asp-Arg-(D-Phe)-[Gly]
Ac-(Ac-Lys-Lys-Lys)Lys-Tyr-Val-Met-Gly-His-(D-Nal)-Arg-Trp-Asp-Arg-(D-Phe)-[Gly]
Ac-(Ac-Lys-Lys-Lys)Lys-Tyr-Val-Nle-Gly-His-Phe-Arg-Trp-Asp-Arg-Phe-[Gly] (Ac-(Ac-Lys-Lys-Lys)Lys-SEQ ID NO:s 13 or 9)
Ac-(Ac-Lys-Lys-Lys)Lys-Tyr-Val-Nle-Gly-His-(D-Phe)-Arg-Trp-Asp-Arg-Phe-[Gly]
Ac-(Ac-Lys-Lys-Lys)Lys-Tyr-Val-Nle-Gly-His-Phe-(D-Arg)-Trp-Asp-Arg-Phe-[Gly]
Ac-(Ac-Lys-Lys-Lys)Lys-Tyr-Val-Nle-Gly-His-Phe-Arg-(D-Trp)-Asp-Arg-Phe-[Gly]
Ac-(Ac-Lys-Lys-Lys)Lys-Tyr-Val-Nle-Gly-His-(D-Phe)-Arg-(D-Trp)-Asp-Arg-Phe-[Gly]
Ac-(Ac-Lys-Lys-Lys)Lys-Tyr-Val-Nle-Gly-His-Nal-Arg-Trp-Asp-Arg-Phe-[Gly]
Ac-(Ac-Lys-Lys-Lys)Lys-Tyr-Val-Nle-Gly-His-(D-Nal)-Arg-Trp-Asp-Arg-Phe-[Gly]
Ac-(Ac-Lys-Lys-Lys)Lys-Tyr-Val-Nle-Gly-His-Phe-Arg-Trp-Asp-Arg-(D-Phe)-[Gly]
Ac-(Ac-Lys-Lys-Lys)Lys-Tyr-Val-Nle-Gly-His-(D-Phe)-Arg-Trp-Asp-Arg-(D-Phe)-[Gly]
Ac-(Ac-Lys-Lys-Lys)Lys-Tyr-Val-Nle-Gly-His-Phe-(D-Arg)-Trp-Asp-Arg-(D-Phe)-[Gly]
Ac-(Ac-Lys-Lys-Lys)Lys-Tyr-Val-Nle-Gly-His-Phe-Arg-(D-Trp)-Asp-Arg-(D-Phe)-[Gly]
Ac-(Ac-Lys-Lys-Lys)Lys-Tyr-Val-Nle-Gly-His-(D-Phe)-Arg-(D-Trp)-Asp-Arg-(D-Phe)-[Gly]
Ac-(Ac-Lys-Lys-Lys)Lys-Tyr-Val-Nle-Gly-His-Nal-Arg-Trp-Asp-Arg-(D-Phe)-[Gly]
Ac-(Ac-Lys-Lys-Lys)Lys-Tyr-Val-Nle-Gly-His-(D-Nal)-Arg-Trp-Asp-Arg-(D-Phe)-[Gly]
[Gly] is an optional amino acid in the sequence (may he present or absent)
The C-terminal Phe or Gly may be amidated (NH$_2$).

X = Ac-(Ac-Lys-Gly-Lys)Lys-:
Ac-(Ac-Lys-Gly-Lys)Lys-Tyr-Val-Met-Gly-His-Phe-Arg-Trp-Asp-Arg-Phe-[Gly] (Ac-(Ac-Lys-Gly-Lys)Lys-SEQ ID NO 11 or 7)
Ac-(Ac-Lys-Gly-Lys)Lys-Tyr-Val-Met-Gly-His-(D-Phe)-Arg-Trp-Asp-Arg-Phe-[Gly]
Ac-(Ae-Lys-Gly-Lys)Lys-Tyr-Val-Met-Gly-His-Phe-(D-Arg)-Trp-Asp-Arg-Phe-[Gly]
Ac-(Ac-Lys-Gly-Lys)Lys-Tyr-Val-Met-Gly-His-Phe-Arg-(D-Trp)-Asg-Arg-Phe-[Gly]
Ac-(Ac-Lys-Gly-Lys)Lys-Tyr-Val-Met-Gly-His-(D-Phe)-Arg-(D-Trp)-Asp-Arg-Phe-[Gly]
Ac-(Ac-Lys-Gly-Lys)Lys-Tyr-Val-Met-Gly-His-Nal-Arg-Trp-Trp-Arg-Phe-[Gly]
Ac-(Ac-Lys-Gly-Lys)Lys-Tyr-Val-Met-Gly-His-(D-Nal)-Arg-Trp-Asg-Arg-Phe-[Gly]
Ac-(Ac-Lys-Gly-Lys)Lys-Tyr-Val-Met-Gly-His-Phe-Arg-Trp-Asp-Arg-(D-Phe)-[Gly]
Ac-(Ac-Lys-Gly-Lys)Lys-Tyr-Val-Met-Gly-His-(D-Phe)-Arg-Trp-Asp-Arg-(D-Phe)-[Gly]
Ac-(Ac-Lys-Gly-Lys)Lys-Tyr-Val-Met-Gly-His-Phe-(D-Arg)-Trp-Asp-Arg-(D-Phe)-[Gly]
Ac-(Ac-Lys-Gly-Lys)Lys-Tyr-Val-Met-Gly-His-Phe-Arg-(D-Trg)-Asp-Arg-(D-Phe)-[Gly]
Ac-(Ac-Lys-Gly-Lys)Lys-Tyr-Val-Met-Gly-His-(D-Phe)-Arg-(D-Trp)-Asp-Arg-(D-Phe)-[Gly]

APPENDIX-continued

Examples of sequences of MSH analogues

Ac-(Ac-Lys-Gly-Lys)Lys-Tyr-Val-Met-Gly-His-Nal-Arg-Trp-Asp-Arg-(D-Phe)-[Gly]
Ac-(Ac-Lys-Gly-Lys)Lys-Tyr-Val-Met-Gly-His-(D-Nal)-Arg-Trp-Asp-Arg-(D-Phe)-[Gly]
Ac-(Ac-Lys-Gly-Lys)Lys-Tyr-Val-Nle-Gly-His-Phe-Arg-Trg-Asp-Arg-Phe-[Gly] (Ac-(Ac-Lys-Gly-Lys)Lys-SEQ ID NO:s 13 or 9)
Ac-(Ac-Lys-Gly-Lys)Lys-Tyr-Val-Nle-Gly-His-(D-Phe)-Arg-Trp-Asp-Arg-Phe-[Gly]
Ac-(Ac-Lys-Gly-Lys)Lys-Tyr-Val-Nle-Gly-His-Phe-(D-Arg)-Trp-Asp-Arg-Phe-[Gly]
Ac-(Ac-Lys-Gly-Lys)Lys-Tyr-Val-Nle-Gly-His-Phe-Arg-(D-Trp)-Asp-Arg-Phe-[Gly]
Ac-(Ac-Lys-Gly-Lys)Lys-Tyr-Val-Nle-Gly-His-(D-Phe)-Arg-(D-Trp)-Asp-Arg-Phe-[Gly]
Ac-(Ac-Lys-Gly-Lys)Lys-Tyr-Val-Nle-Gly-His-Nal-Arg-Trp-Asp-Arg-Phe-[Gly]
Ac-(Ac-Lys-Gly-Lys)Lys-Tyr-Val-Nle-Gly-His-(D-Nal)-Arg-Trp-Asp-Arg-Phe-[Gly]
Ac-(Ac-Lys-Gly-Lys)Lys-Tyr-Val-Nle-Gly-His-Phe-Arg-Trp-Asp-Arg-(D-Phe)-[Gly]
Ac-(Ac-Lys-Gly-Lys)Lys-Tyr-Val-Nle-Gly-His-(D-Phe)-Arg-Trp-Asg-Arg-(D-Phe)-[Gly]
Ac-(Ac-Lys-Gly-Lys)Lys-Tyr-Val-Nle-Gly-His-Phe-(D-Arg)-Trg-Asp-Arg-(D-Phe)-[Gly]
Ac-(Ac-Lys-Gly-Lys)Lys-Tyr-Val-Nle-Gly-His-Phe-Arg-(D-Trp)-Asp-Arg-(D-Phe)-[Gly]
Ac-(Ac-Lys-Gly-Lys)Lys-Tyr-Val-Nle-Gly-His-(D-Phe)-Arg-(D-Trp)-Asp-Arg-(D-Phe)-[Gly]
Ac-(Ac-Lys-Gly-Lys)Lys-Tyr-Val-Nle-Gly-His-Nal-Arg-Trp-Asp-Arg-(D-Phe)-[Gly]
Ac-(Ac-Lys-Gly-Lys)Lys-Tyr-Val-Nle-Gly-His-(D-Nal)-Arg-Trg-Asp-Arg-(D-Phe)-[Gly]
[Gly] is an optional amino acid in the sequence (may be present or absent)
The C-terminal Phe or Gly may be amidated (NH$_2$).

X = Ac-(Ac-Lys-Lys-Gly-)Lys-:
Ac-(Ac-Lys-Lys-Gly-)Lys-Tyr-Val-Met-Gly-His-Phe-Arg-Trp-Asp-Arg-Phe-[Gly] (Ac-(Ac-Lys-Lys-Gly-)Lys-SEQ ID NO:s 11 or 7)
Ac-(Ac-Lys-LyS-Gly-)Lys-Tyr-Val-Met-Gly-His-(D-Phe)-Arg-Trp-Asg-Arg-Phe-[Gly]
Ac-(Ac-Lys-Lys-Gly-)Lys-Tyr-Val-Met-Gly-His-Phe-(D-Arg)-Trp-Asp-Arg-Phe-[Gly]
Ac-(Ac-Lys-Lys-Gly-)Lys-Tyr-Val-Met-Gly-His-Phe-Arg-(D-Trp)-Asp-Arg-Phe-[Gly]
Ac-(Ar-Lys-Lys-Gly-)Lys-Tyr-Val-Met-Gly-His-(D-Phe)-Arg-(D-Trp)-Asp-Arg-Phe-[Gly]
Ac-(Ac-Lys-Lys-Gly-)Lys-Tyr-Val-Met-Gly-His-Nal-Arg-Trp-Asp-Arg-Phe-[Gly]
Ac-(Ac-Lys-Lys-Gly-)Lys-Tyr-Val-Met-Gly-His-(D-Nal)-Arg-Trp-Asp-Arg-Phe-[Gly]
Ac-(Ao-Lys-Lys-Gly-)Lys-Tyr-Val-Met-Gly-His-Phe-Arg-Trp-Asg-Arg-(D-Phe)-[Gly]
Ac-(Ac-Lys-Lys-Gly-)Lys-Tyr-Val-Met-Gly-His-(D-Phe)-Arg-Trp-Asp-Arg-(D-Phe)-[Gly]
Ac-(Ac-Lys-Lys-Gly-)Lys-Tyr-Val-Met-Gly-His-Phe-(D-Arg)-Trp-Asp-Arg-(D-Phe)-[Gly]
Ac-(Ac-Lys-Lys-Gly-)Lys-Tyr-Val-Met-Gly-His-Phe-Arg-(D-Trp)-Asp-Arg-(D-Phe)-[Gly]
Ac-(Ac-Lys-Lys-Gly-)Lys-Tyr-Val-Met-Gly-His-(D-Phe)-Arg-(D-Trp)-Asp-Arg-(D-Phe)-[Gly]
Ac-(Ac-Lys-Lys-Gly-)Lys-Tyr-Val-Met-Gly-His-Nal-Arg-Trp-Asp-Arg-(D-Phe)-[Gly]
Ac-(Ac-Lys-Lys-Gly-)Lys-Tyr-Val-Met-Gly-His-(D-Nal)-Arg-Trp-Asp-Arg-(D-Phe)-[Gly]
Ac-(Ac-Lys-Lys-Gly-)Lys-Tyr-Val-Nle-Gly-His-Phe-Arg-Trp-Asp-Arg-Phe-[Gly] (Ac-(Ac-Lys-Lys-Gly-)Lys-SEQ ID NO:s 13 or 9)
Ac-(Ac-Lys-Lys-Gly-)Lys-Tyr-Val-Nle-Gly-His-(D-Phe)-Arg-Trp-Asp-Arg-Phe-[Gly]
Ac-(Ac-Lys-Lys-Gly-)Lys-Tyr-Val-Nle-Gly-His-Phe-(D-Arg)-Trp-Asp-Arg-Phe-[Gly]
Ac-(Ac-Lys-Lys-Gly-)Lys-Tyr-Val-Nle-Gly-His-Phe-Arg-(D-Trp)-Asp-Arg-Phe-[Gly]
Ac-(Ac-Lys-Lys-Gly-)Lys-Tyr-Val-Nle-Gly-His-(D-Phe)-Arg-(D-Trp)Asp-Arg-Phe-[Gly]
Ac-(Ac-Lys-Lys-Gly-)Lys-Tyr-Val-Nle-Gly-His-Nal-Arg-Trp-Asp-Arg-Phe-[Gly]
Ac-(Ac-Lys-Lys-Gly-)Lys-Tyr-Val-Nle-Gly-His-(D-Nal)-Arg-Trp-Asp-Arg-Phe-[Gly]
Ac-(Ac-Lys-Lys-Gly-)Lys-Tyr-Val-Nle-Gly-His-Phe-Arg-Trp-Asp-Arg-(D-Phe)-[Gly]
Ac-(Ac-Lys-Lys-Gly-)Lys-Tyr-Val-Nle-Gly-His-(D-Phe)-Aro-Trp-Asp-Arg-(D-Phe)-[Gly]
Ac-(Ac-Lys-Lys-Gly-)Lys-Tyr-Val-Nle-Gly-His-Phe-(D-Arg)-Trp-Asp-Arg-(D-Phe)-[Gly]
Ac-(Ac-Lys-Lys-Gly-)Lys-Tyr-Val-Nle-Gly-His-Phe-Arg-(D-Trp)-Asp-Arg-(D-Phe)-[Gly]
Ac-(Ac-Lys-Lys-Gly-)Lys-Tyr-Val-Nle-Giy-His-(D-Phe)-Arg-(D-Trp)-Asp-Arg-(D-Phe)-[Gly]
Ac-(Ac-Lys-Lys-Gly-)Lys-Tyr-Val-Nle-Gly-His-Nal-Arg-Trp,Asp-Arg-(D-Phe)-[Gly]
Ac-(Ac-Lys-Lys-Gly-)Lys-Tyr-Val-Nle-Gly-His-(D-Nal)-Arg-Trp-Asp-Arg-(D-Phe)-[Gly]
[Gly] is an optional amino acid in the sequence (may be present or absent)
The C-terminal Phe or Gly may be amidated (NH$_2$).

X = Ac-(Ac-Lys)Lys-Lys-:
Ac-(Ac-Lys-)Lys-Lys-Tyr-Val-Met-Gly-His-Phe-Arg-Trp-Asp-Arg-Phe-[Gly] (Ac-(Ac-Lys)Lys-Lys-SEQ ID NO:s 13 or 9)
Ac-(Ac-Lys-)Lys-Lys-Tyr-Val-Met-Gly-His-(D-Phe)-Arg-Trp-Asp-Arg-Phe-[Gly]
Ac-(Ac-Lys-)Lys-Lys-Tyr-Val-Met-Gly-His-Phe-(D-Arg)-Trp-Asp-Arg-Phe-[Gly]
Ac-(Ac-Lys-)Lys-Lys-Tyr-Val-Met-Gly-His-Phe-Arg-(D-Trp)-Asp-Arg-Phe-[Gly]
Ac-(Ac-Lys-)Lys-Lys-Tyr-Val-Met-Gly-His-(D-Phe)-Arg-(D-Trp)-Asp-Arg-Phe-[Gly]
Ac-(Ac-Lys-)Lys-Lys-Tyr-Val-Met-Gly-His-Nal-Arg-Trp-Asp-Arg-Phe-[Gly]
Ac-(Ac-Lys-)Lys-Lys-Tyr-Val-Met-Gly-His-(D-Nal)-Arg-Trp-Asp-Arg-Phe-[Gly]
Ac-(Ac-Lys-)Lys-Lys-Tyr-Val-Met-Gly-His-Phe-Arg-Trp-Asp-Arg-(D-Phe)-[Gly]
Ac-(Ac-Lys-)Lys-Lys-Tyr-Val-Met-Gly-His-(D-Phe)-Arg-Trp-Asp-Arg-(D-Phe)-[Gly]
Ac-(Ac-Lys-)Lys-Lys-Tyr-Val-Met-Gly-His-Pbe-(D-Arg)-Trp-Asp-Arg-(D-Phe)-[Gly]
Ac-(Ac-Lys-)Lys-Lys-Tyr-Val-Met-Gly-His-Phe-Arg-(D-Trp)-Asp-Arg-(D-Phe)-[Gly]
Ac-(Ac-Lys-)Lys-Lys-Tyr-Val-Met-Gly-His-(D-Phe)-Arg-(D-Trp)-Asp-Arg-(D-Phe)-[Gly]
Ac-(Ac-Lys-)Lys-Lys-Tyr-Val-Met-Gly-His-Nal-Arg-Trp-Asp-Arg-(D-Phe)-[Gly]
Ac-(Ac-Lys-)Lys-Lys-Tyr-Val-Met-Gly-His-(D-Nal)-Arg-Trp-Asp-Arg-(D-Phe)-[Gly]
Ac-(Ac-Lys-)Lys-Lys-Tyr-Val-Nle-Gly-His-Phe-Arg-Trp-Asp-Arg-Phe-[Gly] (Ac-(Ac-Lys)Lys-Lys-SEQ ID NO:s 13 or 9)
Ac-(Ac-Lys-)Lys-Lys-Tyr-Val-Nle-Gly-His-(D-Phe)-Arg-Trp-Asp-Arg-Phe-[Gly]
Ac-(Ac-Lys-)Lys-Lys-Tyr-Val-Nle-Gly-His-Phe-(D-Arg)-Trp-Asp-Arg-Phe-[Gly]
Ac-(Ac-Lys-)Lys-Lys-Tyr-Val-Nle-Gly-His-Phe-Arg-(D-Trp)-Asp-Arg-Phe-[Gly]

APPENDIX-continued

Examples of sequences of MSH analogues

Ac-(Ac-Lys-)Lys-Lys-Tyr-Val-Nle-Gly-His-(D-Phe)-Arg-(D-Trp)-Asp-Arg-Phe-[Gly]
Ac-(Ac-Lys-)Lys-Lys-Tyr-Val-Nle-Gly-His-Nal-Arg-Trp-Asp-Arg-Phe-[Gly]
Ac-(Ac-Lys-)Lys-Lys-Tyr-Val-Nle-Gly-His-(D-Nal)-Arg-Trp-Asp-Arg-Phe-[Gly]
Ac-(Ac-Lys-)Lys-Lys-Tyr-Val-Nle-Gly-His-Phe-Arg-Trp-Asp-Arg-(D-Phe)-[Gly]
Ac-(Ac-Lys-)Lys-Lys-Tyr-Val-Nle-Gly-His-(D-Phe)-Arg-Trp-Asp-Arg-(D-Phe)-[Gly]
Ac-(Ac-Lys-)Lys-Lys-Tyr-Val-Nle-Gly-His-Phe-(D-Arg)-Trp-Asp-Arg-(D-Phe)-[Gly]
Ac-(Ac-Lys-)Lys-Lys-Tyr-Val-Nle-Gly-His-Phe-Arg-(D-Trp)-Asp-Arg-(D-Phe)-[Gly]
Ac-(Ac-Lys-)Lys-Lys-Tyr-Val-Nle-Gly-His-(D-Phe)-Arg-(D-Trp)-Asp-Arg-(D-Phe)-[Gly]
Ac-(Ac-Lys-)Lys-Lys-Tyr-Val-Nle-Gly-His-Nal-Arg-Trp-Asp-Arg-(D-Phe)-[Gly]
Ac-(Ac-Lys-)Lys-Lys-Tyr-Val-Nle-Gly-HiS-(D-Nal)-Arg-Trp-Asp-Arg-(D-Phe)-[Gly]
[Gly] is an optional amino acid in the sequence (may be present or absent)
The C-terminal Phe or Gly may be amidated (NH$_2$).

X = Ac-(Ac-Lys-Lys-)Lys-Lys-:
Ac-(Ac-Lys-Lys-)Lys-Lys-Tyr-Val-Met-Gly-His-Phe-Arg-Trp-Asp-Arg-Phe-[Gly] (Ac-(Ac-Lys-Lys-)Lys-Lys-SEO ID NO:s 11 or 7)
Ac-(Ac-Lys-Lys-)Lys-Lys-Tyr-Val-Met-Gly-His-(D-Phe)-Arg-Trp-Asp-Arg-Phe-[Gly]
Ac-(Ac-Lys-Lys-)Lys-Lys-Tyr-Val-Met-Gly-His-Phe-(D-Arg)-Trp-Asp-Arg-Phe-[Gly]
Ac-(Ac-Lys-Lys-)Lys-Lys-Tyr-Val-Met-Gly-His-Phe-Arg-(D-Trp)-Asp-Arg-Phe-[Gly]
Ac-(Ac-Lys-Lys-)Lys-Lys-Tyr-Val-Met-Gly-His-(D-Phe)-Arg-(D-Trp)-Asp-Arg-Phe-[Gly]
Ac-(Ac-Lys-Lys-)Lys-Lys-Tyr-Val-Met-Gly-His-Nal-Arg-Trp-Asp-Arg-Phe-[Gly]
Ac-(Ac-Lys-Lys-)Lys-Lys-Tyr-Val-Met-Gly-His-(D-Nal)-Arg-Trp-Asp-Arg-Phe-[Gly]
Ao-(Ac-Lys-Lys-)Lys-Lys-Tyr-Val-Met-Gly-His-Phe-Arg-Trp-Asp-Arg-(D-Phe)-[Gly]
Ao-(Ac-Lys-Lys-)Lys-Lys-Tyr-Val-Met-Gly-His-(D-Phe)-Arg-Trp-Asp-Arg-(D-Phe)-[Gly]
Ac-(Ac-Lys-Lys-)Lys-Lys-Tyr-Val-Met-Gly-His-Phe-(D-Arg)-Trp-Asp-Arg-(D-Phe)-[Gly]
Ac-(Ac-Lys-Lys-)Lys-Lys-Tyr-Val-Met-Gly-His-Phe-Arg-(D-Trp)-Asp-Arg-(D-Phe-[Gly]
Ac-(Ac-Lys-Lys-)Lys-Lys-Tyr-Val-Met-Gly-His-(D-Phe)-Arg-(D-Trp)-Asp-Arg-(D-Phe)-[Gly]
Ac-(Ac-Lys-Lys-)Lys-Lys-Tyr-Val-Met-Gly-His-Nal-Arg-Trp-Asp-Arg-(D-Phe)-[Gly]
Ac-(Ac-Lys-Lys-)Lys-Lys-Tyr-Val-Met-Gly-His-(D-Nal)-Arg-Trp-Asp-Arg-(D-Phe)-[Gly]
Ac-(Ac-Lys-Lys-)Lys-Lys-Tyr-Val-Nle-Gly-His-Phe-Arg-Trp-Asp-Arg-Phe-[Gly] (Ac-(Ac-Lys-Lys-)Lys-Lys-SEO ID NO:s 13 or 9)
Ac-(Ac-Lys-Lys-)Lys-Lys-Tyr-Val-Nle-Gly-His-(D-Phe)-Arg-Trp-Asp-Arg-Phe-[Gly]
Ac-(Ac-Lys-Lys-)Lys-Lys-Tyr-Val-Nle-Gly-His-Phe-(D-Arg)-Trp-Asp-Arg-Phe-[Gly]
Ac-(Ac-Lys-Lys-)Lys-Lys-Tyr-Val-Nle-Gly-His-Phe-Arg-(D-Trp)-Asp-Arg-Phe-[Gly]
Ac-(Ac-Lys-Lys-)Lys-Lys-Tyr-Val-Nle-Gly-His-(D-Phe)-Arg-(D-Trp)-Asp-Arg-Phe-[Gly]
Ac-(Ac-Lys-Lys-)Lys-Lys-Tyr-Val-Nle-Gly-His-Nal-Arg-Trp-Asp-Arg-Phe-[Gly]
Ac-(Ac-Lys-Lys-)Lys-Lys-Tyr-Val-Nle-Gly-His-(D-Nal)-Arg-Trp-Asp-Arg-Phe-[Gly]
Ac-(Ac-Lys-Lys-)Lys-Lys-Tyr-Val-Nle-Gly-His-Phe-Arg-Trp-Asp-Arg-(D-Phe)-[Gly]
Ac-(Ac-Lys-Lys-)Lys-Lys-Tyr-Val-Nle-Gly-His-(D-Phe)-Arg-Trp-Asp-Arg-(D-Phe)-[Gly]
Ac-(Ac-Lys-Lys-)Lys-Lys-Tyr-Val-Nle-Gly-His-Phe-(D-Arg)-Trp-Asp-Arg-(D-Phe)-[Gly]
Ac-(Ac-Lys-Lys-)Lys-Lys-Tyr-Val-Nle-Gly-His-Phe-Arg-(D-Trp)-Asp-Arg-(D-Phe)-[Gly]
Ac-(Ac-Lys-Lys-)Lys-Lys-Tyr-Val-Nle-Gly-His-(D-Phe)-Arg-(D-Trp)-Asp-Arg-(D-Phe)-[Gly]
Ac-(Ac-Lys-)Lys-Lys-Tyr-Val-Nle-Gly-His-Nal-Arg-Trp-Asp-Arg-(D-Phe)-[Gly]
Ac-(Ac-Lys-)Lys-Lys-Tyr-Val-Nle-Gly-His-(D-Nal)-Arg-Trp-Asp-Arg-(D-Phe)-[Gly)
[Gly] is an optional amino acid in the sequence (may be present or absent)
The C-terminal Phe or Gly may be amidated (NH$_2$).

X = Ac-Lys-(Ac-Lys-)Lys-:.
Ac-(Ac-Lys-)Lys-Tyr-Val-Met-Gly-His-Phe-Arg-Trp-Asp-Arg-Phe-[Gly] (Ac-Lys-(Ac-Lys-)Lys-SEQ ID NO:s 11 or 7)
Ac-Lys-(Ac-Lys-)Lys-Tyr-Val-Met-Gly His-(D-Phe)-Arg-Trp-Asp-Arh-Phe-[Gly]
Ac-Lys-(Ac-Lys-)Lys-Tyr-Val-Met-Gly-His-Phe-(D-Arg)-Trp-Asp-Arg-Phe-[Gly]
Ac-Lys-(Ac-Lys-)Lys-Tyr-Val-Met-Gly-His-Phe-Arg-(D-Trp)-Asp-Arg-Phe-[Gly]
Ac-Lys-(Ac-Lys-)Lys-Tyr-Val-Met-Gly-His-(D-Phe)-Arg-(D-Trp)-Asp-Arg-Phe-[Gly]
Ac-Lys-(Ac-Lys-)Lys-Tyr-Val-Met-Gly-His-Nal-Arg-Trp-Asp-Arg-Phe-[Gly]
Ac-Lys-(Ac-Lys-)Lys-Tyr-Val-Met-Gly-His-(D-Nal)-Arg-Trp-Asp-Arg-Phe-[Gly]
Ac-Lys-(Ac-Lys-)Lys-Tyr-Val-Met-Gly-His-Phe-Arg-Trp-Asp-Arg-(D-Phe)-[Gly]
Ac-Lys-(Ac-Lys-)Lys-Tyr-Vel-Met-Gly-His-(D-Phe)-Arg-Trp-Asp-Arg-(D-Phe)-[Gly]
Ac-Lys-(Ac-Lys-)Lys-Tyr-Val-Met-Gly-His-Phe-(D-Arg)-Trp-Asp-Arg-(D-Phe)-[Gly]
Ac-Lys-(Ac-Lys-)Lys-Tyr-Val-Met-Gly-His-Phe-Arg-(D-Trp)-Asp-Arg-(D-Phe)-[Gly]
Ac-Lys-(Ac-Lys-)Lys-Tyr-Val-Met-Gly-His-(D-Phe)-Arg-(D-Trp)-Asp-Arg-(D-Phe)-[Gly]
Ac-Lys-(Ac-Lys-)Lys-Tyr-Val-Met-Gly-His-Nal-Arg-Trp-Asp-Arg-(D-Phe)-[Gly]
Ac-Lys-(Ac-Lys-)Lys-Tyr-Val-Met-Gly-His-(D-Nal)-Arg-Trp-Asp-Arq-(D-Phe)-[Gly]
Ac-Lys-(Ac-Lys-)Lys-Tyr-Val-Nle-Gly-His-Phe-Aro-Trp-Asp-Aro-Phe-[Gly] (Ac-Lys-(Ac-Lys-)Lys-SEQ ID NO:s 13 or 9)
Ac-Lys-(Ac-Lys-)Lys-Tyr-Val-Nle-Gly-His-(D-Phe)-Arg-Trp-Asp-Arg-Phe-[Gly]
Ac-Lys-(Ac-Lys-)Lys-Tyr-Val-Nle-Gly-His-Phe-(D-Arg)-Trp-Asp-Arg-Phe-[Gly]
Ac-Lys-(Ac-Lys-)Lys-Tyr-Val-Nle-Gly-His-Phe-Arg-(D-Trp)-Asp-Arg-Phe-[Gly]
Ac-Lys-(Ac-Lys-)Lys-Tyr-Val-Nle-Gly-His-(D-Phe)-Arg-(D-Trp)-Asp-Arg-Phe-[Gly]
Ac-Lys-(Ac-Lys-)Lys-Tyr-Val-Nle-Gly-His-Nal-Arg-Trp-Asp-Arg-Phe-[Gly]
Ac-Lys-(Ac-Lys-)Lys-Tyr-Val-Nle-Gly-His-(D-Nal)-Arg-Trp-Asp-Arg-Phe-[Gly]
Ac-Lys-(Ac-Lys-)Lys-Tyr-Val-Nle-Gly-His-Phe-Arg-Trp-Asp-Arg-(D-Phe)-[Gly]
Ac-Lys-(Ac-Lys-)Lys-Tyr-Val-Nle-Gly-His-(D-Phe)-Arg-Trp-Asp-Arg-(D-Phe)-[Gly]
Ac-Lys-(Ac-Lys-)Lys-Tyr-Val-Nle-Gly-Hiis-Phe-(D-Arg)-Trp-Asp-Arg-(D-Phe)-[Gly]
Ac-Lys-(Ac-Lys-)Lys-Tyr-Val-Nle-Gly-His-Phe-Arp-(D-Trp)-Asp-Arg-(D-Phe)-[Gly]
Ac-Lys-(Ac-Lys-)Lys-Tyr-Val-Nle-Gly-His-(D-Phe)-Arg-(D-Trp)-Asp-Arg-(D-Phe)-[Gly]

APPENDIX-continued

Examples of sequences of MSH analogues

Ao-Lys-(Ac-Lys-)Lys-Tyr-Val-Nle-Gly-His-Nal-Arg-Trp-Asp-Arg-(D-Phe)-[Gly]
Ao-Lys-(Ac-Lys-)Lys-Tyr-Val-Nle-Gly-His-(D-Nal)-Arg-Trp-Asp-Arg-(D-Phe)-[Gly]
[Gly] is an optional amino acid in the sequence may be present or absent
The C-terminal Phe or Gly may be amidated (NH$_2$).

X = Ac-Lys-(Ac-Lys-)Lys-:
Ac-Lys-(Ac-Lys-Lys-)Lys-Tyr-Val-Met-Gly-His-Phe-Arg-Trp-Asp-Arg-Phe-[Gly] (Ac-Lys-(Ac-Lys-Lys-)Lys-SEQ ID NO:s 11 or 7)
Ac-Lys-(Ac-Lys-Lys-)Lys-Tyr-Val-Met-Gly-His-(D-Phe)-Arg-Trp-Asp-Arg-Phe-[Gly]
Ac-Lys-(Ac-Lys-Lys-)Lys-Tyr-Val-Met-Gly-His-Phe-(D-Arg)-Trp-Asp-Arg-Phe-[Gly]
Ac-Lys-(Ac-Lys-Lys-)Lys-Tyr-Val-Met-Gly-His-Phe-Arg-(D-Trp)-Asp-Arg-Phe-[Gly]
Ac-Lys-(Ac-Lys-Lys-)Lys-Tyr-Val-Met-Gly-His-(D-Phe)-Arg-(D-Trp)-Asp-Arg-Phe-[Gly]
Ac-Lys-(Ac-Lys-Lys-)Lys-Tyr-Val-Met-Gly-His-Nal-Arg-Trp-Asp-Arg-Phe-[Gly]
Ac-Lys-(Ac-Lys-Lys-)Lys-Tyr-Val-Met-Gly-His-(D-Nal)-Arg-Trp-Asp-Arg-Phe-[Gly]
Ac-Lys-(Ac-Lys-Lys-)Lys-Tyr-Val-Met-Gly-His-Phe-Arg-Trp-Asp-Arg-(D-Phe)-[Gly]
Ac-Lys-(Ac-Lys-Lys-)Lys-Tyr-Val-Met-Gly-His-(D-Phe)-Arg-Trp-Asp-Arg-(D-Phe)-[Gly]
Ac-Lys-(Ac-Lys-Lys-)Lys-Tyr-Val-Met-Gly-His-Phe-(D-Arg)-Trp-Asp-Arg-(D-Phe)-[Gly]
Ac-Lys-(Ac-Lys-Lys-)Lys-Tyr-Val-Met-Gly-His-Phe-Arg-(D-Trp)-Asp-Arg-(D-Phe)-[Gly]
Ac-Lys-(Ac-Lys-Lys-)Lys-Tyr-Val-Met-Gly-His-(D-Phe)-Arg-(D-Trp)-Asp-Arg-(D-Phe)-[Gly]
Ac-Lys-(Ac-Lys-Lys-)Lys-Tyr-Val-Met-Gly-His-Nal-Arg-Trp-Asp-Arg-(D-Phe)-[Gly]
Ac-Lys-(Ac-Lys-Lys-)Lys-Tyr-Val-Met-Gly-His-(D-Nal)-Arg-Trp-Asp-Arg-(D-Phe)-[Gly]
Ac-Lys-(Ac-Lys-Lys-)Lys-Tyr-Val-Nle-Gly-His-Phe-Arg-Trp-Asp-Arg-Phe-[Gly] (AP-Lys-(Ac-Lys-Lys-)Lys-SEQ ID NO:s 13 or 9)
Ac-Lys-(Ac-Lys-Lys-)Lys-Tyr-Val-Nle-Gly-His-(D-Phe)-Arg-Trp-Asp-Arg-Phe-[Gly]
Ac-Lys-(Ac-Lys-Lys-)Lys-Tyr-Val-Nle-Gly-His-Phe-(D-Arg)-Trp-Asp-Arg-Phe-[Gly]
Ac-Lys-(Ac-Lys-Lys-)Lys-Tyr-Val-Nle-Gly-His-Phe-Arg-(D-Trp)-Asp-Arg-Phe-[Gly]
Ac-Lys-(Ac-Lys-Lys-)Lys-Tyr-Val-Nle-Gly-His-(D-Phe)-Arg-(D-Trp)-Asp-Arg-Phe-[Gly]
Ac-Lys-(Ac-Lys-Lys-)Lys-Tyr-Val-Nle-Gly-His-Nal-Arg-Trp-Asp-Arg-Phe-[Gly]
Ac-Lys-(Ac-Lys-Lys-)Lys-Tyr-Val-Nle-Gly-His-(D-Nal_-Arg-Trp-Asp-Arg-Phe-[Gly]
Ac-Lys-(Ac-Lys-Lys-)Lys-Tyr-Val-Nle-Gly-His-Phe-Arg-Trp-Asp-Arg-(D-Phe)-[Gly]
Ac-Lys-(Ac-Lys-Lys-)Lys-Tyr-Val-Nle-Gly-His-(D-Phe)-Arg-Trp-Asp-Arg-(D-Phe)-[Gly]
Ac-Lys-(Ac-Lys-Lys-)Lys-Tyr-Val-Nle-Gly-His-Phe(D-Arg)-Trp-Asp-Arg-(D-Phe)-[Gly]
Ac-Lys-(Ac-Lys-Lys-)Lys-Tyr-Val-Nle-Gly-His-Phe-Arg-(D-Trp)-Asp-Arg-(D-Phe)-[Gly]
Ac-Lys-(Ac-Lys-Lys-)Lys-Tyr-Val-Nle-Gly-His-(D-Phe)-Arg-(D-Trp)-Asp-Arg-(D-Phe)-[Gly]
Ac-Lys-(Ac-Lys-Lys-)Lys-Tyr-Val-Nle-Gly-His-Nal-Arg-Trp-Asp-Arg-(D-Phe)-[Gly]
Ac-Lys-(Ac-Lys-Lys-)Lys-Tyr-Val-Nle-Gly-His-(D-Nal)-Arg-Trp-Asp-Arg-(D-Phe)-[Gly]
[Gly] is an optional amino acid in the sequence may be present or absent)
The C-terminal Phe or Gly may be emidated (NH$_2$).

X = (Ac-Lys-)Lys-(Ac-Lys)Lys-:
Ac-(Ac-Lys-)Lys-(Ac-Lys)Lys-Tyr-Val-Met-Gly-His-Phe-Arg-Trp-Asp-Arg-Phe-[Gly] (Ac-(Ac-Lys-)Lys-(Ac-Lys)Lys-SEQ ID NO:s 11 or 7)
Ac-(Ac-Lys-)Lys-(Ac-Lys)Lys-Tyr-Val-Met-Gly-His-(D-Phe)-Arg-Trp-Asp-Arg-Phe-[Gly]
Ac-(Ac-Lys-)Lys-(Ac-Lys)Lys-Tyr-Val-Met-Gly-His-Phe-(D-Arg)-Trp-Asp-Arg-Phe-[Gly]
Ac-(Ac-Lys-)Lys-(Ac-Lys)Lys-Tyr-Val-Met-Gly-His-Phe-Arg-(D-Trp)-Asp-Arg-Phe-[Gly]
Ac-(Ac-Lys-)Lys-(Ac-Lys)Lys-Tyr-Val-Met-Gly-His-(D-Phe)-Arg-(D-Trp)-Asp-Arg-Phe-[Gly]
Ac-(Ac-Lys-)Lys-(Ac-Lys)Lys-Tyr-Val-Met-Gly-His-Nal-Arg-Trp-Asp-Arg-Phe-[Gly]
Ac-(Ac-Lys-)Lys-(Ac-Lys)Lys-Tyr-Val-Met-Gly-His-(D-Nal)-Arg-Trp-Asp-Arg-Phe-[Gly]
Ac-(Ac-Lys-)Lys-(Ac-Lys)Lys-Tyr-Val-Met-Gly-His-Phe-Arg-Trp-Asp-Arg-(D-Phe)-[Gly]
Ac-(Ac-Lys-)Lys-(Ac-Lys)Lys-Tyr-Val-Met-Gly-His-(D-Phe)-Arg-Trp-Asp-Arg-(D-Phe)-[Gly]
Ac-(As-Lys-)Lys-(Ac-Lys)Lys-Tyr-Val-Met-Gly-His-Phe-(D-Arg)-Trp-Asp-Arg-(D-Phe)-[Gly]
Ac-(Ac-Lys-)Lys-(Ac-Lys)Lys-Tyr-Val-Met-Gly-His-Phe-Arg-(D-Trp)-Asp-Arg-(D-Phe)-[Gly]
Ac-(Ac-Lys)-Lys-(Ac-Lys)Lys-Tyr-Val-Met-Gly-His-(D-Phe)-Arg-(D-Trp)-Asp-Arg-(D-Phe)-[Gly]
Ac-(Ac-Lys)-Lys-(As-Lys)Lys-Tyr-Val-Met-Gly-His-Nal-Arg-Trp-Asp-Arg-(D-Phe)-[Gly]
Ac-(Ac-Lys-)Lys-(Ac-Lys)Lys-Tyr-Val-Met-Gly-His-(D-Nal)-Arg-Trp-Asp-Arg-(D-Phe)-[Gly]
Ac-(Ac-Lys-)Lys-(Ac-Lys)Lys-Tyr-Val-Nle-Gly-His-Phe-Arg-Trp-Asp-Arg-Phe-[Gly] (Ac-(Ac-Lys-)Lys-(Ac-Lys)Lys-SEQ ID NO:s 13 of 9)
Ac-(Ac-Lys-)Lys-(Ac-Lys)Lys-Tyr-Val-Nle-Gly-His-(D-Phe)-Arg-Trp-Asp-Arg-Phe-[Gly]
Ac-(Ac-Lys-)Lys-(Ac-Lys)Lys-Tyr-Val-Nle-Gly-His-Phe-(D-Arg)-Trp-Asp-Arg-Phe-[Gly]
Ac-(Ac-Lys-)Lys-(Ac-Lys)Lys-Tyr-Val-Nle-Gly-His-Phe-Arg-(D-Trp)-Asp-Arg-Phe-[Gly]
Ac-(Ac-Lys-)Lys-(Ac-Lys)Lys-Tyr-Val-Nle-Nle-Gly-His-(D-Phe)-Arg-(D-Trp)-Asp-Arg-Phe-[Gly]
Ac-(Ac-Lys-)Lys-(Ac-Lys)Lys-Tyr-Val-Nle-Gly-His-Nal-Arg-Trp-Asp-Arg-Phe-[Gly]
Ac-(Ac-Lys-)Lys-(Ac-Lys)Lys-Tyr-Val-Nle-Gly-His-(D-Nal)-Arg-Trp-Asp-Arg-Phe-[Gly]
Ac-(Ac-Lys-)Lys-(Ac-Lys)Lys-Tyr-Val-Nle-Gly-His-Phe-Arg-Trp-Asp-Arg-(D-Phe)-[Gly]
Ac-(Ac-Lys-)Lys-(Ac-Lys)Lys-Tyr-Val-Nle-Gly-His-(D-Phe)-Arg-Trp-Asp-Arg-(D-Phe)-[Gly]
Ac-(Ac-Lys-)Lys-(Ac-Lys)Lys-Tyr-Val-Nle-Gly-His-Phe-(D-Arg)-Trp-Asp-Arg-(D-Phe)-[Gly]
Ac-(Ac-Lys-)Lys-(Ac-Lys)Lys-Tyr-Val-Nle-Gly-His-Phe-Arg-(D-Trp)-Asp-Arg-(D-Phe)-[Gly]

APPENDIX-continued

Examples of sequences of MSH analogues

Ac-(Ac-Lys-)Lys-(Ac-Lys)Lys-Tyr-Val-Nle-Gly-His-(D-Phe)-Arg-(D-Trp)-Asp-Arg-(D-Phe)-[Gly]
Ac-(Ac-Lys-)Lys-(Ac-Lys)Lys-Tyr-Val-Nle-Gly-His-Nal-Arg-Trp-Asp-Arg-(D-Phe)-[Gly]
Ac-(Ac-Lys-)Lys-(Ac-Lys)Lys-Tyr-Val-Nle-Gly-His-(D-Nal)-Arg-Trp-Asp-Arg-(D-Phe)-[Gly]
[Gly] is an optional amino acid in the sequence (may be present or absent)
The C-terminal Phe or Gly may he amidated (NH$_2$).

X = Ac-Lys-Lys-(Ac-Lys)Lys-:
Lys-Lys-(Ac-Lys-)Lys-Tyr-Val-Met-Gly-His-Phe-Arg-Trp-Asp-Arg-Phe-[Gly] (Ac-Lys-Lys-(Ac-Lys-)Lys-SEQ ID NO:s 11 or 7)
Ac-Lys-Lys-(Ac-Lys-)Lys-Tyr-Val-Met-Gly-His-(D-Phe)-Arg-Trp-Asp-Arg-Phe-[Gly]
Ac-Lys-Lys-(Ac-Lys-)Lys-Tyr-Val-Met-Gly-His-Phe-(D-Arg)-Trp-Asp-Arg-Phs-[Gly]
Ac-Lys-Lys-(Ac-Lys-)Lys-Tyr-Val-Met-Gly-His-Phe-Arg-(D-Trp)-Asp-Arg-Phe-[Gly]
Ac-Lys-Lys-(Ac-Lys-)Lys-Tyr-Val-Met-Gly-His-(D-Phe)-Arg-(D-Trp)-Asp-Arg-Phe-[Gly]
Ac-Lys-Lys-(Ac-Lys-)Lys-Tyr-Val-Met-Gly-His-Nal-Arg-Trp-Asp-Arg-Phe-[Gly]
Ac-Lys-Lys-(Ac-Lys-)Lys-Tyr-Val-Met-Gly-His-(D-Nal)-Arg-Trp-Asp-Arg-Phe-[Gly]
Ac-Lys-Lys-(Ac-Lys-)Lys-Tyr-Val-Met-Gly-His-Phe-Arg-Trp-Asp-Arg-(D-Phe)-[Gly]
Ac-Lys-Lys-(Ac-Lys-)Lys-Tyr-Val-Met-Gly-His-(D-Phe)-Arg-Trp-Asp-Arg-(D-Phe)-[Gly]
Ac-Lys-Lys-(Ac-Lys-)Lys-Tyr-Val-Met-Gly-His-Phe-(D-Arg)-Trp-Asp-Arg-(D-Phe)-[Gly]
Ac-Lys-Lys-(Ac-Lys-)Lys-Tyr-Val-Met-Gly-His-Phe-Arg-(D-Trp)-Asp-Arg-(D-Phe)-[Gly]
Ac-Lys-Lys-(Ao-Lys-)Lys-Tyr-Val-Met-Gly-His-(D-Phe)-Arg-(D-Trp)-Asp-Arg-(D-Phe)-[Gly]
Ac-Lys-Lys-(Ac-Lys-)Lys-Tyr-Val-Met-Gly-His-Nal-Arg-Trp-Asp-Arp-(D-Phe)-[Gly]
Ac-Lys-Lys-(Ac-Lys-)Lys-Tyr-Val-Met-Gly-His-(D-Nal)-Arg-Trp-Asp-Arg-(D-Phe)-[Gly]
Ac-Lys-Lys-(Ac-Lys-)Lys-Tyr-Val-Nle-Gly-His-Phe-Arg-Trp-Asp-Arg-Phe-[Gly] (Ac-Lys-Lys-(Ac-Lys-)Lys-SEQ ID NO:s 13 or 9)
Ac-Lys-Lys-(Ac-Lys-)Lys-Tyr-Val-Nle-Gly-His-(D-Phe)-Arg-Trp-Asp-Arg-Phe-[Gly]
Ac-Lys-Lys-(Ac-Lys-)Lys-Tyr-Val-Nle-Gly-His-Phe-(D-Arg)-Trp-Asp-Arg-Phe-[Gly]
Ac-Lys-Lys-(Ac-Lys-)Lys-Tyr-Val-Nle-Gly-His-Phe-Arg-(D-Trp)-Asp-Arg-Phe-[Gly]
Ac-Lys-Lys-(Ac-Lys-)Lys-Tyr-Val-Nle-Gly-His-(D-Phe)-Arg-(D-Trp)-Asp-Arg-Phe-[Gly]
Ac-Lys-Lys-(Ac-Lys-)Lys-Tyr-Val-Nle-Gly-His-Nal-Arg-Trp-Asp-Arg-Phe-[Gly]
Ac-Lys-Lys-(Ac-Lys-)Lys-Tyr-Val-Nle-Gly-His-(D-Nal)-Arg-Trp-Asp-Arg-Phe-[Gly]
Ac-Lys-Lys-(Ac-Lys-)Lys-Tyr-Val-Nle-Gly-His-Phe-Arg-Trp-Asp-Arg-(D-Phe)-[Gly]
Ac-Lys-Lys-(Ac-Lys-)Lys-Tyr-Val-Nle-Gly-His-(D-Phe)-Arg-Trp-Asp-Arg-(D-Phe)-[Gly]
Ac-Lys-Lys-(Ac-Lys-)Lys-Tyr-Val-Nle-Gly-His-Phe-(D-Arg)-Trp-Asp-Arg-(D-Phe)-[Gly]
Ac-Lys-Lys-(Ac-Lys-)Lys-Tyr-Val-Nle-Gly-His-Phe-Arg-(D-Trp)-Asp-Arg-(D-Phe)-[Gly]
Ac-Lys-Lys-(Ac-Lys-)Lys-Tyr-Val-Nle-Gly-His-(D-Phe)-Arg-(D-Trp)-Asp-Arg-(D-Phe)-[Gly]
Ac-Lys-Lys-(Ac-Lys-)Lys-Tyr-Val-Nle-Gly-His-Nal-Arg-Trp-Asp-Arg-(D-Phe)-[Gly]
Ac-Lys-Lys-(Ac-Lys-)Lys-Tyr-Val-Nle-Gly-His-(D-Nal)-Arg-Trp-Asp-Arg-(D-Phe)-[Gly]
[Gly] is an optional amino acid in the sequence (may be present or absent)
The C-terminal Phe or Gly may be amidated (NH$_2$).

X = Ac-Lys-(Ac-Lys-)Lys-Lys-:
Ac-Lys-(Ac-Lys-)Lys-Lys-Tyr-Val-Met-Gly-His-Phe-Arg-Trp-Asp-Arg-Phe-[Gly] (Ac-Lys-(Ac-Lys-)Lys-Lys-SEQ ID NO:s 11 or 7)
Ac-Lys-(Ac-Lys-)Lys-Lys-Tyr-Val-Met-Gly-His-(D-Phe)-Arg-Trp-Asp-Arg-Phe-[Gly]
Ac-Lys-(Ac-Lys-)Lys-Lys-Tyr-Val-Met-Gly-His-Phe-(D-Arg)-Trp-Asp-Arg-Phe-[Gly]
Ac-Lys-(Ac-Lys-)Lys-Lys-Tyr-Val-Met-Gly-His-Phe-Arg-(D-Trp)-Asp-Arg-Phe-[Gly]
Ac-Lys-(Ac-Lys-)Lys-Lys-Tyr-Val-Met-Gly-His-(D-Phe)-Arg-(D-Trp)-Asp-Arg-Phe-[Gly]
Ac-Lys-(Ac-Lys-)Lys-Lys-Tyr-Val-Met-Gly-His-Nal-Arg-Trp-Asp-Arg-Phe-[Gly]
Ac-Lys-(Ac-Lys-)Lys-Lys-Tyr-Val-Met-Gly-His-(D-Nal)-Arg-Trp-Asp-Arg-Phe-[Gly]
Ac-Lys-(Ac-Lys-)Lys-Lys-Tyr-Val-Met-Gly-His-Phe-Arg-Trp-Asp-Arg-(D-Phe)-[Gly]
Ac-Lys-(Ac-Lys-)Lys-Lys-Tyr-Val-Met-Gly-His-(D-Phe)-Arg-Trp-Asp-Arg-(D-Phe)-[Gly]
Ac-Lys-(Ac-Lys-)Lys-Lys-Tyr-Val-Met-Gly-His-Phe-(D-Arg)-Trp-Asp-Arg-(D-Phe)-[Gly]
Ac-Lys-(Ac-Lys-)Lys-Lys-Tyr-Val-Met-Gly-His-Phe-Arg-(D-Trp)-Asp-Arg-(D-Phe)-[Gly]
Ac-Lys-(Ao-Lys-)Lys-Lys-Tyr-Val-Met-Gly-His-(D-Phe)-Arg-(D-Trp)-Asp-(D-Phe)-[Gly]
Ac-Lys-(Ac-Lys-)Lys-Lys-Tyr-Val-Met-Gly-His-Nal-Arg-Trp-Asp-Arg-(D-Phe)-[Gly]
Ac-Lys-(Ac-Lys-)Lys-Lys-Tyr-Val-Met-Gly-His-(D-Nal)-Arg-Trp-Asp-Arg-(D-Phe)-[Gly]
Ac-Lys-(Ac-Lys-)Lys-Lys-Tyr-Val-Nle-Gly-His-Phe-Arg-Trp-Asp-Arg-Phe-[Gly] (Ac-Lys-(Ac-Lys-)Lys-Lys-SEQ ID NO:s 13 or 9)
Ac-Lys-(Ac-Lys-)Lys-Lys-Tyr-Val-Nle-Gly-His-(D-Phe)-Arg-Trp-Asp-Arg-Phe-[Gly]
Ac-Lys-(Ac-Lys-)Lys-Lys-Tyr-Val-Nle-Gly-His-Phe-(D-Arg)-Trp-Asp-Arg-Phe-[Gly]
Ac-Lys-(Ac-Lys-)Lys-Lys-Tyr-Val-Nle-Gly-His-Phe-Arg-(D-Ttp)-Asp-Arg-Phe-[Gly]
Ac-Lys-(Ac-Lys-)Lys-Lys-Tyr-Val-Nle-Gly-His-(D-Phe)-Arg-(D-Trp)-Asp-Arg-Phe-[Gly]
Ac-Lys-(Ac-Lys-)Lys-Lys-Tyr-Val-Nle-Gly-His-Nal-Arg-Trp-Asp-Arg-Phe-[Gly]
Ac-Lys-(Ac-Lys-)Lys-Lys-Tyr-Val-Nle-Gly-His-(D-Nal)-Arg-Trp-Asp-Arg-Phe-[Gly]
Ac-Lys-(Ac-Lys-)Lys-Lys-Tyr-Val-Nle-Gly-His-Phe-Arg-Trp-Asp-Arg-(D-Phe)-[Gly]
Ac-Lys-(Ac-Lys-)Lys-Lys-Tyr-Val-Nle-Gly-His-(D-Phe)-Arg-Trp-Asp-Arg-(D-Phe)-[Gly]
Ac-Lys-(Ac-Lys-)Lys-Lys-Tyr-Val-Nle-Gly-His-Phe-(D-Arg)-Trp-Asp-Arg-(D-Phe)-[Gly]
Ac-Lys-(Ac-Lys-)Lys-Lys-Tyr-Val-Nle-Gly-His-Phe-Arg-(D-Trp)-Asp-Arg-(D-Phe)-[Gly]
Ac-Lys-(Ac-Lys-)Lys-Lys-Tyr-Val-Nle-Gly-His-(D-Phe)-Arg-(D-Trp)-Asp-Arg-(D-Phe)-[Gly]
Ac-Lys-(Ac-Lys-)Lys-Lys-Tyr-Val-Nle-Gly-His-Nal-Arg-Trp-Asp-(D-Phe)-[Gly]
Ac-Lys-(Ac-Lys-)Lys-Lys-Tyr-Val-Nle-Gly-His-(D-Nal)-Arg-Trp-Asp-Arg-(D-Phe)-[Gly]
[Gly] is an optional amino acid in th sequence (may be present or absent)
The C-terrninal Phe Of Gly may be amidated (NH$_2$).

APPENDIX-continued

Examples of sequences of MSH analogues

```
X = Ac-(Ac-Lys)-Lys-Lys-Lys:
Ac-(Ac-Lys-)Lys-Lys-Lys-Tyr-Val-Met-Gly-His-Phe-Arg-Trp-Asp-Arg-Phe-[Gly]   (Ac-(Ac-
Lys-)Lys-Lys-Lys-SEQ ID NO:s 11 or 7)
Ac-(Ac-Lys-)Lys-Lys-Lys-Tyr-Val-Met-Gly-His-(D-Phe)-Arg-Trp-Asp-Arg-Phe-[Gly]
Ac-(Ac-Lys-)Lys-Lys-Lys-Tyr-Val-Met-Gly-His-Phe-(D-Arg)-Trp-Asp-Arg-Phe-[Gly]
Ac-(Ac-Lys-)Lys-Lys-Lys-Tyr-Val-Met-Gly-His-Phe-Arg-(D-Trp)-Asp-Arg-Phe-[Gly]
Ac-(Ac-Lys-)Lys-Lys-Lys-Tyr-Val-Met-Gly-His-(D-Phe)-Arg-(D-Trp)-Asp-Arg-Phe-[Gly]
Ac-(Ac-Lys-)Lys-Lys-Lys-Tyr-Val-Met-Gly-His-Nal-Arg-Tr-Asp-Arg-Phe-[Gly]
Ac-(Ac-Lys-)Lys-Lys-Lys-Tyr-Val-Met-Gly-His-(D-Nal)-Arg-Trp-Asp-Arg-Phe-[Gly]
Ac-(Ac-Lys-)Lys-Lys-Lys-Tyr-Val-Met-Gly-His-Phe-Arg-Trp-Asp-Arg-(D-Phe)-[Gly]
Ac-(Ac-Lys-)Lys-Lys-Lys-Tyr-Val-Met-Gly-His-(D-Phe)-Arg-Trp-Asp-Arg-(D-Phe)-[Gly]
Ac-(Ac-Lys-)Lys-Lys-Lys-Tyr-Val-Met-Gly-His-Phe-(D-Arg)-Trp-Asp-Arg-(D-Phe)-[Gly]
Ac-(Ac-Lys-)Lys-Lys-Lys-Tyr-Val-Met-Gly-His-Phe-Arg-(D-Trp)-Asp-Arg-(D-Phe)-[Gly]
Ac-(Ac-Lys-)Lys-Lys-Lys-Tyr-Val-Met-Gly-His-(D-Phe)-Arg-(D-Trp)-Asp-Arg-(D-Phe)-[Gly]
Ac-(Ac-Lys-)Lys-Lys-Lys-Tyr-Val-Met-Gly-His-Nal-Arg-Trp-Asp-Arg-(D-Phe)-[Gly]
Ac-(Ac-Lys-)Lys-Lys-Lys-Tyr-Val-Met-Gly-His-(D-Nal)-Arg-Trp-Asp-Arg-(D-Phe)-[Gly]
Ac-(Ac-Lys-)Lys-Lys-Lys-Tyr-Val-Nle-Gly-His-Phe-Arg-Trp-Asp-Arg-Phe-[Gly]   (Ac-(Ac-
Lys-)Lys-Lys-Lys-SEQ ID NO:s 13 or 9)
Ac-(Ac-Lys-)Lys-Lys-Lys-Tyr-Val-Nle-Gly-His-(D-Phe)-Arg-Trp-Asp-Arg-Phe-[Gly]
Ac-(Ac-Lys-)Lys-Lys-Lys-Tyr-Val-Nle-Gly-His-Phe-(D-Arg)-Thr-Asp-Arg-Phe-[Gly]
Ac-(Ac-Lys-)Lys-Lys-Lys-Tyr-Val-Nle-Gly-His-Phe-Arg-(D-Trp)-Asp-Arg-Phe-[Gly]
Ac-(Ac-Lys-)Lys-Lys-Lys-Tyr-Val-Nle-Gly-His-(D-Phe)-Arg-(D-Trp)-Asp-Arg-Phe-[Gly]
Ac-(Ac-Lys-)Lys-Lys-Lys-Tyr-Val-Nle-Gly-His-Nal-Arg-Trp-Asp-Arg-Phe-[Gly]
Ac-(Ac-Lys-)Lys-Lys-Lys-Tyr-Val-Nle-Gly-His-(D-Nal)-Arg-Trp-Asp-Arg-Phe-[Gly]
Ac-(Ac-Lys-)Lys-Lys-Lys-Tyr-Val-Nle-Gly-His-Phe-Arg-Trp-Asp-Arg-(D-Phe)-[Gly]
Ac-(Ac-Lys-)Lys-Lys-Lys-Tyr-Val-Nle-Gly-His-(D-Phe)-Arg-Trp-Asp-Arg-(D-Phe)-[Gly]
Ac-(Ac-Lys-)Lys-Lys-Lys-Tyr-Val-Nle-Gly-His-Phe-(D-Arg)-Trp-Asp-Arg-(D-Phe)-[Gly]
Ac-(Ac-Lys-)Lys-Lys-Lys-Tyr-Val-Nle-Gly-His-Phe-Arg-(D-Trp)-Asp-Arg-(D-Phe)-[Gly]
Ac-(Ac-Lys-)Lys-Lys-Lys-Tyr-Val-Nle-Gly-His-(D-Phe)-Arg-(D-Trp)-Asp-Arg-(D-Phe)-
[Gly]
Ac-(Ac-Lys-)Lys-Lys-Lys-Tyr-Val-Nle-Gly-His-Nal-Arg-Trp-Asp-Arg-(D-Phe)-[Gly]
Ac-(Ac-Lys-)Lys-Lys-Lys-Tyr-Val-Nle-Gly-His-(D-Nal)-Arg-Trp-Asp-Arg-(D-Phe)-[Gly]
[Gly] is an optional amino acid in the sequence (may be present or absent)
The C-terminal Phe or Gly may be amidated (NH$_2$).

X = Ac-(Ac-Lys-Gly-)Lys-Lys-:
Ac-(Ac-Lys-Gly-)Lys-Lys-Tyr-Val-Met-Gly-His-Phe-Arg-Trp-AsP-Arg-Phe-[Gly]   (Ac-(Ac-
Lys-Gly-)Lys-Lys-SEQ ID NO 11 or 7)
Ac-(Ac-Lys-Gly-)Lys-Lys-Tyr-Val-Met-Gly-His-(D-Phe)-Arg-Trp-Asp-Arg-Phe-[Gly]
Ac-(Ac-Lys-Gly-)Lys-Lys-Tyr-Val-Met-Gly-His-Phe-(D-Arg)-Trp-Asp-Arg-Phe-[Gly]
Ac-(Ac-Lys-Gly-)Lys-Lys-Tyr-Val-Met-Gly-His-Phe-Arg-(D-Trp)-Asp-Arg-Phe-[Gly]
Ac-(Ac-Lys-Gly-)Lys-Lys-Tyr-Val-Met-Gly-His-(D-Phe)-Arg-(D-Trp)-Asp-Arg-Phe-[Gly]
Ac-(Ac-Lys-Gly-)Lys-Lys-Tyr-Val-Met-Gly-His-Nal-Arg-Trp-Asp-Arg-Phe-[Gly]
Ac-(Ac-Lys-Gly-)Lys-Lys-Tyr-Val-Met-Gly-His-(D-Nal)-Arg-Trp-Asp-Arg-Phe-[Gly]
Ac-(Ac-Lys-Gly-)Lys-Lys-Tyr-Val-Met-Gly-His-Phe-Arg-Trp-Asp-Arg-(D-Phe)[Gly]
Ac-(Ac-Lys-Gly-)Lys-Lys-Tyr-Val-Met-Gly-His-(D-Phe)-Arg-Trp-Asp-Arg-(D-Phe)-[Gly]
Ac-(Ac-Lys-Gly-)Lys-Lys-Tyr-Val-Met-Gly-His-Phe-(D-Arg)-Trp-Asp-Arg-(D-Phe)-[Gly]
Ac-(Ac-Lys-Gly-)Lys-Lys-Tyr-Val-Met-Gly-His-Phe-Arg-(D-Trp)-Asp-Arg-(D-Phe)-[Gly]
Ac-(Ac-Lys-Gly-)Lys-Lys-Tyr-Val-Met-Gly-His-(D-Phe)-Arg-(D-Trp)-Asp-Arg-(D-Phe)-
[Gly]
Ac-(Ac-Lys-Gly-)Lys-Lys-Tyr-Val-Met-Gly-His-Nal-Arg-Trp-Asp-Arg-(D-Phe)-[Gly]
Ac-(Ac-Lys-Gly-)Lys-Lys-Tyr-Val-Met-Gly-His-(D-Nal)-Arg-Trp-Asp-Arg-(D-Phe)-[Gly]
Ac-(Ac-Lys-Gly-)Lys-Lys-Tyr-Val-Nle-Gly-His-Phe-Arg-Trp-Asp-Arg-Phe-(Ac-(Ac-
Lys-Gly-)Lys-Lys-SEQ ID NO:s 13 or 9)
Ac-(Ac-Lys-Gly-)Lys-Lys-Tyr-Val-Nle-Gly-His-(D-Phe)-Arg-Trp-Asp-Arg-Phe-[Gly]
Ac-(Ac-Lys-Gly-)Lys-Lys-Tyr-Val-Nle-Gly-His-Phe-(D-Arg)-Trp-Asp-Arg-Phe-[Gly]
Ac-(Ac-Lys-Gly-)Lys-Lys-Tyr-Val-Nle-Gly-His-Phe-Arg-(D-Trp)-Asp-Arg-Phe-[Gly]
Ac-(Ac-Lys-Gly-)Lys-Lys-Tyr-Val-Nle-Gly-His-(D-Phe)-Arg-(D-Trp)-Asp-Arg-Phe-[Gly]
Ac-(Ac-Lys-Gly-)Lys-Lys-Tyr-Val-Nle-Gly-His-Nal-Arg-Trp-Asp-Arg-Phe-[Gly]
Ac-(Ac-Lys-Gly-)Lys-Lys-Tyr-Val-Nle-Gly-His-(D-Nal)-Arg-Trp-Asp-Arg-Phe-[Gly]
Ac-(Ac-Lys-Gly-)Lys-Lys-Tyr-Val-Nle-Gly-His-Phe-Arg-Trp-Asp-Arg-(D-Phe)-[Gly]
Ac-(Ac-Lys-Gly-)Lys-Lys-Tyr-Val-Nle-Gly-His-(D-Phe)-Arg-Trp-Asp-Arg-(D-Phe)-[Gly]
Ac-(Ac-Lys-Gly-)Lys-Lys-Tyr-Val-Nle-Gly-His-Phe-(D-Arg)-Trp-Asp-Arg-(D-Phe)-[Gly]
Ac-(Ac-Lys-Gly-)Lys-Lys-Tyr-Val-Nle-Gly-His-Phe-Arg-(D-Trp)-Asp-Arg-(D-Phe)-[Gly]
Ac-(Ac-Lys-Gly-)Lys-Lys-Tyr-Val-Nle-Gly-His-(D-Phe)-Arg-(D-Trp)-Asp-Arg-(D-Phe)-
[Gly]
Ac-(Ac-Lys-Gly-)Lys-Lys-Tyr-Val-Nle-Gly-His-Nal-Arg-Trp-Asp-Arg-(D-Phe)-[Gly]
Ac-(Ac-Lys-Gly-)Lys-Lys-Tyr-Val-Nle-Gly-His-(D-Nal)-Arg-Trp-Asp-Arg-(D-Phe)-[Gly]
[Gly] is an optional a amino acid in the sequence (may be present or absent)
The C-terminal Phe or Gly may be amidated (NH$_2$).

X = Ac-Lys-(Ac-Lys-Gly-)Lys:
Ac-Lys-(Ac-Lys-Gly-)Lys-Tyr-Val-Met-Gly-His-Phe-Arg-Trp-Asp-Arg-Phe-[Gly]   (Ac-Lys-
Gly-)Lys-SEQ ID NO:s 11 or 7)
Ac-Lys-(Ac-Lys-Gly-)Lys-Tyr-Val-Met-Gly-His-(D-Phe)-Arg-Trp-Asp-Arg-Phe-[Gly]
Ac-Lys-(Ac-Lys-Gly-)Lys-Tyr-Val-Met-Gly-His-Phe-(D-Arg)-Trp-Asp-Arg-Phe-[Gly]
Ac-Lys-(Ac-Lys-Gly-)Lys-Tyr-Val-Met-Gly-His-Phe-Arg-(D-Trp)-Asp-Arg-Phe-[Gly]
```

APPENDIX-continued

Examples of sequences of MSH analogues

```
Ac-Lys-(Ac-Lys-Gly-)Lys-Tyr-Val-Met-Gly-His-(D-Phe)-Arg-(D-Trp)-Asp-Arg-Phe-[Gly]
Ac-Lys-(Ac-Lys-Gly-)Lys-Tyr-Val-Met-Gly-His-Nal-Arg-Trp-Asp-Arg-Phe-[Gly]
Ac-Lys-(Ac-Lys-Gly-)Lys-Tyr-Val-Met-Gly-His-(D-Nal)-Arg-Trp-Asp-Arg-Phe-[Gly]
Ac-Lys-(Ac-Lys-Gly-)Lys-Tyr-Val-Met-Gly-His-Phe-Arg-Trp-Asp-Arg-(D-Phe)-[Gly]
Ac-Lys-(Ac-Lys-Gly-)Lys-Tyr-Val-Met-Gly-His-(D-Phe)-Arg-Trp-Asp-Arg-(D-Phe)-[Gly]
Ac-Lys-(Ac-Lys-Gly-)Lys-Tyr-Val-Met-Gly-His-Phe-(D-Arg)-Trp-Asp-Arg-(D-Phe)-[Gly]
Ac-Lys-(Ac-Lys-Gly-)Lys-Tyr-Val-Met-Gly-His-Phe-Arg-(D-Trp)-Asp-Arg-(D-Phe)-[Gly]
Ac-Lys-(Ac-Lys-Gly-)Lys-Tyr-Val-Met-Gly-His-(D-Phe)-Arg-(D-Trp)-Asp-Arg-(D-Phe)-[Gly]
Ac-Lys-(Ac-Lys-Gly-)Lys-Tyr-Vat-Met-Gly-His-Nal-Arg-Trp-Asp-Arg-(D-Phe)-[Gly]
Ac-Lys-(Ac-Lys-Gly-)Lys-Tyr-Val-Met-Gly-His-(D-Nal)-Arg-Trp-Asp-Arg-(D-Phe)-[Gly]
Ac-Lys-(Ac-Lys-Gly-)Lys-Tyr-Val-Nle-Gly-His-Phe-Arg-Tre-Asp-Arg-Phe-[Gly] (Ac-Lys-(Ac-Lys-Gly-)Lys-SEQ ID NO: 13 or 9)
Ac-Lys-(Ac-Lys-Gly-)Lys-Tyr-Val-Nle-Gly-His-(D-Phe)-Arg-Trp-Asp-Arg-Phe-[Gly]
Ac-Lys-(Ac-Lys-Gly-)Lys-Tyr-Val-Nle-Gly-His-Phe-(D-Arg)-Trp-Asp-Arg-Phe-[Gly]
Ac-Lys-(Ac-Lys-Gly-)Lys-Tyr-Val-Nle-Gly-His-Phe-Arg-(D-Trp)-Asp-Arg-Phe-[Gly]
Ac-Lys-(Ac-Lys-Gly-)Lys-Tyr-Val-Nle-Gly-His-(D-Phe)-Arg-(D-Trp)-Asp-Arg-Phe-[Gly]
Ac-Lys-(Ac-Lys-Gly-)Lys-Tyr-Val-Nle-Gly-His-Nal-Arg-Trp-Asp-Arg-Phe-[Gly]
Ac-Lys-(Ac-Lys-Gly-)Lys-Tyr-Val-Nle-Gly-His-(D-Nal)-Arg-Trp-Asp-Arg-Phe-[Gly]
Ac-Lys-(Ac-Lys-Gly-)Lys-Tyr-Val-Nle-Gly-His-Phe-Arg-Trp-Asp-Arg-(D-Phe)-[Gly]
Ac-Lys-(Ac-Lys-Gly-)Lys-Tyr-Val-Nle-Gly-His-(D-Phe)-Arg-Trp-Asp-Arg-(D-Phe)-[Gly]
Ac-Lys-(Ac-Lys-Gly-)Lys-Tyr-Val-Nle-Gly-His-Phe-(D-Arg)-Trp-Asp-Arg-(D-Phe)-[Gly]
Ac-Lys-(Ac-Lys-Gly-)Lys-Tyr-Val-Nle-Gly-His-Phe-Arg-(D-Trp)-Asg-Arg-(D-Phe)-[Gly]
Ac-Lys-(Ac-Lys-Gly-)Lys-Tyr-Val-Nle-Gly-His-(D-Phe)-Arg-(D-Trp)-Asg-Arg-(D-Phe)-[Gly]
Ac-Lys-(Ac-Lys-Gly-)Lys-Tyr-Val-Nle-Gly-His-Nal-Arg-Trp-Asp-Arg-(D-Phe)-[Gly]
Ac-Lys-(Ac-Lys-Gly-)Lys-Tyr-Val-Nle-Gly-His-(D-Nal)-Arg-Trp-Asp-Arg-(D-Phe)-[Gly]
[Gly] is an optional amino acid in the sequence (may be present or absent)
The C-terminal Phe or Gly may be amidated (NH₂).
```

EXAMPLES

The potency and efficacy of the presently claimed invention can be determined using different pharmacological procedures. The present invention is further illustrated with reference to the following examples, which are not intended to be limiting in any way to the scope of the invention as claimed.

In the following the methods for testing the peptides of the invention are described in general. The results for the tested peptides are given in the below examples. The aim of the methods is to test the peptides of the invention for receptor binding affinity against the human MC1r and the efficacy against the human MC1r and MCr3.

The immune modulating effects of melanocortins are mediated through MC1r and/or MC3r stimulation on immune competent cells in tissues, organs and plasma. MC1r and/or MC3r are expressed in immune competent cells including monocytes, macrophages, neutrophils t-cells and dendritic cells. Stimulation of the MCr1 and/or MC3r is associated with attenuation of cytokine production and activation of pro-resolving effects. The binding affinity and the receptor efficacy (alternative expression is potency) of a given melanocortin together, in some embodiments, makes up the overall efficacy of a given compound. The degree of a given compounds' binding affinity against the MCr's is defined as the ability to displacement of a radio-labelled full agonist with high binding affinity to the receptor, in the given case displacement of $^{125}$I-NDP-αMSH from the MCr1. The binding affinity is expressed with an inhibition constant $IC_{50}$ defined as the concentration of a given compound inducing 50% displacement of the radio-labelled compounds (the lower $IC_{50}$ the higher binding affinity). The receptor efficacy is defined as the ability to stimulate cAMP production compared to a full agonist as αMSH or NDP-αMSH. Both with regard to maximal efficacy ($E_{max}$) and with regard to the efficacy constant $EC_{50}$, defined as the concentration of agonist given ½ max response (the lower $EC_{50}$ the higher efficacy).

The test compounds of the examples include:

1)
αMSH(Ac-Tyr-Ser-Met-Glu-His-Phe-Arg-Trp-Gly-Lys-Pro-Val-NH₂)(Ac-SEQ ID NO: 2);

2)
NDP-αMSH(Ac-Ser-Tyr-Ser-Nle-Glu-His-(D-Phe)-Arg-Trp-Gly-Lys-Pro-Val-NH₂);

3)
Ac(Lys)₆-αMSH(Ac(Lys)₆-Ser-Tyr-Ser-Met-Glu-His-Phe-Arg-Trp-Gly-Lys-Pro-Val-NH₂) (Ac(Lys)₆-SEQ ID NO: 2);
and 4)
Ac(Lys)₆-NDP-αMSH(Ac(Lys)₆-Ser-Tyr-Ser-Nle-Glu-His-(D-Phe)-Arg-Trp-Gly-Lys-Pro-Val-NH₂).

5)
α-MSH analogue #1:
Ac-(Ac-Lys-Lys-)Lys-Ser-Tyr-Ser-Met-Glu-His-Phe-ArgTrp-Gly-Lys-Pro-Val-NH₂ (Ac-(Ac-Lys-Lys-)Lys-SEQ ID NO: 2), 6) γ-MSH analogue #2:
Ac-(Ac-Lys-Lys-)Lys-Tyr-Val-Met-Gly-His-Phe-Arg-(D-Trp)-Asp-Arg-Phe-Gly-NH₂.

Experimental Set-Up
Test 1) Binding Affinity Against the Human MC1r

Binding affinity against the human MC1r was tested using a radioligand binding assay with membrane fraction of CRO cells stably expressing the human MC1r. Competition binding were performed in the wells of a 96 well plate (Master Block, Greiner, 786201) containing binding buffer, humane MC1r membrane extracts, [125I](Lys11)(Nle4-D-Phe7)-a-MSH and test compound at increasing concentrations. The samples were incubated in a final volume of 0.1 ml for 60 min at 25° C. and then filtered over filters. Filters were washed six times with 0.5 ml of ice-cold washing buffer and 50 μl of Microscint 20 (Packard) are added in each well. The plates were incubated 15 min on an orbital shaker and then counted with a TopCount gamma counter for 1 min/well.

Data is presented as mean values. The inhibition constant is determined by best fit analyses after logarithmic transformation using the graph pad software (version 6.0). Differences are considered significant at probability levels (p) of 0.05.

Test 2) Receptor Efficacy Against the Human MC1r and MC3r

CHO-K1 cells expressing either the MC1r or the MC3r grown in media without antibiotic were detached by gentle flushing with PBS-EDTA (5 mM EDTA), recovered by centrifugation and resuspended in assay buffer (KRH: 5 mM KCl, 1.25 mM MgSO4, 124 mM NaCl, 25 mM HEPES, 13.3 mM Glucose, 1.25 mM KH2PO4, 1.45 mM CaCl2, 0.5 g/l BSA).

12 µl of cells were mixed with 12 µl of the test compound at increasing concentrations in 96 wells plates and then incubated 30 min at room temperature, cAMP production was determined after addition of a lysis buffer and 1 hour incubation, by use of competitive immunoassay using cryptate-labeled anti-cAMP and d2-labeled cAMP (HTRF kit from CisBio) with Delta F percentage values calculated according to the manufacturer specification. Dose response curves were performed in parallel with test compounds, and reference compounds.

The HTRF technology is a titration assay based on a competition between labeled cAMP (exogenous) and cAMP produced by the cell after activation of the MCr. The dynamic range of the assay was 3-4 fold meaning that the linear range (which enables conversion from raw data to nM of cAMP) is within that range. The window between top and bottom of the curve is higher (around 100) which means that converting into nM of cAMP, the assay window of cAMP goes from 1 nM (basal) to around 30 nM (Emax). All experiments were conducted in the presence of the non-selective phosphodiesterase inhibitor IBMX (1 mM in final concentration).

Data is presented as mean values. The inhibition constant is determined by best fit analyses after logarithmic transformation using the graph pad software (version 6.0). Differences are considered significant at probability levels (p) of 0.05.

Test 3) Receptor Efficacy Against the Human MC1r

Alternatively MCR1 receptor efficacy was tested in stably transfected HEK cells expressing the human MC1r. Cells were grown in Dulbecco's modified Eagle's medium 1885 supplemented with 10% fetal calf serum, 2 mm glutamine, and 0.01 mg/ml gentamicin. The expression plasmids containing the cDNAs encoding the wild-type or the mutated receptors were expressed after transfection according to the calcium phosphate precipitation method. The cells were kept frozen until the experiments where the cells was grown in RPMI 1640 medium supplemented with 2 mm I-glutamine adjusted to contain 1.5 g/liter sodium bicarbonate, 4.5 g/liter glucose, 10 mm HEPES, 1.0 mm sodium pyruvate, and 10% fetal bovine serum.

Cells (2.5×105 cells per well) were incubated for 15 min at 37° C. in 1 ml of freshly prepared binding buffer supplemented with 5.10-4 M of the non-specific phosphodiesterase inhibitor 3-Isobutyl-1-methylxanthine (IBMX), 40 µg/ml bacitracin, and various concentrations of test compound. After incubation, cells were placed on ice, medium was removed, and cells lysed. Measurement of cAMP in the samples was conducted by use of a commercial cAMP Enzyme Immunoassay kit from Cayman Chemicals (Cat. No 581001). All cAMP concentrations were expressed relative to the total number of cells in the individual samples.

Example 1

The test compound is α-MSH analogue #1:

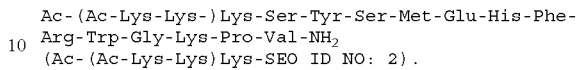

Ac-(Ac-Lys-Lys-)Lys-Ser-Tyr-Ser-Met-Glu-His-Phe-Arg-Trp-Gly-Lys-Pro-Val-NH$_2$
(Ac-(Ac-Lys-Lys)Lys-SEQ ID NO: 2).

Thus, X (or the branched amino acid probe BAP) in this analogue is Ac-(Ac-Lys-Lys-)Lys (see e.g. FIG. 7), which is coupled to the N-terminal Ser of native α-MSH Ser-Tyr-Ser-Met-Glu-His-Phe-Arg-Trp-Gly-Lys-Pro-Val-NH2 amidated at the C-terminus.

Analogue #1 was tested as outlined:
Test 1:

α-MSH analogue #1, α-MSH and Ac(Lys)$_6$-αMSH were examined. The α-MSH analogue #1 and Ac(Lys)$_6$-αMSH were tested in a concentration range from $10^{-6}$ to 10–13 M (n=2-4 at each concentration); α-MSH was tested in the concentration range from $10^{-6}$ to $10^{-11}$ M (n=2 at each concentration).

The results are shown in FIG. 1. The IC$_{50}$ for the α-MSH analogue #1 is calculated as $6.45 \times 10^{-11}$, and the IC$_{50}$ for reference α-MSH is calculated as $4.095 \times 10^{-10}$. No conclusive data could be obtained for Ac(Lys)$_6$-αMSH.

Test 3.

The compounds Ac(Lys)$_6$.αMSH, Ac(Lys)$_6$-NDP-αMSH and αMSH were tested in dose range of $10^{-1}$ to $10^{-6}$ M (n=5-6 at each concentration).

Figure 2:
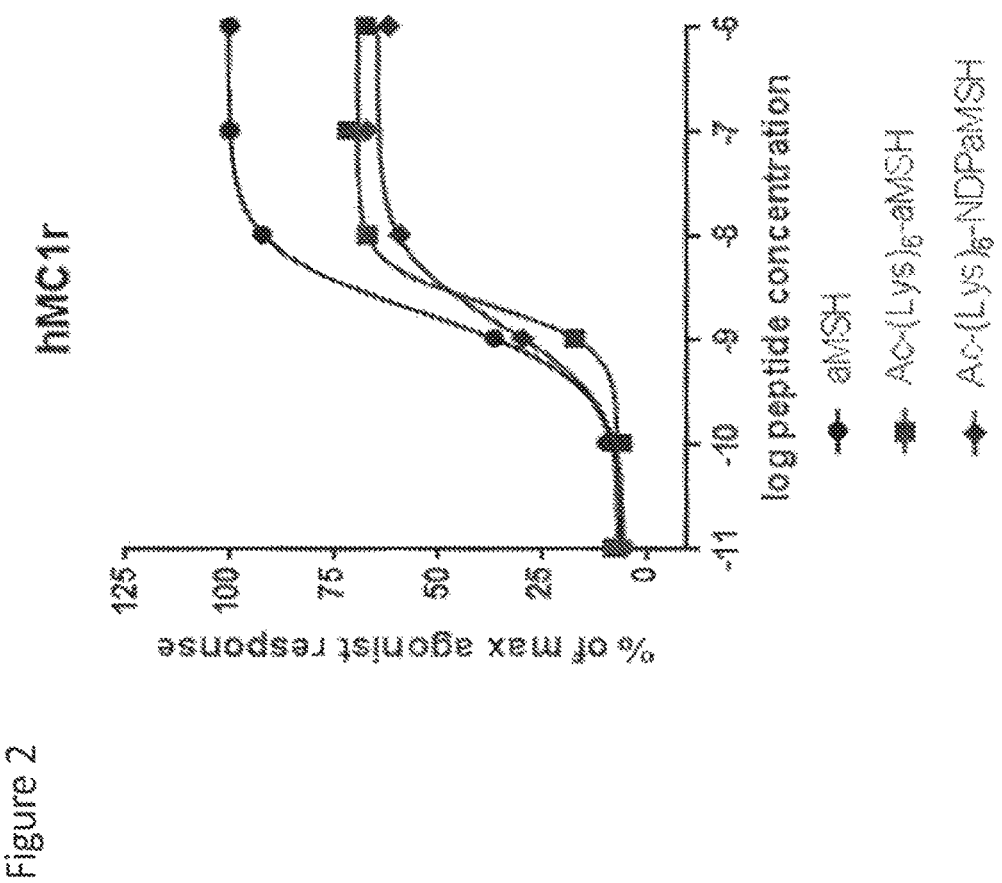
FIG. 2: Receptor efficacy against the human MC1r of the compounds Ac(Lys)₆, αMSH, Ac(Lys)₆-NDP-αMSH and αMSH (See Example 1).

The results are shown in FIG. 2. The maximal efficacy E$_{Max}$ (max efficacy expressed as percent of αMSH) was calculated:

Ac(Lys)$_6$-αMSH E$_{max}$: 72±5% of αMSH, p<0,05;

Ac-(Lys)$_6$-NDP-MSH: E$_{max}$: 62±8% of αMSH, p<0,05.

Also, the EC$_{50}$ values were calculated:

αMSH: $1.74 \times 10^{-9}$ M

Ac(Lys)$_6$-αMSH: $2.12 \times 10^{-9}$ M

Ac(Lys)$_6$-NDP-αMSH: $1.35 \times 10^{-9}$ M.

Test 2:

α-MSH analogue #1, NDP-αMSH (Ac-Ser-Tyr-Ser-Nle Glu-His-(D-Phe)-Arg-Trp-Gly-Lys-Pro-Val-NH2) And Ac(Lys)$_6$-αMSH were tested against the human MC1r. NDP-αMSH is from the literature known as a highly efficient full agonist against MC1r with an EC$_{50}$ reported to be ~10 times lower than αMSH.

α-MSH analogue #1 and Ac(Lys)$_6$-αMSH were tested in a concentration range from $10^{-6}$ to $10^{-11}$ M (n=2 at each concentration); NDP-α-MSH was tested in a concentration range from $10^{-6}$ to $10^{-13}$ M (n=2 at each concentration).

Figure 3:
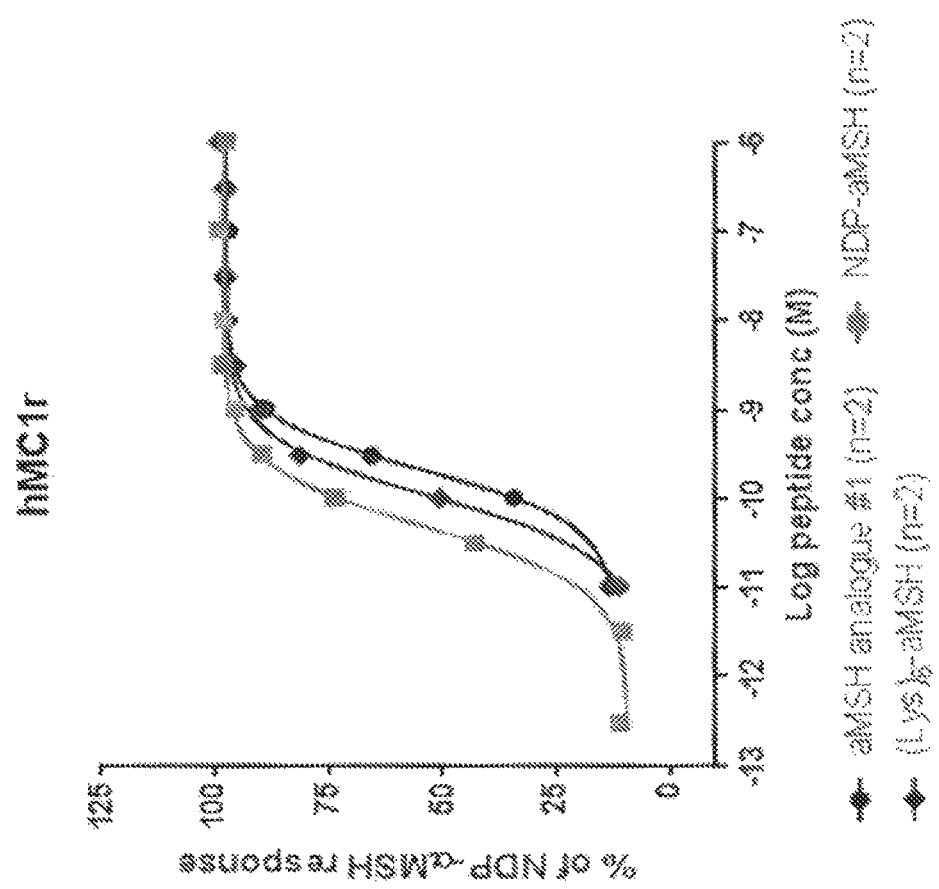
FIG. 3: Receptor efficacy against the human MC1r of α-MSH analogue #1: Ac-(Ac-Lys-Lys-)Lys-Ser-Tyr-Ser-Met-Glu-His-Phe-Arg-Trp-Gly-Lys-Pro-Val-NH2 (Ac-(Ac-Lys-Lys-)Lys- SEQ ID NO:2), NDP-αMSH and Ac(Lys)₆.αMSH (See Example 1).

The results are shown in FIG. 3. The maximal efficacy (E$_{max}$) for both α-MSH analogue #1, NDP-αMSH and Ac(Lys)$_6$-αMSH was ~3 nM. The ECs was $2.0 \times 10^{-10}$ and $4.7 \times 10^{-11}$ M for α-MSH analogue #1 and NDP-αMSH, respectively.

Example 2

The test compound is γ-MSH analogue #2:

Ac-(Ac-Lys-Lys-)Lys-Tyr-Val-Met-Gly-His-Phe-Arg-
(D-Trp)-Asp-Arg-Phe-Gly-NH2.

Thus, X (or the branched amino acid probe BAP) in this compound is Ac-(Ac-Lys-Lys-)Lys (see e.g. FIG. 7), which is coupled to the N-terminal Tyr of γ-MSH Tyr-Val-Met-Gly-His-Phe-Arg-(D-Trp)-Asp-Arg-Phe-Gly-NH2 amidated at the C-terminus, and with the Trp in the D-conformation.

Analogue #2 was tested as outlined:

Test 1:

γ-MSH analogue #2 and NDP-αMSH were tested. NDP-αMSH is from the literature known as highly potent agonist against MC1r with an $IC_{50}$ reported to be ~10 times lower than αMSH. γ-MSH analogue #2 was tested in a concentration range from $10^{-8}$ to $10^{-13}$ M (n=2 at each concentration); NDP-α-MSH was tested in a concentration range from $10^{-6}$ to $10^{-12}$ M (n=3-4 at each concentration).

Figure 4:
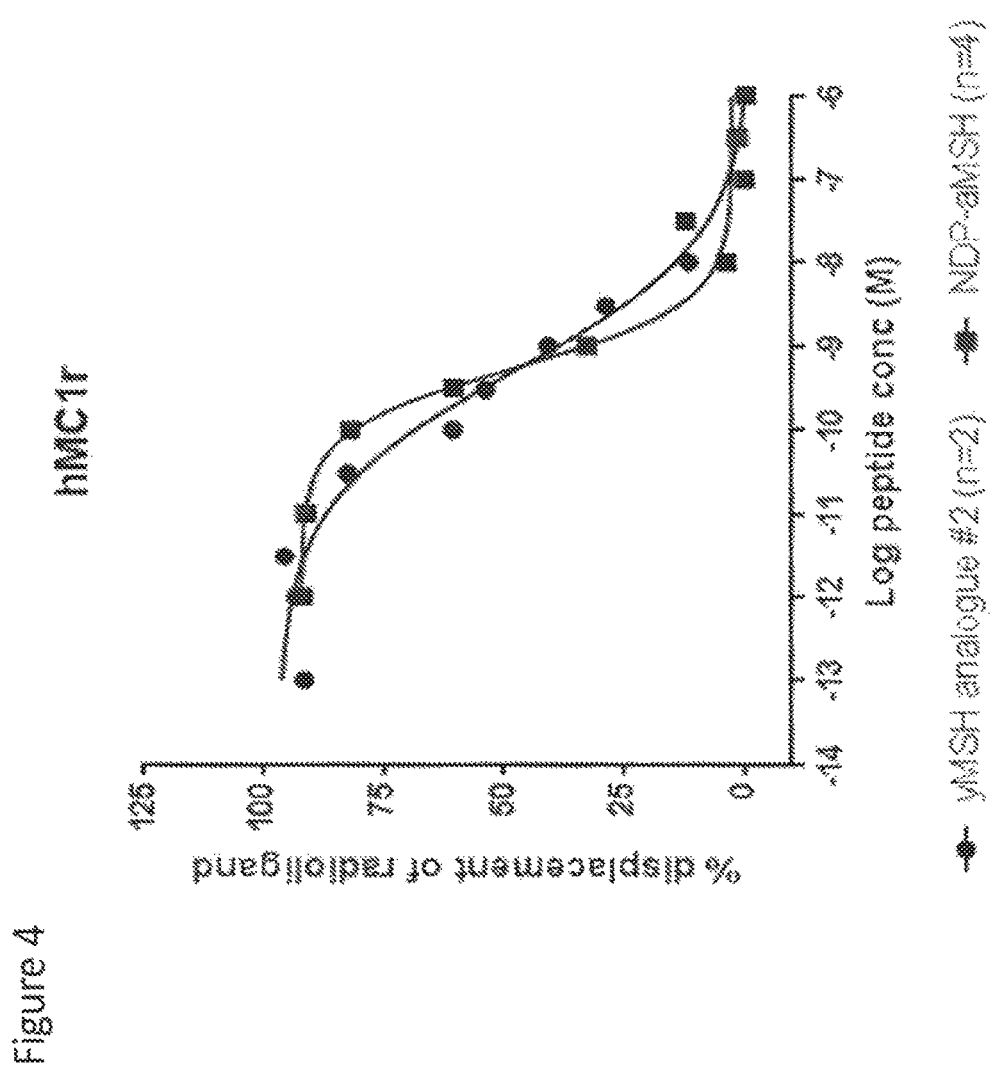
FIG. 4: Binding affinity against the human MC1r and MC3r of γ-MSH analogue #2: Ac-(Ac-Lys-Lys-)Lys-Tyr-Val-Met-Gly-His-Phe-Arg-(D-Trp)-Asp-Arg-Phe-Gly-NH2 (D-Trp version of SEQ ID NO:8) and NDP-αMSH (See Example 2).

The results are shown in FIG. 4. Generally, γ-MSH are known to have weak binding affinity against the human MC1r. The $IC_{50}$ for γ-MSH analogue #2 was calculated as $6.06 \times 10^{-10}$, and the $IC_{50}$ for NDP-αMSH calculated as $5.53 \times 10^{-10}$; thus the binding affinity of γ-MSH analogue #2 is comparable to the superpotent NDP-αMSH.

Test 2:

γ-MSH analogue #2 and NDP-αMSH were tested for agonist activity against the human MC1r and MC3r. NDP-αMSH is from the literature known as a highly efficient full agonist against of both the MC1r and MC3r and is superior to native α-MSH for both the human MC1r and MC3r (~10 times higher potency at both receptors). NDP-αMSH is also more than 100 times more potent than γ-MSH against the human MC1r and MC3r.

For both receptors, γ-MSH analogue #2 was tested in a concentration range from $10^{-6}$ to $10^{-11}$ M (n=2 at each concentration) and NDP-α-MSH was tested in a concentration range from $10^{-5}$ to $3 \times 10^{-13}$ M (n=2 at each concentration).

Figure 5:
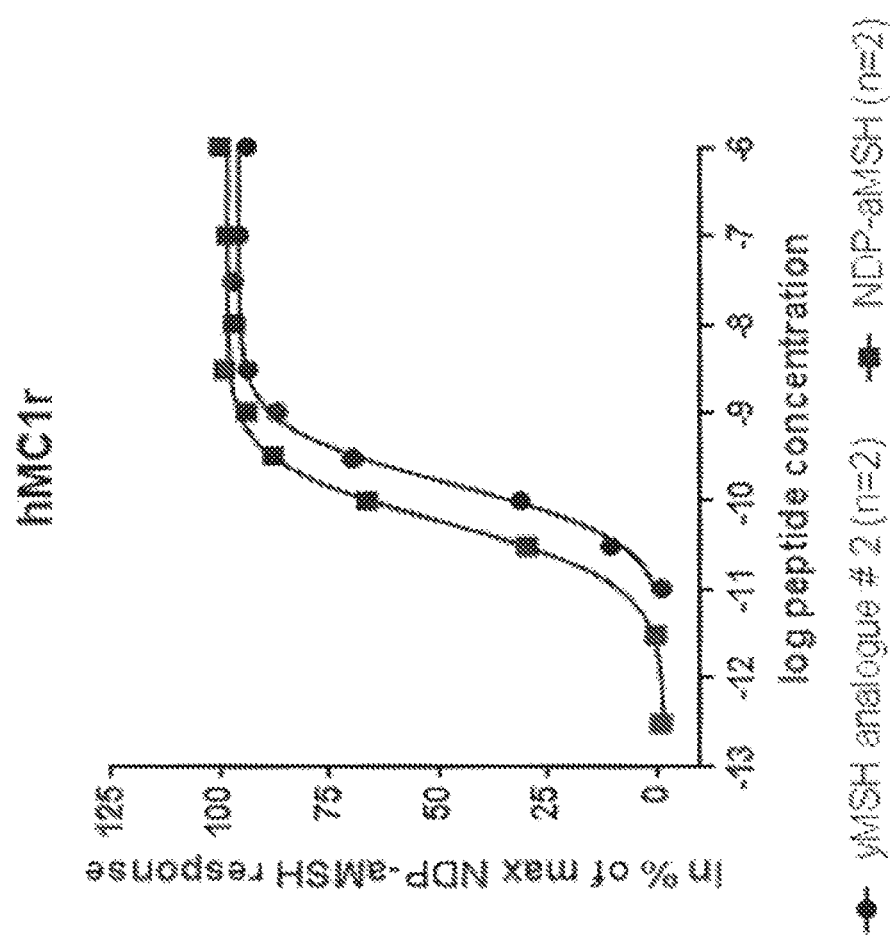
FIG. 5: Receptor efficacy against the human MC1r and MC3r of γ-MSH analogue #2 (See Example 2).
Figure 6:
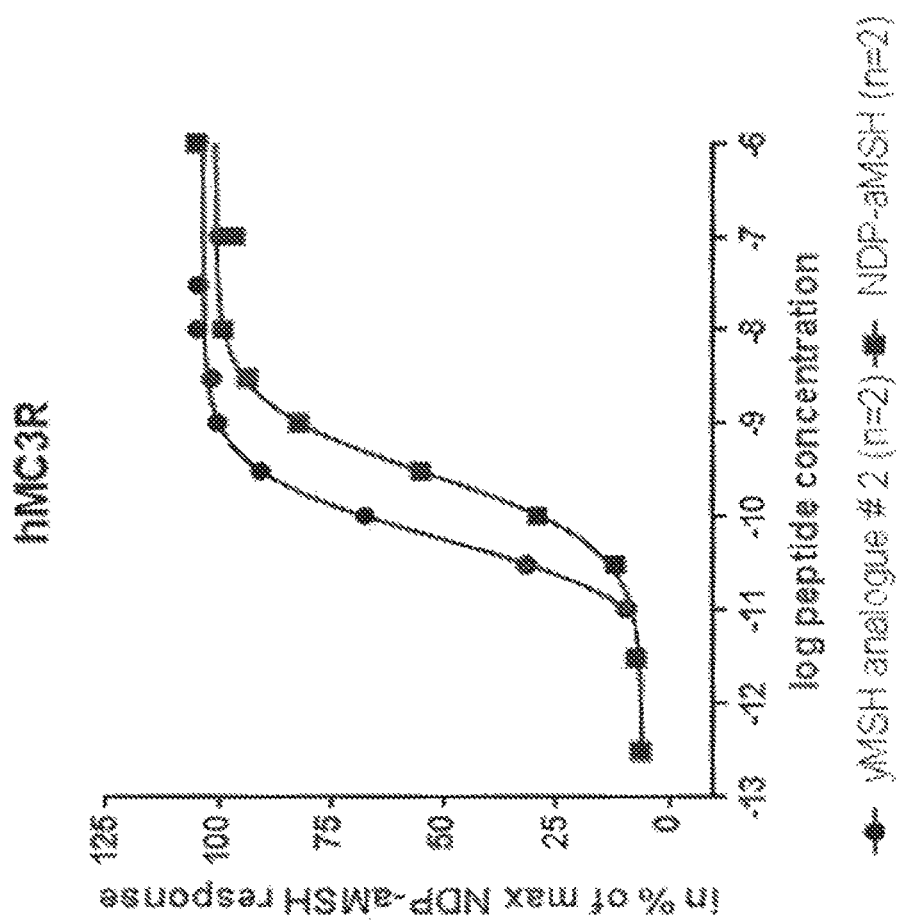
FIG. 6: Receptor efficacy against the human MC1r and MC3r of γ-MSH analogue #2 (See Example 2).

The results are shown in FIGS. 5 and 6:

For γ-MSH analogue #2 against the human MC1r; $E_{max}$~10 nM and $EC_{50}$ of $1.52 \times 10^{-10}$.

For NDP-αMSH against the human MC1r the values Emax~3 nM and $EC_{50}$ of $5.5 \times 10^{-11}$ (see FIG. 5).

For γ-MSH analogue #2 against the human MC3r; $E_{max}$~1 nM and $EC_{50}$ of $5.65 \times 10^{-11}$ M. For NDP-αMSH against the human MC3r $E_{max}$~10 nM and $EC_{50}$ $2.80 \times 10^{-10}$ M (see FIG. 6).

Example 3

Synthesis of the Peptides of Examples 1 and 2:
α-MSH Analogue #1:

Ac-(Ac-Lys-Lys-)Lys-Ser-Tyr-Ser-Met-Glu-His-Phe-
Arg-Trp-Gly-Lys-Pro-Val-NH2
(Ac-(Ac-Lys-Lys)Lys-SEQ ID NO: 2).

γ-MSH Analogue #2:

Ac-(Ac-Lys-Lys-)Lys-Tyr-Val-Met-Gly-His-Phe-Arg-
(D-Trp)-Asp-Arg-Phe-Gly-NH2.

The peptides are manufactured using Fmoc (9-fluorenyl-methyloxycarbonyl) chemistry. Peptides are made using a polystyrene resin, functionalized with an appropriate linker, and the peptides are then manufactured using an Intavis Peptide Synthesizer. A 4-fold excess of amino acid is added relative to the resin and either HATU (O-(7-azabenzotriazol-1-yl)-N,N,N',N'-tetramethyluronium hexafluorophosphate) or HCTU (2-(6-Chloro-1H-benzotriazole-1-yl)-1,1,3,3-tetramethylaminium hexafluorophosphate) were used at a 3.95-fold excess to create the active ester. Along with an 8-fold excess of DIPEA (N,N-Diisopropylethylamine) as the base, these reagents catalyze the addition of the next amino acid. Once the amino acid is coupled (each cycle includes a double coupling cycle to insure efficient coupling) the resin is exposed to 20% acetic anhydride to terminate ("cap-off") any peptide chains that have not added the next amino acid.

The amino acids are dissolved in NMP (N-Methyl-2-pyrrolidone) or DMF (Dimethylformamide) For washing. Piperidine is used to remove the Fmoc group at the end of each coupling cycle which allows the next amino acid to be added.

α-MSH analogue #1 was made with Lys(Mtt) on the end; the peptide was acetylated, the Mtt was removed, added Lys, added Lys and then acetylate again.

For γ-MSH analogue #2 the addition of one or more pseudoproline (oxazolidine) dipeptides during the synthesis of serine- and/or threonine-containing peptides resulted in improvements in peptide quality and an increase in the yield of full length crude peptide. In this case the peptide was made up to the MEHF, a pseudoproline dipeptide (Fmoc-YS) was added, the next amino acid "Ser" was coupled 3 times to insure it went to completion, and the peptide finished manually by adding the Lys(Mtt), acetylating, and then finishing as above.

In each case the peptides were dried using MeOH (3×), DCM (3×), cleaved using 92% TFA, 2% water, 2% triisopropylsilane, 2% thioanisole and 2% ethanedithiol for 3-4 h at room temperature. Peptides were precipitated in cold diethyl ether, centrifuged (2,000 RPM) and the pellets washed 2× with cold ether. After drying the peptides were solubilized in water containing 0.1% TFA (buffer A) and subjected to RP-HPLC using C18 columns (buffer B=95% acetonitrile/0.1% TFA).

The purity was determined by analytical HPLC and theoretical mono isotopic molecular masses we confirmed by MS. The sequence integrity was verified by CID tandem MS/MS sequencing.

The invention claimed is:

1. A peptide comprising the amino acid sequence:

$$X\text{-}(aa_1)_n\text{-}Y\text{-}(aa_2)_m\text{-}Z$$

wherein X consists of a branched amino acid probe (BAP) consisting of 2 to 9 amino acid residues, wherein the branch point of the BAP is formed by an amide bond between the ε-amino group of one amino acid residue with the carboxyl group of another amino acid residue, all other bonds being regular peptide bonds, including the bond to $(aa_1)_n$, and wherein one or more alpha amino groups of X are optionally acetylated;

$(aa_1)_n$ is selected from the group consisting of Ser-Tyr-Ser-Met-Glu (SEQ ID NO: 17), Ser-Tyr-Ser-Nle-Glu (SEQ ID NO: 18), Ser-Ser-Ile-Ile-Ser (SEQ ID NO: 19), Tyr-Val-Met-Gly (SEQ ID NO:20) and Tyr-Val-Nle-Gly (SEQ ID NO:21); n is 1, 2, 3, 4 or 5;

Y is selected from the group consisting of His-Phe-Arg-Trp (SEQ ID NO: 16), His-(D-Phe)-Arg-Trp, His-Phe-(D-Arg)-Trp, His-Phe-Arg-(D-Trp), His-(D-Phe)-Arg-(D-Trp), His-Nal-Arg-Trp and His-(D-Nal)-Arg-Trp;

$(aa_2)_m$ is Gly, Asp, or is absent; m is 0 or 1; and

Z is selected from the group consisting of Lys-Pro-Val; Lys-Pro-(D-Val); Arg-Phe-Gly; Arg-(D-Phe)-Gly; Arg-Phe and Arg-(D-Phe);

wherein the C-terminal carboxylic group is optionally an amide (—NH$_2$) or a pharmaceutically acceptable ester, or a pharmaceutically acceptable salt thereof.

2. The peptide according to claim 1, wherein X comprises a first lysine residue selected from Lys and D-Lys linked by a regular peptide bond to $(aa_1)_n$, and optionally further comprising a second lysine residue, or a second and third lysine residue, via regular peptide bonds, wherein the branch point is formed by an amide bond between the ε-amino group of one or more of said lysine residues with the carboxyl group of another amino acid residue.

3. The peptide according to claim 2, wherein the branch point is formed by an amide bond between the ε-amino group of one or more of said lysine residues with the carboxyl group of an amino acid residue selected from the group consisting of: Ac-Lys$_q$-Lys; Ac-$(aa_3)_p$-Lys$_q$; Ac-Lys$_q$-$(aa_3)_p$; Ac-[$(aa_3)$-Lys]$_p$ and Ac-[Lys-$(aa_3)$]$_p$, wherein q is a number selected from 0, 1, 2 and 3 and ($aa_3$) is an amino acid residue independently selected from Gly and Ala.

4. The peptide according to claim 2, wherein the branch point is formed by an amide bond between the ε-amino group of one or more of said lysine residues with the carboxyl group of an amino acid residue selected from the group consisting of: Lys, Ac-Lys, Lys-Lys, Ac-Lys-Lys, Lys-Lys-Lys, Ac-Lys-Lys-Lys, Lys-Lys-Lys-Lys, Ac-Lys-Lys-Lys-Lys, Lys-Gly-Lys, Ac-Lys-Gly-Lys, Lys-Lys-Gly, Ac-Lys-Lys-Gly, Lys-Gly, Ac-Lys-Gly, Lys-Ala-Lys, Ac-Lys-Ala-Lys, Lys-Lys-Ala, Ac-Lys-Lys-Ala, Lys-Ala, Ac-Lys-Ala, Lys-His-Lys, Ac-Lys-His-Lys, Lys-Lys-His, Ac-Lys-Lys-His, Lys-His, Ac-Lys-His, Lys-Arg-Lys, Ac-Lys-Arg-Lys, Lys-Lys-Arg, Ac-Lys-Lys-Arg, Lys-Arg and Ac-Lys-Arg, wherein each Lys, Gly, Ala, His and Arg residues may each be in the L- or D-conformation.

5. The peptide according to claim 2, wherein the branch point is formed by an amide bond between the ε-amino group of one or more of said lysine residues with the carboxyl group of another amino acid residue selected from the group consisting of: Lys$_q$-Lys and Ac-Lys$_q$-Lys, wherein q is a number selected from 0, 1, 2 and 3.

6. The peptide according to claim 1, wherein X consisting of 3 amino acid residues comprises an amino acid selected from the group consisting of Arg, His, Gly and Ala.

7. The peptide according to claim 1, wherein X consists of 2, 4, 5, 6, 7, 8 or 9 amino acid residues.

8. The peptide according to claim 7, wherein X consists of 2, 4, 5, 6, 7, 8 or 9 amino acid residues selected from Lys and D-Lys.

9. The peptide according to claim 1, wherein $(aa_1)_n$ is selected from the group consisting of Ser-Tyr-Ser-Met-Glu (SEQ ID NO:17), Ser-Tyr-Ser-Nle-Glu (SEQ ID NO:18), and Ser-Ser-Ile-Ile-Ser (SEQ ID NO:19); Y is selected from the group consisting of His-Phe-Arg-Trp (SEQ ID NO:16); His-(D-Phe)-Arg-Trp; His-Phe-(D-Arg)-Trp; His-Phe-Arg-(D-Trp); His-(D-Phe)-Arg-(D-Trp); His-Nal-Arg-Trp and His-(D-Nal)-Arg-Trp; $(aa_2)_m$ is Gly; and Z is selected from the group consisting of Lys-Pro-Val and Lys-Pro-(D-Val).

10. The peptide according to claim 1, wherein $(aa_1)_n$-Y-$(aa_2)_m$-Z is selected from the group consisting of:

(SEQ ID NO: 1)
Ser-Tyr-Ser-Met-Glu-His-Phe-Arg-Trp-Gly-Lys-Pro-Val,

Ser-Tyr-Ser-Met-Glu-His-(D-Phe)-Arg-Trp-Gly-Lys-Pro-Val,

Ser-Tyr-Ser-Met-Glu-His-Phe-(D-Arg)-Trp-Gly-Lys-Pro-Val

Ser-Tyr-Ser-Met-Glu-His-Phe-Arg-(D-Trp)-Gly-Lys-Pro-Val,

Ser-Tyr-Ser-Met-Glu-His-(D-Phe)-Arg-(D-Trp)-Gly-Lys-Pro-Val,

Ser-Tyr-Ser-Met-Glu-His-Nal-Arg-Trp-Gly-Lys-Pro-Val,

Ser-Tyr-Ser-Met-Glu-His-(D-Nal)-Arg-Trp-Gly-Lys-Pro-Val,

Ser-Tyr-Ser-Met-Glu-His-Phe-Arg-Trp-Gly-Lys-Pro-(D-Val),

Ser-Tyr-Ser-Met-Glu-His-(D-Phe)-Arg-Trp-Gly-Lys-Pro-(D-Val),

Ser-Tyr-Ser-Met-Glu-His-Phe-(D-Arg)-Trp-Gly-Lys-Pro-(D-Val),

Ser-Tyr-Ser-Met-Glu-His-Phe-Arg-(D-Trp)-Gly-Lys-Pro-(D-Val),

Ser-Tyr-Ser-Met-Glu-His-(D-Phe)-Arg-(D-Trp)-Gly-Lys-Pro-(D-Val),

Ser-Tyr-Ser-Met-Glu-His-Nal-Arg-Trp-Gly-Lys-Pro-(D-Val),

Ser-Tyr-Ser-Met-Glu-His-(D-Nal)-Arg-Trp-Gly-Lys-Pro-(D-Val), (SEQ ID NO: 3)
Ser-Tyr-Ser-Nle-Glu-His-Phe-Arg-Trp-Gly-Lys-Pro-Val,

Ser-Tyr-Ser-Nle Glu-His-(D-Phe)-Arg-Trp-Gly-Lys-Pro-Val,

Ser-Tyr-Ser-Nle Glu-His-Phe-(D-Arg)-Trp-Gly-Lys-Pro-Val

Ser-Tyr-Ser-Nle-Glu-His-Phe-Arg-(D-Trp)-Gly-Lys-Pro-Val,

Ser-Tyr-Ser-Nle-Glu-His-(D-Phe)-Arg-(D-Trp)-Gly-Lys-Pro-Val,

Ser-Tyr-Ser-Nle-Glu-His-Nal-Arg-Trp-Gly-Lys-Pro-Val,

Ser-Tyr-Ser-Nle-Glu-His-(D-Nal)-Arg-Trp-Gly-Lys-Pro-Val,

Ser-Tyr-Ser-Nle-Glu-His-Phe-Arg- Trp-Gly-Lys-Pro-(D -Val),

Ser-Tyr-Ser-Nle-Glu-His-(D-Phe)-Arg-Trp-Gly-Lys-Pro-(D-Val),

Ser-Tyr-Ser-Nle-Glu-His-Phe-(D-Arg)-Trp-Gly-Lys-Pro-(D-Val),

Ser-Tyr-Ser-Nle Glu-His-Phe-Arg-(D- Trp)-Gly-Lys-Pro-(D -Val),

Ser-Tyr-Ser-Nle-Glu-His-(D-Phe)-Arg-(D-Trp)-Gly-Lys-Pro-(D-Val),

Ser-Tyr-Ser-Nle-Glu-His-Nal-Arg-Trp-Gly-Lys-Pro-(D-Val),

Ser-Tyr-Ser-Nle-Glu-His-(D-Nal)-Arg-Trp-Gly-Lys-Pro-(D-Val),

-continued (SEQ ID NO: 5)
Ser-Ser-Ile-Ile-Ser-His-Phe-Arg-Trp-Gly-Lys-Pro-Val,

Ser-Ser-Ile-Ile-Ser-His-(D-Phe)-Arg-Trp-Gly-Lys-Pro-Val,

Ser-Ser-Ile-Ile-Ser-His-Phe-(D-Arg)-Trp-Gly-Lys-Pro-Val

Ser-Ser-Ile-Ile-Ser-His-Phe-Arg-(D-Trp)-Gly-Lys-Pro-Val,

Ser-Ser-Ile-Ile-Ser-His-(D-Phe)-Arg-(D-Trp)-Gly-Lys-Pro-Val,

Ser-Ser-Ile-Ile-Ser-His-Nal-Arg-Trp-Gly-Lys-Pro-Val,

Ser-Ser-Ile-Ile-Ser-His-(D-Nal)-Arg-Trp-Gly-Lys-Pro-Val,

Ser-Ser-Ile-Ile-Ser-His-Phe-Arg-Trp-Gly-Lys-Pro-(D-Val),

Ser-Ser-Ile-Ile-Ser-His-(D-Phe)-Arg-Trp-Gly-Lys-Pro-(D-Val),

Ser-Ser-Ile-Ile-Ser-His-Phe-(D-Arg)-Trp-Gly-Lys-Pro-(D-Val),

Ser-Ser-Ile-Ile-Ser-His-Phe-Arg-(D-Trp)-Gly-Lys-Pro-(D-Val),

Ser-Ser-Ile-Ile-Ser-His-(D-Phe)-Arg-(D-Trp)-Gly-Lys-Pro-(D-Val),

Ser-Ser-Ile-Ile-Ser-His-Nal-Arg-Trp-Gly-Lys-Pro-(D-Val),
and

Ser-Ser-Ile-Ile-Ser-His-(D-Nal)-Arg-Trp-Gly-Lys-Pro-(D-Val), wherein said carboxy terminal Val or (D-Val) is optionally a Valine amide (—NH$_2$).

11. The peptide according to claim 1, wherein $(aa_1)_n$-Y-$(aa_2)_m$-Z is selected from the group consisting of:

(SEQ ID NO: 7)
Tyr-Val-Met-Gly-His-Phe-Arg-Trp-Asp-Arg-Phe-Gly,

Tyr-Val-Met-Gly-His-(D-Phe)-Arg-Trp-Asp-Arg-Phe-Gly,

Tyr-Val-Met-Gly-His-Phe-(D-Arg)-Trp-Asp-Arg-Phe-Gly,

Tyr-Val-Met-Gly-His-Phe-Arg-(D-Trp)-Asp-Arg-Phe-Gly,

Tyr-Val-Met-Gly-His-(D-Phe)-Arg-(D-Trp)-Asp-Arg-Phe-Gly,

Tyr-Val-Met-Gly-His-Nal-Arg-Trp-Asp-Arg-Phe-Gly,

Tyr-Val-Met-Gly-His-(D-Nal)-Arg-Trp-Asp-Arg-Phe-Gly,

Tyr-Val-Met-Gly-His-Phe-Arg-Trp-Asp-Arg-(D-Phe)-Gly,

Tyr-Val-Met-Gly-His-(D-Phe)-Arg-Trp-Asp-Arg-(D-Phe)-Gly,

Tyr-Val-Met-Gly-His-Phe-(D-Arg)-Trp-Asp-Arg-(D-Phe)-Gly,

Tyr-Val-Met-Gly-His-Phe-Arg-(D-Trp)-Asp-Arg-(D-Phe)-Gly,

Tyr-Val-Met-Gly-His-(D-Phe)-Arg-(D-Trp)-Asp-Arg-(D-Phe)-Gly,

Tyr-Val-Met-Gly-His-Nal-Arg-Trp-Asp-Arg-(D-Phe)-Gly,

Tyr-Val-Met-Gly-His-(D-Nal)-Arg-Trp-Asp-Arg-(D-Phe)-Gly, (SEQ ID NO: 9)
Tyr-Val-Nle-Gly-His-Phe-Arg-Trp-Asp-Arg-Phe-Gly,

Tyr-Val-Nle-Gly-His-(D-Phe)-Arg-Trp-Asp-Arg-Phe-Gly,

Tyr-Val-Nle-Gly-His-Phe-(D-Arg)-Trp-Asp-Arg-Phe-Gly,

Tyr-Val-Nle-Gly-His-Phe-Arg-(D-Trp)-Asp-Arg-Phe-Gly,

Tyr-Val-Nle-Gly-His-(D-Phe)-Arg-(D-Trp)-Asp-Arg-Phe-Gly,

Tyr-Val-Nle-Gly-His-Nal-Arg-Trp-Asp-Arg-Phe-Gly,

Tyr-Val-Nle-Gly-His-(D-Nal)-Arg-Trp-Asp-Arg-Phe-Gly,

Tyr-Val-Nle-Gly-His-Phe-Arg-Trp-Asp-Arg-(D-Phe)-Gly,

Tyr-Val-Nle-Gly-His-(D-Phe)-Arg-Trp-Asp-Arg-(D-Phe)-Gly,

Tyr-Val-Nle-Gly-His-Phe-(D-Arg)-Trp-Asp-Arg-(D-Phe)-Gly,

Tyr-Val-Nle-Gly-His-Phe-Arg-(D-Trp)-Asp-Arg-(D-Phe)-Gly,

Tyr-Val-Nle-Gly-His-(D-Phe)-Arg-(D-Trp)-Asp-Arg-(D-Phe)-Gly,

Tyr-Val-Nle-Gly-His-Nal-Arg-Trp-Asp-Arg-(D-Phe)-Gly,

Tyr-Val-Nle-Gly-His-(D-Nal)-Arg-Trp-Asp-Arg-(D-Phe)-Gly, (SEQ ID NO: 11)
Tyr-Val-Met-Gly-His-Phe-Arg-Trp-Asp-Arg-Phe,

Tyr-Val-Met-Gly-His-(D-Phe)-Arg-Trp-Asp-Arg-Phe,

Tyr-Val-Met-Gly-His-Phe-(D-Arg)-Trp-Asp-Arg-Phe,

Tyr-Val-Met-Gly-His-Phe-Arg-(D-Trp)-Asp-Arg-Phe,

Tyr-Val-Met-Gly-His-(D-Phe)-Arg-(D-Trp)-Asp-Arg-Phe,

Tyr-Val-Met-Gly-His-Nal-Arg-Trp-Asp-Arg-Phe,

Tyr-Val-Met-Gly-His-(D-Nal)-Arg-Trp-Asp-Arg-Phe,

Tyr-Val-Met-Gly-His-Phe-Arg-Trp-Asp-Arg-(D-Phe),

Tyr-Val-Met-Gly-His-(D-Phe)-Arg-Trp-Asp-Arg-(D-Phe),

Tyr-Val-Met-Gly-His-Phe-(D-Arg)-Trp-Asp-Arg-(D-Phe),

Tyr-Val-Met-Gly-His-Phe-Arg-(D-Trp)-Asp-Arg-(D-Phe),

-continued

Tyr-Val-Met-Gly-His-(D-Phe)-Arg-(D-Trp)-Asp-Arg-(D-Phe),

Tyr-Val-Met-Gly-His-Nal-Arg-Trp-Asp-Arg-(D-Phe),

Tyr-Val-Met-Gly-His-(D-Nal)-Arg-Trp-Asp-Arg-(D-Phe), (SEQ ID NO: 13)
Tyr-Val-Nle-Gly-His-Phe-Arg-Trp-Asp-Arg-Phe,

Tyr-Val-Nle-Gly-His-(D-Phe)-Arg-Trp-Asp-Arg-Phe,

Tyr-Val-Nle-Gly-His-Phe-(D-Arg)-Trp-Asp-Arg-Phe,

Tyr-Val-Nle-Gly-His-Phe-Arg-(D-Trp)-Asp-Arg-Phe,

Tyr-Val-Nle-Gly-His-(D-Phe)-Arg-(D-Trp)-Asp-Arg-Phe,

Tyr-Val-Nle-Gly-His-Nal-Arg-Trp-Asp-Arg-Phe,

Tyr-Val-Nle-Gly-His-(D-Nal)-Arg-Trp-Asp-Arg-Phe,

Tyr-Val-Nle-Gly-His-Phe-Arg-Trp-Asp-Arg-(D-Phe),

Tyr-Val-Nle-Gly-His-(D-Phe)-Arg-Trp-Asp-Arg-(D-Phe),

Tyr-Val-Nle-Gly-His-Phe-(D-Arg)-Trp-Asp-Arg-(D-Phe),

Tyr-Val-Nle-Gly-His-Phe-Arg-(D-Trp)-Asp-Arg-(D-Phe),

Tyr-Val-Nle-Gly-His-(D-Phe)-Arg-(D-Trp)-Asp-Arg-(D-Phe),

Tyr-Val-Nle-Gly-His-Nal-Arg-Trp-Asp-Arg-(D-Phe), and

Tyr-Val-Nle-Gly-His-(D-Nal)-Arg-Trp-Asp-Arg-(D-Phe).

wherein said carboxy terminal Phe or (D-Phe) is optionally a Phenylalanine amide (—NH$_2$), and/or wherein said carboxy terminal Gly is optionally Glycine amide (—NH$_2$).

12. The peptide according to claim 1, wherein said peptide is capable of binding to and activating melanocortin receptors MC1r and/or MC3r.

13. A pharmaceutical composition comprising one or more peptides according to claim 1, or pharmaceutically acceptable salts thereof, and a pharmaceutically acceptable carrier.

14. The peptide according to claim 1, wherein (aa1)n is Tyr-Val-Met-Gly (SEQ ID NO:20) or Tyr-Val-Nle-Gly (SEQ ID NO:21); Y is His-Phe-Arg-Trp (SEQ ID NO:16); His-(D-Phe)-Arg-Trp; His-Phe-(D-Arg)-Trp; His-Phe-Arg-(D-Trp); His-(D-Phe)-Arg-(D-Trp); His-Nal-Arg-Trp or His-(D-Nal)-Arg-Trp; (aa2)m is Asp and Z is selected from the group consisting of Arg-Phe-Gly; Arg-(D-Phe)-Gly; Arg-Phe and Arg-(D-Phe).

15. The peptide according to claim 1, wherein X is selected from the group consisting of:
Ac-(Ac-Lys)Lys1-, Ac-(Ac-Lys-Lys)Lys1-, Ac-(Ac-Lys-Lys-Lys)Lys1-, Ac-(Ac-Lys-Lys-Lys-Lys)Lys1-, Ac-(Ac-Lys-Gly-Lys)Lys1-, Ac-(Ac-Lys-Lys-Gly)Lys1-, Ac-(Ac-Lys-Gly)Lys1-, Ac-(Ac-Lys-Ala-Lys)Lys1-, Ac-(Ac-Lys-Lys-Ala)Lys1-, Ac-(Ac-Lys-Ala)Lys1-, Ac-(Ac-Lys-His-Lys)Lys1-, Ac-(Ac-Lys-Lys-His) Lys1-, Ac-(Ac-Lys-His)Lys1-, Ac-(Ac-Lys-Arg-Lys) Lys1-, Ac-(Ac-Lys-Lys-Arg)Lys1-, and Ac-(Ac-Lys-Arg)Lys1-;

Ac-(Ac-Lys)Lys2-Lys1-, Ac-(Ac-Lys-Lys)Lys2-Lys1-, Ac-(Ac-Lys-Gly)Lys2-Lys1-, Ac-(Ac-Lys-Lys-Lys) Lys2-Lys1-, Ac-(Ac-Lys-Lys-Lys-Lys)Lys2-Lys1-, Ac-Lys2-(Ac-Lys)-Lys1-, Ac-Lys2-(Ac-Lys-Lys)-Lys1-, Ac-Lys2-(Ac-Lys-Gly)-Lys1-, Ac-Lys2-(Ac-Lys-Lys-Lys)-Lys1-, Ac-Lys2-(Ac-Lys-Lys-Lys-Lys)-Lys1-, Ac-(Ac-Lys)Lys2-(Ac-Lys-)-Lys1-, Ac-(Ac-Lys)Lys2-(Ac-Lys-Lys-)-Lys1-, and Ac-(Ac-Lys-Lys) Lys2-(Ac-Lys-Lys-)-Lys1-;

Ac-Lys3-Lys2-(Ac-Lys)Lys1-, Ac-Lys3-(Ac-Lys)Lys2-Lys1-, Ac-(Ac-Lys)Lys3-Lys2-Lys1-, Ac-Lys3-(Ac-Lys)Lys2-(Ac-Lys)Lys1-, Ac-(Ac-Lys)Lys3-(Ac-Lys) Lys2-Lys1-, and Ac-(Ac-Lys)Lys3-Lys2-(Ac-Lys) Lys1-; and Ac-(Ac-Lys)Lys-Lys-, Ac-(Ac-Lys-Lys)Lys-, and Ac-Lys-(Ac-Lys)Lys-.

16. The peptide according to claim 1, wherein said peptide is selected from the group consisting of:
Ac-(Ac-Lys-Lys)Lys-Ser-Tyr-Ser-Met-Glu-His-Phe-Arg-Trp-Gly-Lys-Pro-Val-NH$_2$;

Ac-(Ac-Lys-Lys)Lys-Ser-Tyr-Ser-Met-Glu-His-Phe-Arg-Trp-Gly-Lys-Pro-(D-Val)-NH$_2$;

Ac-(Ac-Lys-Lys)Lys-Ser-Tyr-Ser-Nle-Glu-His-(D-Phe)-Arg-Trp-Gly-Lys-Pro-Val-NH$_2$;

Ac-(Ac-Lys-Lys)Lys-Tyr-Val-Met-Gly-His-Phe-Arg-(D-Trp)-Asp-Arg-Phe-Gly-NH$_2$;

Ac-(Ac-Lys-Lys)Lys-Tyr-Val-Met-Gly-His-Phe-Arg-Trp-Asp-Arg-Phe-Gly-NH$_2$;

Ac-(Ac-Lys-Lys)Lys-Tyr-Val-Met-Gly-His-(D-Phe)-Arg-(D-Trp)-Asp-Arg-Phe-Gly-NH$_2$;

Ac-(Ac-Lys-Lys)Lys-Tyr-Val-Met-Gly-His-Phe-Arg-(D-Trp)-Asp-Arg-(D-Phe)-Gly-NH$_2$;

Ac-(Ac-Lys-Lys)Lys-Tyr-Val-Nle-Gly-His-Phe-Arg-(D-Trp)-Asp-Arg-Phe-Gly-NH$_2$;

Ac-(Ac-Lys-Lys)Lys-Tyr-Val-Nle-Gly-His-Phe-Arg-Trp-Asp-Arg-Phe-Gly-NH$_2$;

Ac-(Ac-Lys-Lys)Lys-Tyr-Val-Nle-Gly-His-(D-Phe)-Arg-Trp-Asp-Arg-Phe-Gly-NH$_2$;

Ac-(Ac-Lys-Lys)Lys-Tyr-Val-Nle-Gly-His-(D-Phe)-Arg-(D-Trp)-Asp-Arg-Phe-Gly-NH$_2$;

Ac-(Ac-Lys-Lys)Lys-Lys-Ser-Tyr-Ser-Met-Glu-His-Phe-Arg-Trp-Gly-Lys-Pro-Val-NH$_2$;

Ac-(Ac-Lys-Lys)Lys-Lys-Ser-Tyr-Ser-Met-Glu-His-Phe-Arg-Trp-Gly-Lys-Pro-(D-Val)-NH$_2$;

Ac-(Ac-Lys-Lys)Lys-Lys-Ser-Tyr-Ser-Nle-Glu-His-(D-Phe)-Arg-Trp-Gly-Lys-Pro-Val-NH$_2$;

Ac-(Ac-Lys-Lys)Lys-Lys-Tyr-Val-Met-Gly-His-Phe-Arg-(D-Trp)-Asp-Arg-Phe-Gly-NH$_2$;

Ac-(Ac-Lys-Lys)Lys-Lys-Tyr-Val-Met-Gly-His-Phe-Arg-Trp-Asp-Arg-Phe-Gly-NH$_2$;

Ac-(Ac-Lys-Lys)Lys-Lys-Tyr-Val-Met-Gly-His-(D-Phe)-Arg-(D-Trp)-Asp-Arg-Phe-Gly-NH$_2$;

Ac-(Ac-Lys-Lys)Lys-Lys-Tyr-Val-Met-Gly-His-Phe-Arg-(D-Trp)-Asp-Arg-(D-Phe)-Gly-NH$_2$;

Ac-(Ac-Lys-Lys)Lys-Lys-Tyr-Val-Nle-Gly-His-Phe-Arg-(D-Trp)-Asp-Arg-Phe-Gly-NH$_2$;

Ac-(Ac-Lys-Lys)Lys-Lys-Tyr-Val-Nle-Gly-His-Phe-Arg-Trp-Asp-Arg-Phe-Gly-NH$_2$;

Ac-(Ac-Lys-Lys)Lys-Lys-Tyr-Val-Nle-Gly-His-(D-Phe)-Trp-Asp-Arg-Phe-Gly-NH$_2$;

Ac-(Ac-Lys-Lys)Lys-Lys-Tyr-Val-Nle-Gly-His-(D-Phe)-(D-Trp)-Asp-Arg-Phe-Gly-NH$_2$;

Ac-Lys-(Ac-Lys)Lys-Ser-Tyr-Ser-Met-Glu-His-Phe-Arg-Trp-Gly-Lys-Pro-Val-NH$_2$;

Ac-Lys-(Ac-Lys)Lys-Ser-Tyr-Ser-Met-Glu-His-Phe-Arg-Trp-Gly-Lys-Pro-(D-Val)-NH$_2$;

Ac-Lys-(Ac-Lys)Lys-Ser-Tyr-Ser-Nle-Glu-His-(D-Phe)-Arg-Trp-Gly-Lys-Pro-Val-NH$_2$;
Ac-Lys-(Ac-Lys)Lys-Tyr-Val-Met-Gly-His-Phe-Arg-(D-Trp)-Asp-Arg-Phe-Gly-NH$_2$;
Ac-Lys-(Ac-Lys)Lys-Tyr-Val-Met-Gly-His-Phe-Arg-Trp-Asp-Arg-Phe-Gly-NH$_2$;
Ac-Lys-(Ac-Lys)Lys-Tyr-Val-Met-Gly-His-(D-Phe)-Arg-(D-Trp)-Asp-Arg-Phe-Gly-NH$_2$;
Ac-Lys-(Ac-Lys)Lys-Tyr-Val-Met-Gly-His-Phe-Arg-(D-Trp)-Asp-Arg-(D-Phe)-Gly-NH$_2$;
Ac-Lys-(Ac-Lys)Lys-Tyr-Val-Nle-Gly-His-Phe-Arg-(D-Trp)-Asp-Arg-Phe-Gly-NH$_2$;
Ac-Lys-(Ac-Lys)Lys-Tyr-Val-Nle-Gly-His-Phe-Arg-Trp-Asp-Arg-Phe-Gly-NH$_2$;
Ac-Lys-(Ac-Lys)Lys-Tyr-Val-Nle-Gly-His-(D-Phe)-Arg-Trp-Asp-Arg-Phe-Gly-NH$_2$;
Ac-Lys-(Ac-Lys)Lys-Tyr-Val-Nle-Gly-His-(D-Phe)-Arg-(D-Trp)-Asp-Arg-Phe-Gly-NH$_2$;
and pharmaceutically acceptable salts thereof.

* * * * *